(12) United States Patent
Picker et al.

(10) Patent No.: US 10,316,334 B2
(45) Date of Patent: *Jun. 11, 2019

(54) CYTOMEGALOVIRUS VECTORS ENABLING CONTROL OF T CELL TARGETING

(71) Applicant: Oregon Health & Science University, Portland, OR (US)

(72) Inventors: Louis Picker, Portland, OR (US); Scott Hansen, Portland, OR (US); Klaus Frueh, Portland, OR (US); Daniel Malouli, Hillsboro, OR (US)

(73) Assignee: Oregon Health & Science University, Portland, OR (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/693,558

(22) Filed: Sep. 1, 2017

(65) Prior Publication Data

US 2018/0087069 A1   Mar. 29, 2018

Related U.S. Application Data

(63) Continuation of application No. 14/773,130, filed as application No. PCT/US2014/020690 on Mar. 5, 2014, now Pat. No. 9,783,823.

(60) Provisional application No. 61/772,962, filed on Mar. 5, 2013.

(51) Int. Cl.

| C12N 7/00 | (2006.01) |
|---|---|
| A61K 39/00 | (2006.01) |
| A61K 39/04 | (2006.01) |
| A61K 39/12 | (2006.01) |
| A61K 39/21 | (2006.01) |
| A61K 48/00 | (2006.01) |
| C12N 15/86 | (2006.01) |

(52) U.S. Cl.
CPC .............. *C12N 15/86* (2013.01); *A61K 39/04* (2013.01); *A61K 39/12* (2013.01); *A61K 39/21* (2013.01); *C12N 7/00* (2013.01); *A61K 48/00* (2013.01); *A61K 2039/5256* (2013.01); *A61K 2039/572* (2013.01); *C12N 2710/16011* (2013.01); *C12N 2710/16143* (2013.01); *C12N 2740/15034* (2013.01)

(58) Field of Classification Search
CPC ................................. C12N 15/86; C12N 7/00; C12N 2710/16011; C12N 2710/16143; C12N 2740/15034; C12N 5/0636; C12N 15/64; C12N 15/67; C12N 2710/16034; C12N 2710/16041; C12N 2710/16061; C12N 2710/16111; C12N 2710/16134; C12N 2710/16141; A61K 39/21; A61K 39/04; A61K 39/12; A61K 48/00; A61K 2039/5256; A61K 2039/572; C07K 14/005

See application file for complete search history.

(56) References Cited

U.S. PATENT DOCUMENTS

| 5,168,062 A | 12/1992 | Stinski |
|---|---|---|
| 5,273,876 A | 12/1993 | Hock et al. |
| 5,385,839 A | 1/1995 | Stinski |
| 5,720,957 A | 2/1998 | Jones et al. |
| 5,830,745 A | 11/1998 | Hock et al. |
| 5,833,993 A | 11/1998 | Wardley et al. |
| 6,033,671 A | 3/2000 | Frueh et al. |
| 7,892,822 B1 | 2/2011 | Koszinowski et al. |
| 9,249,427 B2 | 2/2016 | Picker et al. |
| 9,541,553 B2 | 1/2017 | Picker et al. |
| 9,783,823 B2 | 10/2017 | Picker et al. |
| 9,862,972 B2 | 1/2018 | Picker et al. |
| 9,982,241 B2 | 5/2018 | Picker et al. |
| 2002/0176870 A1 | 11/2002 | Schall et al. |
| 2003/0118568 A1 | 6/2003 | Crew |
| 2004/0086489 A1 | 5/2004 | Schall et al. |
| 2004/0248300 A1 | 12/2004 | Preston |
| 2005/0064394 A1 | 3/2005 | Liu et al. |
| 2005/0118192 A1 | 6/2005 | Boursnell et al. |

(Continued)

FOREIGN PATENT DOCUMENTS

| EP | 0521427 A1 | 1/1993 |
|---|---|---|
| WO | WO-8810311 A1 | 12/1988 |

(Continued)

OTHER PUBLICATIONS

Altschul, S.F. and Gish W., "Local Alignment Statistics," Methods in Enzymology 266:460-480, Academic Press, United States (1996).
Altschul, S.F., et al., "Basic Local Alignment Search Tool," Journal of Molecular Biology 215(3):403-410, Elsevier, England (Oct. 1990).
Andre, S., et al., "Increased Immune Response Elicited by DNA Vaccination With a Synthetic gp120 Sequence With Optimized Codon Usage," Journal of Virology 72(2):1497-1503, American Society for Microbiology, United States (Feb. 1998).
Barsov, E.V., et al., "Transduction of Siv-specific Tcr Genes Into Rhesus Macaque Cd8+ T Cells Conveys the Ability to Suppress Siv Replication," PLoS One 6(8):e23703, Public Library of Science, United States ( Aug. 2011).
Basta, S., et al., "Inhibitory Effects of Cytomegalovirus Proteins US2 and US11 Point to Contributions From Direct Priming and Cross-priming in Induction of Vaccinia Virus-specific Cd8(+) T Cells," Journal of Immunology 168(11):5403-5408, American Association of Immunologists, United States (Jun. 2002).

(Continued)

*Primary Examiner* — Rachel B Gill
(74) *Attorney, Agent, or Firm* — Sterne, Kessler, Goldstein & Fox P.L.L.C.

(57) ABSTRACT

CMV vectors comprising a heterologous protein antigen, an active UL131 protein (or an ortholog thereof), and an active UL128 protein (or an ortholog thereof) but lacking an active UL130 protein (or an ortholog thereof) are provided. CMV vectors comprising a heterologous protein antigen, an active UL131 protein (or an ortholog thereof), and an active UL130 protein (or an ortholog thereof) but lacking an active UL128 protein are also provided. In addition, methods of using CMV vectors to generate an immune response characterized as having at least 10% of the CD8+ T cells directed against epitopes presented by MHC Class II are provided.

23 Claims, 17 Drawing Sheets

Specification includes a Sequence Listing.

(56) References Cited

U.S. PATENT DOCUMENTS

| | | | |
|---|---|---|---|
| 2006/0019369 A1* | 1/2006 | Hahn | A61K 39/245 435/235.1 |
| 2008/0199493 A1* | 8/2008 | Picker | A61K 39/04 424/208.1 |
| 2009/0148477 A1 | 6/2009 | Bruder et al. | |
| 2009/0203144 A1 | 8/2009 | Beaton et al. | |
| 2009/0297555 A1 | 12/2009 | Kemble et al. | |
| 2010/0142823 A1 | 6/2010 | Wang et al. | |
| 2013/0089559 A1* | 4/2013 | Grawunder | C07K 16/088 424/139.1 |
| 2013/0136768 A1 | 5/2013 | Picker et al. | |
| 2013/0142823 A1 | 6/2013 | Picker et al. | |
| 2013/0156808 A1 | 6/2013 | Jonjic | |
| 2013/0202638 A1 | 8/2013 | Thirion et al. | |
| 2014/0141038 A1 | 5/2014 | Picker et al. | |
| 2016/0354461 A1 | 12/2016 | Picker et al. | |
| 2017/0143809 A1 | 5/2017 | Nelson et al. | |
| 2017/0350887 A1 | 12/2017 | Picker et al. | |
| 2018/0133321 A1 | 5/2018 | Picker et al. | |
| 2018/0282378 A1 | 10/2018 | Frueh et al. | |
| 2018/0298404 A1 | 10/2018 | Frueh et al. | |

FOREIGN PATENT DOCUMENTS

| | | | |
|---|---|---|---|
| WO | WO-9604383 A1 | 2/1996 | |
| WO | WO-9906582 A1 | 2/1999 | |
| WO | WO-02062296 A2 | 8/2002 | |
| WO | WO-2006031264 A2 | 3/2006 | |
| WO | WO-2010101663 A2 | 9/2010 | |
| WO | WO-2011093858 A1 * | 8/2011 | A61K 39/0011 |
| WO | WO-2011119920 A2 | 9/2011 | |
| WO | WO-2011138040 A2 | 11/2011 | |
| WO | WO-2011143650 A2 * | 11/2011 | A61K 39/12 |
| WO | WO-2011143653 A2 | 11/2011 | |
| WO | WO-2012170765 A2 | 12/2012 | |
| WO | WO-2014138209 A1 | 9/2014 | |
| WO | WO-2016130693 A1 * | 8/2016 | A61K 48/00 |
| WO | WO-2017087921 A1 | 5/2017 | |
| WO | WO-2018005559 A1 * | 1/2018 | |

OTHER PUBLICATIONS

Besold, K., et al., "Immune Evasion Proteins GpUS2 and GpUS11 of Human Cytomegalovirus Incompletely Protect Infected Cells From CD8 T Cell Recognition," Virology 391(1):5-19, Academic Press, United States (Aug. 2009).

Borst, E and Messerle, M, "Development of a Cytomegalovirus Vector for Somatic Gene Therapy," Bone Marrow Transplant 25 Suppl 2:S80-S82, Nature Publishing Group (May 2000).

Borst, E.M and Messerle, M, "Construction of a Cytomegalovirus-based Amplicon: a Vector With a Unique Transfer Capacity," Human Gene Therapy 14(10):959-970, M.A. Liebert, United States (Jul. 2003).

Bresnahan, W.A and Shenk, T.E, "UL82 Virion Protein Activates Expression of Immediate Early Viral Genes in Human Cytomegalovirus-infected Cells," Proceedings of the National Academy of Sciences of the United States of America 97(26):14506-14511, National Academy of Sciences, United States (Dec. 2000).

Bresnahan, W.A., et al., "Replication of Wild-type and Mutant Human Cytomegalovirus in Life-extended Human Diploid Fibroblasts," Journal of Virology 74(22):10816-10818, American Society for Microbiology, United States (Nov. 2000).

Brondke, H. "Human Herpesvirus 5, Towne Strain," US3 (NCBI GenBank Acc. No. AAS49002), Dep. Apr. 8, 2004.

Brondke, H. "Human Herpesvirus 5, Towne Strain," US6 (NCBI GenBank Acc. No. AAS49004), Dep. Apr. 8, 2004.

Brown, B.D and Naldini.L, "Exploiting and Antagonizing MicroRNA Regulation for Therapeutic and Experimental Applications," Nature reviews Genetics 10(8):578-585, Nature Publishing Group, England (Aug. 2009).

Campadelli-Flume, et al., Editors, "Chapter 15: Betaherpes Viral Genes and Their Functions" Human Herpesviruses: Biology, Therapy, and Immunoprophylaxis. Cambridge: Cambridge University Press, 2007.

Cantrell, S.R and Bresnahan, W.A, "Human Cytomegalovirus (HCMV) UL82 Gene Product (pp71) Relieves hDaxx-mediated Repression of Hcmv Replication," Journal of Virology 80(12):6188-6191, American Society for Microbiology, United States (Jun. 2006).

Cantrell, S.R and Bresnahan, W.A, "Interaction Between the Human Cytomegalovirus UL82 Gene Product (pp71) and HDaxx Regulates Immediate-early Gene Expression and Viral Replication," Journal of Virology 79(12):7792-7802, American Society for Microbiology, United States (Jun. 2005).

Chang, W.L and Barry, P.A, "Cloning of the Full-length Rhesus Cytomegalovirus Genome as an Infectious and Self-Excisable Bacterial Artificial Chromosome for Analysis of Viral Pathogenesis," Journal of Virology 77(9):5073-5083, American Society for Microbiology, United States (May 2003).

Chau, N.H., et al., "Transcriptional Regulation of the Human Cytomegalovirus US11 Early Gene," Journal of Virology 73(2):863-870, American Society for Microbiology, United States (Feb. 1999).

Corpet, F, "Multiple Sequence Alignment With Hierarchical Clustering," Nucleic Acids Research 16(22):10881-10890, Oxford University Press, England (Nov. 1988).

Davison, A.J and Stow, N.D, "New Genes From Old: Redeployment of DUTPase by Herpesviruses," Journal of Virology 79(20):12880-12892, American Society for Microbiology, United States (Oct. 2005).

Do, J.S., et al., "Unexpected Role for MHC II-Peptide Complexes in Shaping CD8 T-Cell Expansion and Differentiation in Vivo," Proceedings of the National Academy of Sciences 109(31):12698-12703, National Academy of Sciences, United States (Jul. 2012).

Dudek, T and Knipe, D.M, "Replication-defective Viruses as Vaccines and Vaccine Vectors," Virology 344(1):230-239, Academic Press, United States (Jan. 2006).

Dunn, W., et al., "Functional Profiling of a Human Cytomegalovirus Genome," Proceedings of the National Academy of Sciences of the United States of America 100(24):14223-14228, National Academy of Sciences, United States (Nov. 2003).

European Search Report for EP Application No. EP16200334,The Hague, dated May 18, 2017.

European Search Report for EP Application No. EP17197412, Munich, Germany, dated Apr. 23, 2018.

Felgner, J.H., et al., "Enhanced Gene Delivery and Mechanism Studies With a Novel Series of Cationic Lipid Formulations," Journal of Biological Chemistry 269(4):2550-2561, American Society for Biochemistry and Molecular Biology, United States (Jan. 1994).

Office Action dated Apr. 26, 2017, in U.S. Appl. No. 14/773,130, Picker, Louis, et al., filed Sep. 4, 2015, 11 pages.

Gilicze, A.B., et al., "Myeloid-Derived microRNAs, miR-223, miR27a, and miR-652, Are Dominant Players in Myeloid Regulation," BioMed Research International 2014:870267, Hindawi Publishing Corporation, United States (Aug. 2014).

Gill, R.B., et al., "Coding Potential of Ul/b' From the Initial Source of Rhesus Cytomegalovirus Strain 68-1," Virology 447(1-2):208-212, Academic Press, United States (Dec. 2013).

Gish, W and States, D.J, "Identification of Protein Coding Regions by Database Similarity Search," Nature Genetics 3(3):266-272, Nature Publishing Group, United States (Mar. 1993).

Goodman-Snitkoff, G., et al., "Role of Intrastructural/intermolecular Help in Immunization With Peptide-phospholipid Complexes," Journal of Immunology 147(2):410-415, American Association of Immunologists, United States (Jul. 1991).

Goodrum, F., et al., "Human Cytomegalovirus Persistence," Cellular Microbiology 14(5):644-655, Wiley-Blackwell, England (May 2012).

Gorman, S., et al., "Prior Infection with Murine Cytomegalovirus (MCMV) Limits the Immunocontraceptive Effects of an MCMV Vector Expressing the Mouse Zona-Pellucida-3 Protein," Vaccine 26(31):3860-3869, Elsevier Science, Netherlands (Jul. 2008).

Grimwood, J., et al. "NCBI GenBank Direct Submission," Acc. No. AC146906, Sub. Nov. 5, 2003.

Hagemier, S.C., "Functional Analysis of the Human Cytomegalovirus UL82 gene product PP71 protein during Virus Replication," Doctoral Dissertation, The University of Texas Southwestern Medical Center at Dallas, May 2007, pp. 1-181.

(56) References Cited

OTHER PUBLICATIONS

Hahn, G., et al., "Human Cytomegalovirus UL131-128 Genes are Indispensable for Virus Growth in Endothelial Cells and Virus Transfer to Leukocytes," Journal of Virology 78(18):10023-10033, American Society for Microbiology, United States (Sep. 2004).

Halary, F., et al., "Human Cytomegalovirus Binding to DC-SIGN is Required for Dendritic Cell Infection and Target Cell Trans-Infection," Immunity 17(5):653-664, Cell Press, United States (Nov. 2002 ).

Hancock, J.M and Armstrong, J.S., "SIMPLE34: an Improved and Enhanced Implementation for Vax and Sun Computers of the Simple Algorithm for Analysis of Clustered Repetitive Motifs in Nucleotide Sequences," Computer Applications in the Biosciences,10(1):67-70, Oxford University Press, England (Feb. 1994).

Hancock, M.H., et al., "Rhesus Cytomegalovirus Encodes Seventeen Micrornas that are Differentially Expressed In Vitro and In Vivo," Virology 425(2):133-142, Academic Press, United States (Apr. 2012).

Hansen, S.G., et al., "Broadly Targeted Cd8$^+$T Cell Responses Restricted by Major Histocompatibility Complex E," Science 351(6274):714-720, American Association for the Advancement of Science, United States (Feb. 2016).

Hansen, S.G., et al., "Complete Sequence and Genomic Analysis of Rhesus Cytomegalovirus," Journal of Virology 77(12):6620-6636, American Society for Microbiology, United States (Jun. 2003).

Hansen, S.G., et al., "Cytomegalovirus Vectors Violate CD8+ T Cell Epitope Recognition Paradigms," Science 340(6135):1237874, American Association for the Advancement of Science, United States (May 2013).

Hansen, S.G., et al., "Effector Memory T Cell Responses are Associated With Protection of Rhesus Monkeys From Mucosal Simian Immunodeficiency Virus Challenge," Nature Medicine 15(3):293-299, Nature Publishing Company, United States (Mar. 2009).

Hansen, S.G., et al., "Evasion of Cd8+ T Cells Is Critical for Superinfection by Cytomegalovirus," Science 328(5974):102-106, American Association for the Advancement of Science, United States (Apr. 2010).

Hansen, S.G., et al., "Immune Clearance of Highly Pathogenic SIV Infection," Nature 502(7469):100-104, Nature Publishing Group, United Kingdom (Oct. 2013).

Hansen, S.G., et al., "Profound Early Control of Highly Pathogenic SIV by an Effector Memory T-cell Vaccine," Nature 473(7348):523-527, Nature Publishing Group, England (May 2011).

Higgins, D.G and Sharp, P.M, "CLUSTAL: A Package for Performing Multiple Sequence Alignment on a Microcomputer," Gene 73(1):237-244, Elsevier/North-Holland, Netherlands (Dec. 1988).

Higgins, D.G., and Sharp, P.M., "Fast and Sensitive Multiple Sequence Alignments on a Microcomputer," Computer Applications in the Biosciences 5(2):151-153, Oxford University Press, United Kingdom (Apr. 1989).

Huang, X., et al., "Parallelization of a Local Similarity Algorithm," Computer Applications in the Biosciences 8(2):155-165, Oxford University Press, England (Apr. 1992).

International Preliminary Report on Patentability for International Application No. PCT/US2016/017373, The International Bureau of WIPO, Geneva, Switzerland, dated Aug. 15, 2017, 8 pages.

International Search Report and Written opinion for International Application No. PCT/US2015/040807, European Patent Office, HV Rijswijk, dated Oct. 28, 2015, 6 pages.

International Search Report and Written opinion for International Application No. PCT/US2016/017373, Korean Intellectual Property Office, Republic of Korea, dated May 23, 2016.

International Search Report for International Application No. PCT/US2011/036657, Korean Intellectual Property Office, Republic of Korea, dated Mar. 28, 2012.

International Search Report for International Application No. PCT/US2012/041475, Korean Intellectual Property Office, Republic of Korea, dated Dec. 14, 2012.

James, SH and Prichard, M.N., "The Genetic Basis of Human Cytomegalovirus Resistance and Current Trends in Antiviral Resistance Analysis," Infectious Disorders Drug Targets, 11(5):504-513, Bentham Science Publishers, United Arab Emirates (Oct. 2011).

Jones, T.R., et al., "Multiple Independent Loci Within the Human Cytomegalovirus Unique Short Region Down-regulate Expression of Major Histocompatibility Complex Class I Heavy Chains," Journal of Virology 69(8):4830-4841, American Society for Microbiology, United States (Aug. 1995).

Jones, T.R., et al., "Replacement Mutagenesis of the Human Cytomegalovirus Genome: US10 and US11 Gene Products are Nonessential," Journal of Virology 65(11):5860-5872, American Society for Microbiology, United States (Nov. 1991).

Kaech, S.M., et al., "Effector and Memory T-cell Differentiation: Implications for Vaccine Development," Nature Reviews. Immunology 2(4):251-262, Nature Pub. Group, England (2002).

Kalejta, R.F, "Human Cytomegalovirus PP71: a New Viral Tool to Probe the Mechanisms of Cell Cycle Progression and Oncogenesis Controlled by the Retinoblastoma Family of Tumor Suppressors," Journal of Cellular Biochemistry 93(1):37-45, Wiley-Liss, United States (Sep. 2004).

Karlin, S. and Altschul, S.E., "Methods for Assessing the Statistical Significance of Molecular Sequence Features by using General Scoring Schemes," Proceedings of the National Academy of Sciences USA 87(6):2264-2268, National Academy of Sciences, United States (Mar. 1990).

Karlin, S, and Altschul, S.F., "Applications and Statistics for Multiple High-scoring Segments in Molecular Sequences," Proceedings of the National Academy of Sciences USA 90(12):5873-5877, National Academy of Sciences, United States (Jun. 1993).

Karrer, U., et al., "Expansion of Protective CD8+ T-Cell Responses Driven by Recombinant Cytomegaloviruses," Journal of Virology 78(5):2255-2264, American Society for Microbiology, United States (Mar. 2004).

Kropff, B and Mach, M, "Identification of the Gene Coding for Rhesus Cytomegalovirus Glycoprotein B and Immunological Analysis of the Protein," 78(Pt 8):1999-2007, Microbiology Society, England (Aug. 1997).

Lilja, A.E., et al., "Functional Genetic Analysis of Rhesus Cytomegalovirus: Rh01 Is an Epithelial Cell Tropism Factor," Journal of Virology 82(5):2170-2181, American Society for Microbiology, United States (Mar. 2008).

Mahmood, K., et al., "Human Cytomegalovirus Plasmid-based Amplicon Vector System for Gene Therapy," Genetic vaccines and therapy 3(1):1, BioMed Central, England (Jan. 2005).

Malouli, D., et al., "Reevaluation of the Coding Potential and Proteomic Analysis of the Bac-derived Rhesus Cytomegalovirus Strain 68-1," Journal of Virology 86(17):8959-8973, American Society for Microbiology, United States (Sep. 2012).

Marshall, K.R., et al., "Activity and Intracellular Localization of the Human Cytomegalovirus Protein PP71," The Journal of general virology 83(Pt 7):1601-1612, Microbiology Society, England (Jul. 2002).

Maussang, D., et al., "Human Cytomegalovirus-encoded Chemokine Receptor US28 Promotes Tumorigenesis," Proceedings of the National Academy of Sciences of the United States of America 103(35):13068-13073, National Academy of Sciences, United States (Aug. 2006).

McGregor, A., et al., "Expression of the Human Cytomegalovirus UL97 Gene in a Chimeric Guinea Pig Cytomegalovirus (GPCMV) Results in Viable Virus with Increased Susceptibility to Ganciclovir and Maribavir," Antiviral Research 78(3):250-259, Elsevier, Netherlands (Jun. 2008).

McGregor, A., et al., "Molecular, Biological, and in Vivo Characterization of the Guinea Pig Cytomegalovirus (CMV) Homologs of the Human Cmv Matrix Proteins pp71 (UL82) and pp65 (UL83)," Journal of virology 78(18):9872-9889, American Society for Microbiology, United States (Sep. 2004).

Miller, M.D., et al., "Vaccination of Rhesus Monkeys With Synthetic Peptide in a Fusogenic Proteoliposome Elicits Simian Immunodeficiency Virus-specific Cd8+ Cytotoxic T Lymphocytes," Journal of Experimental Medicine 176(6):1739-1744, Rockefeller University Press, United States (Dec. 1992).

(56) References Cited

OTHER PUBLICATIONS

Mohr, C.A., et al., "A Spread-deficient Cytomegalovirus for Assessment of First-target Cells in Vaccination," Journal of virology 84(15):7730-7742, American Society for Microbiology, United States (Aug. 2010 ).

Mohr, C.A., et al., "Engineering of Cytomegalovirus Genomes for Recombinant Live Herpesvirus Vaccines," International Journal of Medical Microbiology 298(1-2):115-125, Urban & Fischer Verlag, Germany (Jan. 2008).

Moutaftsi, M., et al., "Human Cytomegalovirus Inhibits Maturation and Impairs Function of Monocyte-derived Dendritic Cells," Blood 99(8):2913-2921, American Society of Hematology, United States (Apr. 2002).

Murphy, C.G., et al., "Vaccine Protection Against Simian Immunodeficiency Virus by Recombinant Strains of Herpes Simplex Virus," Journal of virology 74(17):7745-7754, American Society for Microbiology, United States (Sep. 2000).

Murphy, E., et al., "Coding Potential of Laboratory and Clinical Strains of Human Cytomegalovirus," Proceedings of the National Academy of Sciences of the United States of America 100(25):14976-14981, National Academy of Sciences, United States (Dec. 2003).

Murrell, L., et al., "Impact of Sequence Variation in the UL128 Locus on Production of Human Cytomegalovirus in Fibroblast and Epithelial Cells," Journal of Virology 87(19):10489-10500, American Society for Microbiology, United States (Oct. 2013).

Myers, E.W., and Miller, W., "Optimal Alignment in Linear Space," Computer Applications in the Biosciences 4(1):1-13, Oxford University Press, England (Mar. 1988).

Kim, S., et al., "Human Cytomegalovirus MicroRNA miR-US4-1 Inhibits CD8(+) T cell Responses by Targeting the Aminopeptidase ERAP1," Nature Immunology 12(10):984-991, Nature America Inc, United States (Sep. 2011).

Needleman, S.B. and Wunsch, C.D., "A General Method Applicable to the Search for Similarities in the Amino Acid Sequence of Two Proteins," Journal of Molecular Biology 48(3):443-453, Academic Press, England (Mar. 1970).

Matthews, T.J., et al., "Prospects for Development of a Vaccine Against HTLV-III-Related Disorders," AIDS Research and Human Retroviruses 3(s1):197-206, Mary Ann Liebert, United States (1987).

Olaleye, O.D., et al., "Cytomegalovirus Infection Among Tuberculosis Patients in a Chest Hospital in Nigeria," Comparative Immunology, Microbiology and Infectious Diseases 13(2):101-106, Elsevier Science Ltd, England (1990).

Onuffer, J.J and Horuk, R, "Chemokines, Chemokine Receptors and Small-molecule Antagonists: Recent Developments," Trends in Pharmacological Sciences 23(10):459-467, Published by Elsevier in Association with the International Union of Pharmacology, England (Oct. 2002).

Oxford, K.L., et al., "Protein Coding Content of the ULb' Region of Wild-Type Rhesus Cytomegalovirus," Virology 373(1):181-188, Academic Press, United States (Mar. 2008).

Pearce, E.L., et al., "Functional Characterization of MHC Class II-Restricted CD8+CD4− and CD8−CD4− T cell Responses to Infection in CD4−/− Mice," Journal of Immunology 173(4):2494-2499, American Association of Immunologists, United States (Aug. 2004).

Pearson, W.R. and Lipman, D.J., "Improved Tools for Biological Sequence Comparison," Proceedings of the National Academy of Sciences of the United States of America 85(8):2444-2448, National Academy of Sciences, United States (Apr. 1988).

Pearson, W.R., "Using the FASTA Program to Search Protein and DNA Sequence Databases," Methods in Molecular Biology 24:307-331, Humana Press, United States (Feb. 1994).

Hanley, P.J., et al., "Controlling cytomegalovirus: helping the immune system take the lead," Viruses, 6(6):2242-2258, MDPI, Switzerland (May 2014).

Heineman, T.C., "Chapter 71: Human cytomegalovirus vaccines." In: Arvin, A, Campadelli-Fiume, G, Mocarski, E, et al., eds. Human Herpesviruses: Biology, Therapy, and Immunoprophylaxis, Cambridge: Cambridge University Press, 2007.

Picker, L.J., et al., "New paradigms for HIV/AIDS vaccine development," Annual Review of Medicine 63:95-111, Annual Reviews, United States (Feb. 2012).

Pietra, G., et al., "HLA-E-Restricted Recognition of Cytomegalovirus-derived Peptides by Human CD8+ Cytolytic T Lymphocytes," Proceedings of the National Academy of Sciences of the United States of America 100(19):10896-10901, National Academy of Sciences, United States (Sep. 2003).

International Preliminary Report on Patentability for International Application No. PCT/US2015/040807 , The International Bureau of WIPO, Geneva, Switzerland, dated Jan. 17, 2017, 8 pages.

Joosten, S.A., et al., "Characteristics of HLA-E Restricted T-Cell Responses and Their Role in Infectious Diseases," Journal of Immunology Research, 2016:2695396, Hindawi Publishing Corporation, Egypt (Sep. 2016).

Lauron, E.J., et al., "Human Cytomegalovirus Infection of Langerhans-Type Dendritic Cells Does Not Require the Presence of the gH/gL/UL128-131A Complex and Is Blocked after Nuclear Deposition of Viral Genomes in Immature Cells," Journal of Virology, 88(1): 403-416, American Society for Microbiology, United States (Jan. 2014).

Plotkin, S.A., et al., "Vaccines for the Prevention of Human Cytomegalovirus Infection," Reviews of Infectious Diseases 12 Suppl 7:S827-S838, University of Chicago Press, United States (Sep.-Oct. 1990).

Powers, C and Fruh, K, "Rhesus CMV: an Emerging Animal Model for Human CMV," Medical Microbiology and Immunology 197(2):109-115, Springer-Verlag, Germany (Jun. 2008).

Smith, I.L., et al., "High-level resistance of cytomegalovirus to ganciclovir is associated with alterations in both the UL97 and DNA polymerase genes," Journal of Infectious Diseases, 176(1): 69-77, Oxford University Press, United States (Jul. 1997). Erratum in: Journal of Infectious Diseases, 177(4):1140-1141 (Apr. 1998).

Redwood, A.J., et al., "Use of a Murine Cytomegalovirus K181-derived Bacterial Artificial Chromosome as a Vaccine Vector for Immunocontraception," Journal of virology 79(5):2998-3008, American Society for Microbiology, United States (Mar. 2005).

Office Action dated Mar. 14, 2016, in U.S. Appl. No. 14/179,152, inventors Picker, L., et al., filed Feb. 12, 2014, 20 pages.

Rizvanov, A.A., et al., "Generation of a Recombinant Cytomegalovirus for Expression of a Hantavirus Glycoprotein," Journal of virology 77(22):12203-12210, American Society for Microbiology, United States (Nov. 2003).

Ryckman, B.J., et al., "Characterization of the Human Cytomegalovirus Gh/gl/ul128-131 Complex That Mediates Entry Into Epithelial and Endothelial Cells," Journal of virology 82(1):60-70, American Society for Microbiology, United States (Jan. 2008).

Sambrook, J., et al., "Molecular Cloning: A Laboratory Manual," Third Edition, Cold Spring Harbor Laboratory Press, United States (2001).

Schleiss, M.R., et al., "Genetically Engineered Live-attenuated Cytomegalovirus (CMV) Vaccines Improve Pregnancy Outcome in the Guinea-pig Model of Congenital CMV Infection," Retrovirology 5(1):1-3, (Apr. 2008).

Schuessler, A., et al., "Charge Cluster-to-Alanine Scanning of UL128 for Fine Tuning of the Endothelial Cell Tropism of Human Cytomegalovirus," Journal of Virology, 82(22):11239-11246, American Society for Microbiology, United States (Nov. 2008).

Schuessler, A., et al., "Mutational Mapping of UL130 of Human Cytomegalovirus Defines Peptide Motifs within the C-Terminal Third as Essential for Endothelial Cell Infection," Journal of Virology, 84(18): 9019-9026, American Society for Microbiology, United States (Sep. 2010).

Smith, T.F. and Waterman, M.S., "Comparison of Biosequences," Advances in Applied Mathematics 2(4):482-489, Academic Press, Inc., United States (Dec. 1981).

European Search Report for EP Application No. EP11008462, Munich, Germany, dated Jul. 26, 2012.

GenBank Report, Accession No. NP_057850, (published Aug. 1, 2000).

(56) References Cited

OTHER PUBLICATIONS

Michaelson, J.S and Leder, P., "RNAi Reveals Anti-Apoptotic and Transcriptionally Repressive Activities of DAXX," Journal of Cell Science 116(Pt 2):345-352, Company of Biologists, London (Jan. 2003).

Nicholson J.P., et al., "Properties of Virion Transactivator Proteins encoded by Primate Cytomegaloviruses," Journal of Virology, 6:65, BioMed Central, England (May 2009).

Office Action dated Aug. 8, 2016, in U.S. Appl. No. 14/773,130, Picker, Louis, et al., filed Sep. 4, 2015, 16 pages.

Oxxon Terapeutics Licenses Rights to Xenova's DISC-HSV and DISC-GM-CSF Vector Technolgies, BusinessWire, Jan. 13, 2005.

Tessmer, M.S., et al., "Salivary Gland NK Cells Are Phenotypically and Functionally Unique," PLoS Pathogens 7(1):e1001254, Public Library of Science, United States (Jan. 2011).

Ulmer, J.B., et al., "Heterologous Protection against Influenza by injection of DNA Encoding a Viral Protein," Science 259(5102):1745-1749, American Association for the Advancement of Science, United States (Mar. 1993).

Ulmer, J.B, "Tuberculosis DNA Vaccines," Scandinavian Journal of Infectious Diseases 33(4):246-248, Informa Healthcare, England (2001).

Wang, D and Shenk,T ., "Human cytomegalovirus UL131 Open Reading Frame is Required for Epithelial Cell Tropism," Journal of Virology, 79(16):10330-10338, American Society for Microbiology, United States (Aug. 2005).

Wang, X., et al., "Murine Cytomegalovirus Abortively Infects Human Dendritic Cells, Leading to Expression and Presentation of Virally Vectored Genes," Journal of virology 77(13):7182-7192, American Society for Microbiology, United States (Jul. 2003).

Wiertz, E.J., et al., "The Human Cytomegalovirus US11 Gene Product Dislocates Mhc Class I Heavy Chains From the Endoplasmic Reticulum to the Cytosol," Cell 84(5):769-779, Cell Press, United States (Mar. 1996).

Wu, F., et al., "Role of Specific MicroRNAs for Endothelial Function and Angiogenesis," Biochemical and Biophysical Research Communications 386(4):549-553, Elsevier, United States (Sep. 2009).

Written Opinion for International Application PCT/US2014/020690, filed Mar. 5, 2014, International Search Authority, Daejon, Korea, dated Jul. 17, 2014, 6 pages.

Cranage, M., et a., "Carriers for the delivery of a vaccine against respiratory syncytial virus," Expert Opinion on Biological Therapy 5(7): 939-952, Taylor & Francis, England (2005).

Antonis A.F., et al., "Vaccination with recombinant modified vaccinia virus Ankara expressing bovine respiratory syncytial virus (bRSV) proteins protects calves against RSV challenge," Vaccine 25(25):4818-4827, Elsevier, Netherlands (2007).

Kovarik, J., et al., "Induction of adult-like antibody, Th1, and CTL responses to measles hemagglutinin by early life murine immunization with an attenuated vaccinia derived NYVAC (K1L) viral vector," Virvology 285(1):12-20, Elsevier, Netherlands (2001).

Welter, J., et al., "Mucosal vaccination with recombinant poxvirus vaccine protects ferrets against symptomatic CDV infection," Vaccine 17(4):308-318, Elsevier, Netherlands (1999).

Guillaume, V., et al., "Nipah Virus: Vaccination and passive protection studies in a hamster model," Journal of Virology 78(2):834-840, The American Society for Microbiology, United States (2004).

Wyatt, L.S., et al., "Development of a replication-deficient recombinant vaccinia virus vaccine effective against parainfluenza virus 3 infection in an animal model," Vaccine 14(15):1451-1458, Elsevier, Netherlands (1996).

Kenjiro, I., et al., "Long-term protective immunity to rinderpest in cattle following a single vaccination with a recombinant vaccinia virus expressing the virus haemagglutinin protein," Journal of General Virology 81(6):1439-1446, Microbiology Society, United Kingdom (2000).

Office Action for dated Aug. 4, 2015, in U.S. Appl. No. 11/597,457, inventors Picker et al., filed Apr. 28, 2008, 31 pages.

Office Action dated Jan. 9, 2015, in U.S. Appl. No. 14/179,152, inventors Picker, L., et al., filed Feb. 12, 2014, 16 pages.

\* cited by examiner

68-1.2 ΔUL128 RhCMV/gag vector-vaccinated macaques:

68-1.2 ΔUL130 RhCMV/gag vector-vaccinated macaques:

CYTOMEGALOVIRUS VECTORS ENABLING CONTROL OF T CELL TARGETING

CROSS-REFERENCE

This application claims the benefit of and priority to U.S. Provisional Application No. 61/772,962, filed Mar. 5, 2013, the international application No. PCT/US2014/020690, filed Mar. 5, 2014, and U.S. patent application Ser. No. 14/773,130, filed Sep. 4, 2015, each of which is incorporated by reference herein in its entirety.

ACKNOWLEDGEMENT OF GOVERNMENT SUPPORT

This invention was made with the support of the United States government under the terms of grant number P01 AI094417 awarded by the National Institutes of Health. The United States government has certain rights to this invention.

REFERENCE TO A SEQUENCE LISTING

The instant application contains a Sequence Listing, which has been submitted in ASCII text file format via EFS-Web and is hereby incorporated by reference in its entirety. Said ASCII copy, created on Dec. 12, 2017, is named "3919.0060002 seq listing.txt", and is 7,500 bytes in size.

BACKGROUND $CD8^+$ T cells detect intracellular pathogens by T cell receptor (TCR)-mediated recognition of short pathogen-derived peptides selected and transported to the cell surface by class I MHC proteins (MHC-I) and an exquisite system of intracellular peptide sampling and transport (Neefjies M L et al, *Nat Rev Immunol* 11, 823 (2011); incorporated by reference herein). Although pathogens can potentially generate many thousands of different peptides of the appropriate length for $CD8^+$ T cell recognition, requirements for proteolytic processing, peptide transport, binding to available MHC-I allomorphs and TCR repertoire matching, as well as poorly understood immunoregulatory mechanisms, winnow down these candidates to a relative handful of peptide epitopes that actually serve as targets for the $CD8^+$ T cells that comprise anti-pathogen effector and memory responses (Yewdell J W et al, *Immunity* 25, 533 (2006); Irvine K et al, *Expert Rev Clin Immunol* 2, 135 (2006); Assarsson E et al, *J Immunol* 178, 7890 (2007). Despite the complexity of the process, pathogen-specific CD8 T cell responses mounted by individuals with shared MHC-I alleles tend to recognize an overlapping set of so-called immunodominant epitopes (Yewdell et al 2006 supra; Irvine et al, 2006 supra, Goulder P J and Watkins D I, *Nat Rev Immunol* 8, 619 (2008); incorporated by reference herein). For the vast majority of pathogens, $CD8^+$ T cell responses targeting such immunodominant epitopes are able to both recognize pathogen-infected cells and mount effective anti-pathogen effector and memory responses. However, this is not the case for agents with efficient immune evasion capabilities like the human immunodeficiency virus (HIV) and its simian counterpart SIV. The massive replication of these viruses, combined with their high rate of mutation and functional plasticity, allows escape from most $CD8^+$ T cell responses (Picker U et al, *Ann Rev Med* 63, 95 (2012), incorporated by reference herein). Indeed, CD8 T cell responses in the majority of subjects infected with these viruses fail to target epitopes containing conserved, functionally critical viral sequences, and do not effectively control viral replication (McMichael A J et al, *Nat Rev Immunol* 10, 11 (2010); incorporated by reference herein). While vaccination against these viruses can greatly augment the magnitude of $CD8^+$ T cell responses after infection, these larger responses target many of the same immunodominant epitopes as infection of unvaccinated subjects, and therefore are still subject to immune escape (Picker, 2012 supra; Barouch D H et al, *J Virol* 77, 7367 (2003); Mudd P A et al, *Nature* 491, 129 (2012); all of which are incorporated by reference herein). Although the AIDS vaccine field has endeavored to develop strategies capable of eliciting HIV/SIV-specific $CD8^+$ T cell responses targeting "vulnerable" epitopes across diverse MHC-I haplotypes (by either increasing recognition breadth or the focusing of responses to conserved sequences), this effort has not, to date, yielded strategies capable of substantially modifying $CD8^+$ T cell immunodominance hierarchies, nor achieved the goal of establishing protective $CD8^+$ T cell responses in the majority of individuals.

SUMMARY

An HIV/AIDS vaccine strategy using a recombinant Cytomegalovirus (CMV) expressing an HIV protein has been created as a persistent vector to generate and maintain HIV-specific effector memory T cell responses that would intercept HIV infection prior to the viral amplification needed for efficient immune evasion (Picker, 2012 supra). While this approach was not designed to prevent infection, it proved to be highly successful in animals models of HIV/AIDS with about 50% of CMV/SIV vector-vaccinated rhesus macaques (RM) challenged with highly pathogenic SIV manifesting immediate, stringent and durable virologic control (Hansen, 2011 infra).

During the course of these studies, it was observed that CMV/SIV vectors did not elicit the typical, immunodominant CD8+ T cell responses towards SIV peptides presented by the well characterized Mamu-A1*001:01 (A*01) MHC-I protein suggesting that CMV vectors induce new T cell epitopes targeted by these effective responses and that these novel responses contributed to vaccine efficacy.

It is disclosed herein that heterologous antigens such as viral and bacterial expressed by cytomegalovirus vectors induce a T cell immunodominance profile that is fundamentally different from that induced by all other known vectors. By using rhesus macaques (RM) infected with rhesus CMV (RhCMV) carrying SIV antigens as an animal model for human CMV it is shown that the SIVgag-specific $CD8^+$ responses elicited by the RhCMV/gag vector are 3-fold as broad as gag-specific $CD8^+$ T cell responses elicited by other vaccines or upon infection with SIV. It is further shown that, compared to other vaccines, CMV-elicited T cells target entirely different epitopes including a high percentage of epitopes presented by class II MHC (MHC-II). Such responses are rarely, if ever, observed in $CD8^+$ T cell responses to any other infectious agent or vaccine. It is further disclosed that the immunodominance profile is under the genetic control of CMV. Specifically, it is demonstrated the CMV genes UL128 and UL130 prevent the induction of this response. When UL128 and UL130 are present in the CMV vector, T cell responses are focused on a limited set of epitopes whereas MHC-II restricted $CD8^+$ T cells are induced by vectors that lack either UL128 or UL130. These findings allow, for the first time, the ability to genetically manipulate a vaccine vector to achieve distinct patterns of CD8+ T cell epitope recognition.

Disclosed herein are CMV vectors comprising: a heterologous protein antigen, an active UL131 protein (or an ortholog thereof), an active UL128 protein (or an ortholog thereof), but wherein the CMV vector lacks an active UL130 protein. Also disclosed herein are CMV vectors comprising: a heterologous protein antigen, an active UL131 protein (or an ortholog thereof), an active UL130 protein (or an ortholog thereof), but wherein the CMV vector lacks an active UL128 protein.

Also disclosed herein is a method of generating a CD8+ T cell response to a heterologous antigen in a subject. The method involves administering an effective amount of a CMV vector to the subject. The CMV vector is characterized by having a heterologous antigen, having an active UL131 protein, not having an active UL128 protein or not having an active UL130 protein, or by not having an active UL128 and not having an active UL130 protein. The response is characterized by at least 10% of the CD8+ T cells being directed against epitopes presented by MHC Class II.

BRIEF DESCRIPTION OF THE DRAWINGS

Some of the graphs and plots included herein may be better understood using color, which is not available in a patent application publication. Applicants consider all originally disclosed images and graphs (whether in color or not) part of the original disclosure and reserve the right to present color graphs and plots of the herein described figures in later proceedings.

FIG. 1A is an epitope map of CD8$^+$ T cell responses to peptides in RM treated as indicated. CD8$^+$ T cell responses to SIVgag were epitope-mapped using flow cytometric intracellular cytokine staining (ICS) to detect recognition of 125 consecutive 15mer gag peptides (with 11 amino acid overlap between each consecutive peptide) in rhesus macaques (RM) vaccinated with RhCMV/gag vectors (n=14). The RhCMV/gag vectors used in these experiments were derived from strain 68.1 which due to gene deletions does not express the RhCMV homologues of UL128 and UL130. Bacterial artificial chromosome (BAC)-derived RhCMV/gag (*) additionally lacks a functional homologue of UL36 which is intact in non-BAC-derived RhCMV/gag (L) (**). Additionally RM were analyzed that had been vaccinated with electroporated DNA/gag+IL-12 vectors (n=4), Ad5/gag vectors (n=3), and MVA/gag vectors (n=3) or infected with SIV (n=5; plasma viral loads<50,000 copies/ml).

Peptides resulting in CD8$^+$ T cell responses above background are indicated by a colored box, with the total number of these positive responses and the minimal number of independent epitopes potentially contained within these reactive peptides in each RM designated at right (the latter using a calculation that takes into account the fact that a single epitope can be represented in adjacent 15mers). Both the number of positive peptides and the minimum number of distinct epitopes per subject are significantly greater (p<0.0001) in the RhCMV/gag-vaccinated RM than in the RM pooled over the other groups, using two-tailed Wilcoxon rank sum tests.

FIG. 1B is two sets, each set consisting of a list of peptides and two bar graphs summarizing the determination of the core CD8$^+$ epitopes of two selected 15mer peptides targeted by CD8$^+$ T cells derived from strain 68.1 RhCMV/gag-vaccinated RM. These epitopes were determined by flow cytometric ICS analysis of CD8$^+$ T cell responses to the truncated peptides indicated in the lists of peptides. The figures shows representative examples of the 2 response patterns observed with truncated peptide sets: type 1 (red), with abrupt loss of peak responsiveness and a 9mer core epitope, and type 2 (blue), with gradual loss of peak responsiveness and a 12mer core epitope.

FIG. 1C is a set of seven plots depicting the CD8$^+$ T cell response frequencies to the parent 15mer peptides relative to those of the core peptides derived from the 15mers as shown in FIG. 1B. Responses were compared by flow cytometric ICS in 9 RM for each response.

FIG. 1D is a set of two bar graphs showing CD8$^+$ T cell responses to selected SIVgag core epitopes (blue and red), as well as selected additional SIVgag 15mers (gray). CD8+ responses were evaluated by flow cytometric ICS in 42 RM vaccinated with strain 68.1 RhCMV/gag vector deficient in UL128 and UL130. CMV-vaccinated RM are shown in the left panel and 40 SIV-infected RM are shown in the right panel as the % of RM in each category with detectable responses to these peptides.

FIG. 2A is a bar graph depicting the results of stimulation of PBMC from strain 68.1 RhCMV/gag-vaccinated RM with the indicated peptides (n=8 for $Gag_{211-222}$, $Gag_{276-284}$, $Gag_{290-301}$, $Gag_{482-490}$, $Gag_{495-506}$; n=5 for $Gag_{41-52}$, $Gag_{259-267}$). Cells were stimulated with the indicated SIVgag core epitopes (previously classified as Type 1 vs. Type 2 by the length of the core epitope as shown in FIG. 1B) in the presence of irrelevant isotype control mAbs (IgG1—clone X40+IgG2a—clone X39; 10 μg each), an anti-MHC-I mAb (w6-32; 10 μg), an anti-MHC-II mAb (G46-6; 10 μg), or the CLIP peptide (MHC-II-associated invariant chain, amino acids 89-100; 2 μg). The response frequencies were normalized to the response frequencies in the isotype control-treated cultures and the mean+SEM of these normalized response frequencies are shown for each treatment. Note that the responses to the 3 epitopes classified as Type 1 were only blocked with the anti-MHC-I mAb and the 4 epitopes classified as Type 2 were only blocked with the anti-MHC-II mAb and the CLIP peptide.

FIG. 2B is a plot of the number of SIVgag epitopes per RM of the indicated types (MHC-I blocked, MHC-II blocked or indeterminate) resulting from RM immunized as indicated on the X-axis. SIVgag 15mer peptide responses described in FIG. 2A were subjected to MHC-I (mAb w6-32) vs. MHC-II (mAb G46-6) blockade and classified as MHC-I-blocked, MHC-II blocked or indeterminate. For each RM, the average number of peptide specific responses in each category is shown, classified by vaccine type.

FIG. 2C is an epitope map of the responses of CD8+ T cells derived from strain 68.1 RhCMV/gag-vaccinated RM arranged according to whether or not the response is inhibited by MHC-I or MHC-II blockade. The sensitivity of each SIVgag peptide response in 11 strain 68.1 RhCMV/gag-vaccinated RM to MHC-I (red boxes) vs. MHC-II (blue boxes) blockade (open boxes indicate indeterminate) is shown, with the minimal number of independent epitopes in the MHC-I- and MHC-II-associated categories designated at right.

FIG. 3A is a set of FACS plots of PBMC from a RhCMV/gag-vaccinated RM (Rh22034). CMV vectors induce T cells recognizing the same peptide presented by different MHC alelles ("supertopes") were incubated with SIVgag peptide-pulsed (and washed) RM3 cells (MHC-II null parental cell line) vs. RM3 transfectants expressing single Mamu DR molecules, and then evaluated for peptide-specific CD8$^+$ T cell recognition using flow cytometric ICS to detect induction of IFN-γ and/or TNF-α production (response frequencies are indicated in each quadrant). The Mamu DR molecules tested included four that are expressed by Rh22034 (DRB1*0309, DRB1*0406, DRB5*0301, and DRB*w201), and one that is not expressed (DRB*w4:01). The SIVgag 15mer peptides tested corresponded to known MHC-II-blocked CD8+ T cell epitopes in this RM, except for Gag273-287 (15mer #69), which was MHC-I-blocked and therefore used as a negative control.

FIG. 3B is a set of FACS plots of a similar analysis (to FIG. 3A) of the presentation of Gag141-155 (15mer #36) to CD8+ T cells from Rh22034 and Rh21836 by autologousB-lymphoblastoid cells, MHC-II null parental cells and single MHC-II transfectants corresponding to Mamu-DRB alleles that are reciprocally expressed by these 2 RM (expressed alleles denoted in red, non-expressed in black).

FIG. 4A is a plot showing serial $\log_{10}$ dilutions of 4 core (optimal) SIVgag peptides (2 each MHC-I- and MHC-II-restricted), starting at the standard peptide concentration of 2 µg per test. Peptides were used to stimulate PBMC from strain 68.1 RhCMV/gag-vaccinated RM (n=5) and the response to each peptide dilution was determined by flow cytometric ICS. The frequency of responding CD8+ T cells (TNF-α and/or IFN-γ positive) at each dilution was normalized to the response at the standard peptide concentration. The figure shows the mean+SEM of the normalized responses for each epitope.

FIG. 4B is a plot showing peripheral blood CD8+ T cell responses to total SIVgag 15mer mixes and to 4 core (optimal) SIVgag supertope peptides (2 each MHC-I- and MHC-II-restricted). Responses were quantified by flow cytometric ICS following strain 68.1 RhCMV/gag vaccination (mean+SEM; n=24) to demonstrate the relative kinetics of induction of the MHC-I vs. MHC-II-restricted supertope responses.

Figure 4A:
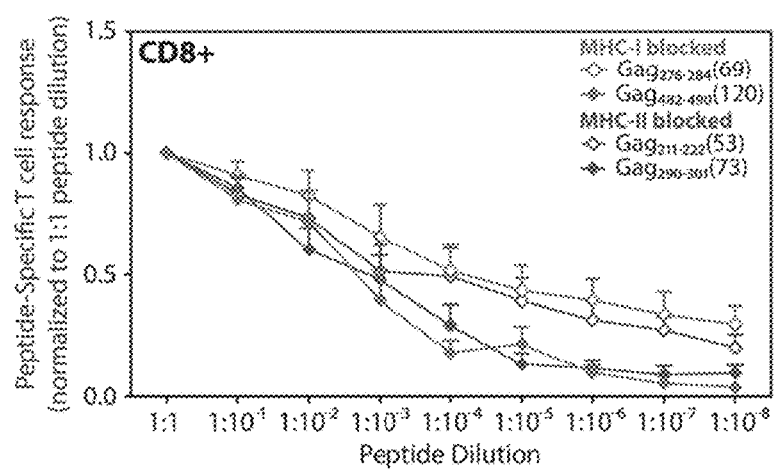
FIG. 4C is a bar graph showing CD8+ T cell responses to 2 MHC-I restricted core (optimal) SIVgag supertope peptides. Responses were quantified by flow cytometric ICS in mononuclear cell preparations from the indicated tissues at necropsy of strain 68.1 RhCMV/gag vector-vaccinated RM (mean+SEM; n=4).
FIG. 4D is a bar graph showing CD8+ T cell responses to 2 MHC-II-restricted core (optimal) SIVgag supertope peptides. Responses were quantified by flow cytometric ICS in mononuclear cell preparations from the indicated tissues at necropsy of strain 68.1 RhCMV/gag vector-vaccinated RM (mean+SEM; n=4).
Figure 4B:
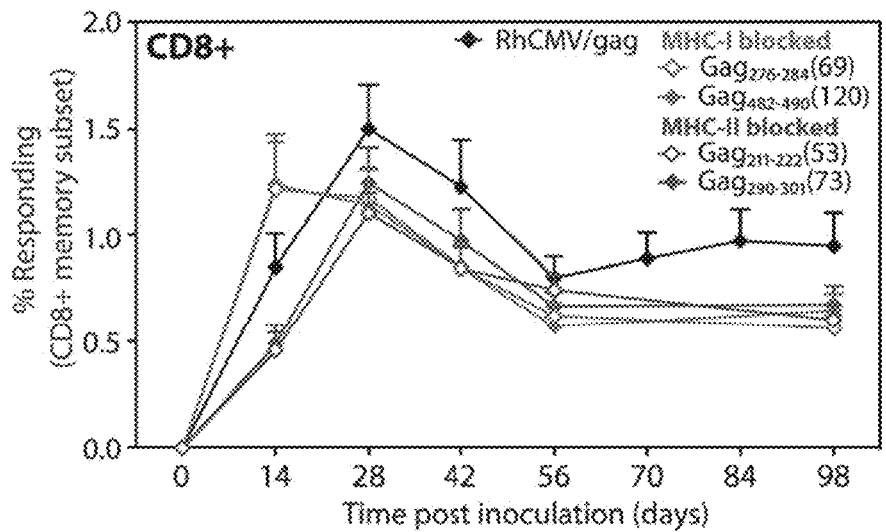
Figure 4C:
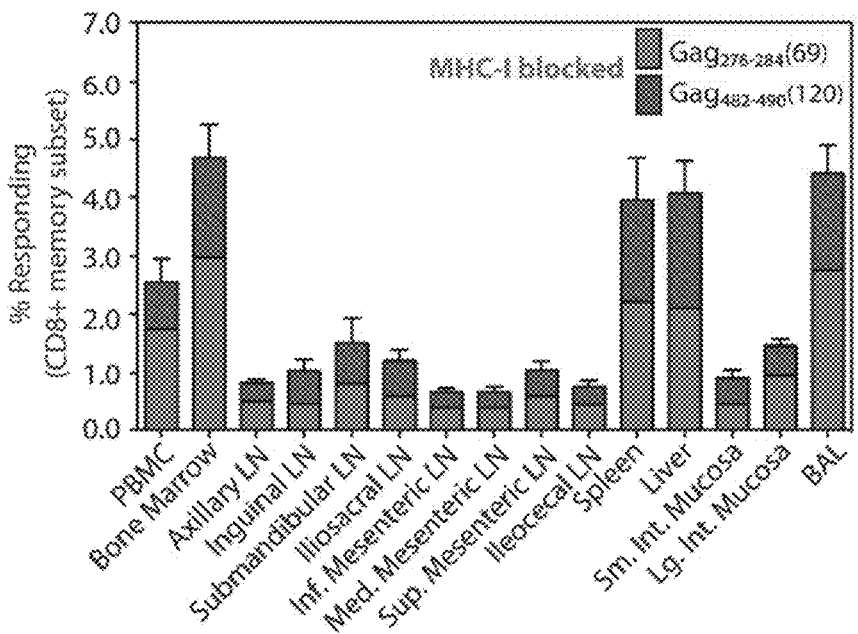
Figure 4D:
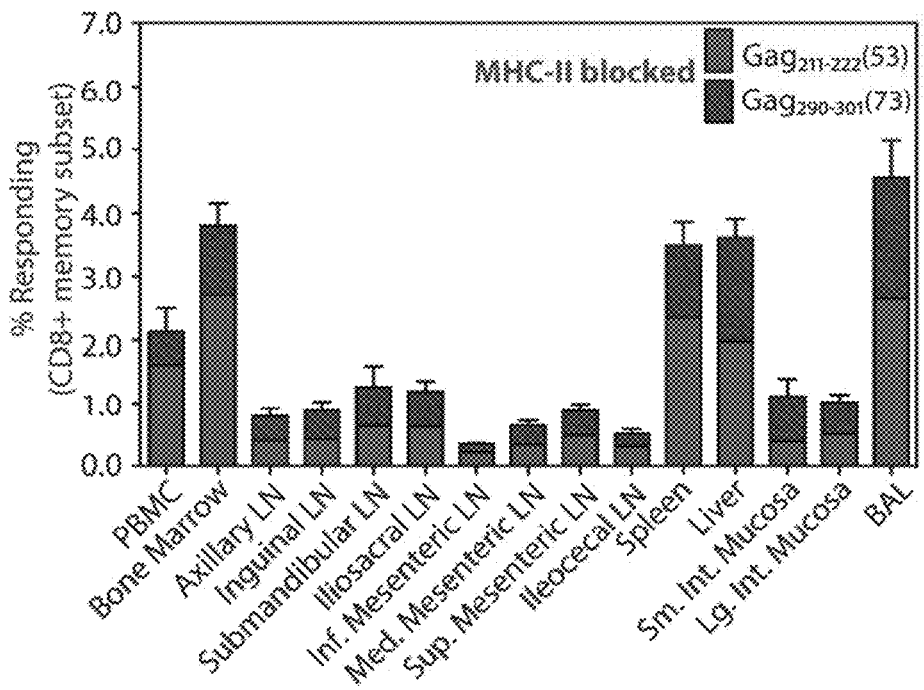
Figure 4E:
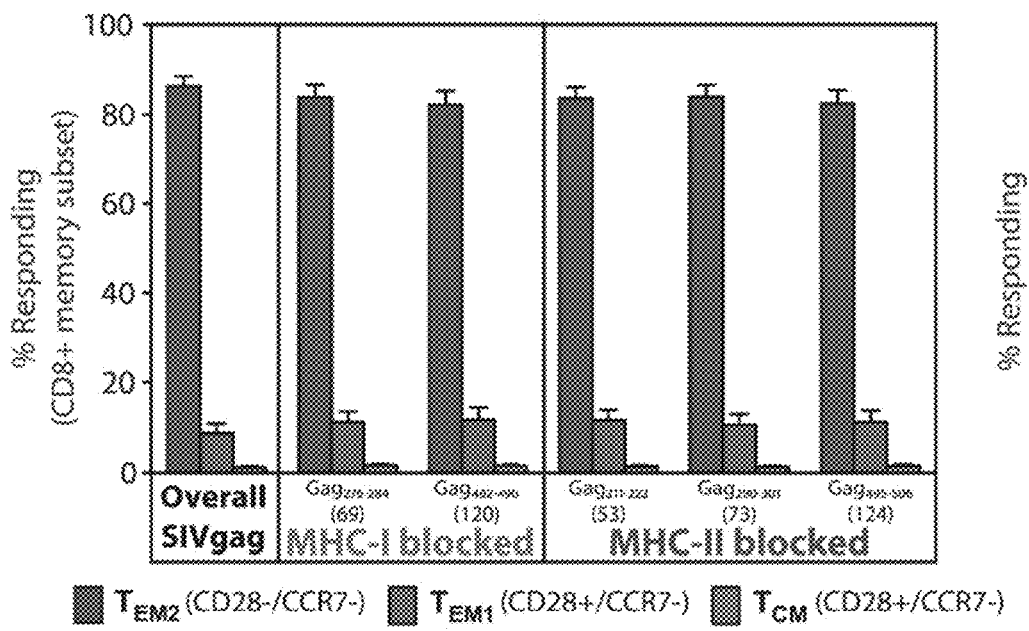

FIG. 4E is a bar graph of the CD8+ T cell responses of PBMC from strain 68.1 RhCMV/gag vaccinated RM (n=14). Cells were stimulated with total SIVgag 15mer mixes or the MHC-I- vs. MHC-II-restricted core (optimal) SIVgag supertope peptides shown and the expression of CD28 vs. CCR7 was determined on the responding cells (TNF-α and/or IFN-γ positive) by flow cytometric ICS, allowing delineation of the mean (±SEM) proportion of the responding cells manifesting the designated TCM/TEM1/TEM2 phenotypes.

Figure 4F:
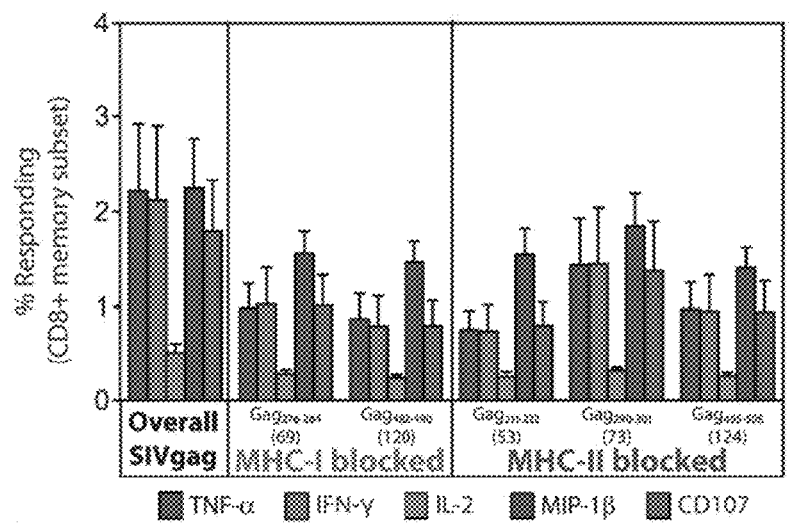

FIG. 4F is a bar graph of CD8+ T cell responses of PBMC from strain 68.1 RhCMV/gag-vaccinated RM (n=14). Cells were stimulated with total SIVgag 15mer mixes or the MHC-I- vs. MHC-II-restricted core (optimal) SIVgag supertope peptides shown (vs. no peptide) and the frequencies of cells within the CD8+ memory compartment producing the designated cytokine or manifesting degranulation (CD107 externalization) were determined. The figure shows the mean (±SEM) of these response frequencies after background subtraction.

Figure 5A:
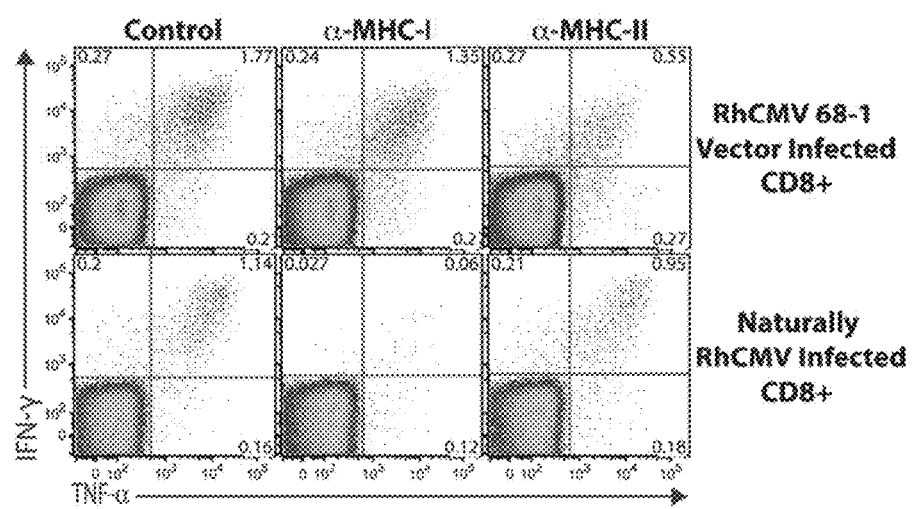

FIG. 5A is a set of representative flow cytometric profiles of CD8+ T cells in PBMC from an unvaccinated, naturally RhCMV-infected RM (colony circulating strain) vs. strain 68.1 RhCMV/SIV vector-vaccinated RM responding to consecutive 15mer peptides (11 amino acid overlap) comprising the RhCMV IE1 protein in the presence of isotype control vs. blocking anti-MHC-I vs. blocking anti-MHC-II mAbs.

Figure 5B:
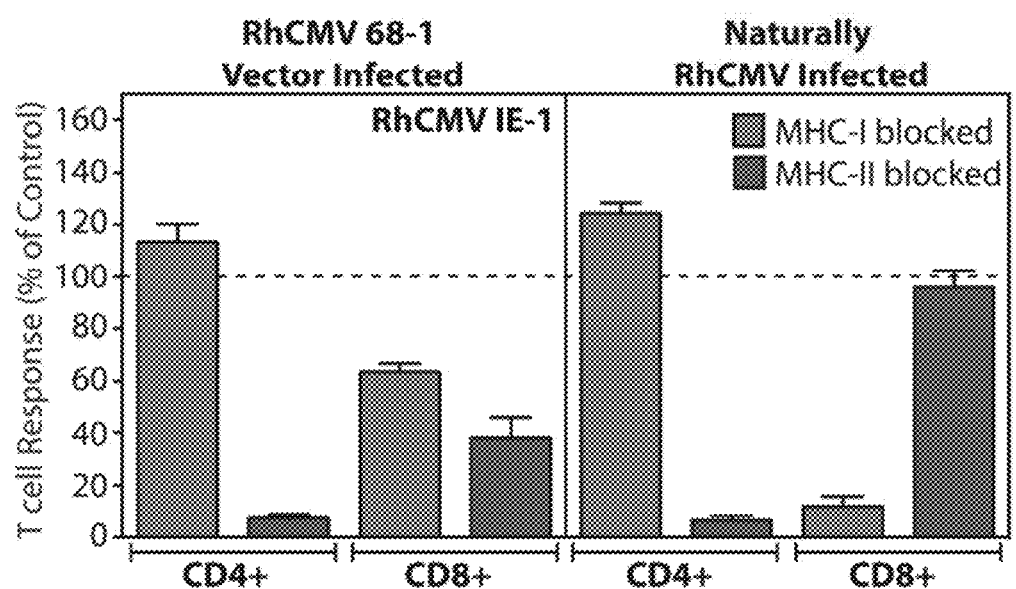

FIG. 5B is a bar graph that compares of the sensitivity of IE1-specific CD4+ and CD8+ T cells from naturally RhCMV-infected or strain 68.1 RhCMV/SIV vector-vaccinated RM (n=4 per group) to blockade with anti-MHC-I vs. anti-MHC-II mAbs.

Figure 5C:
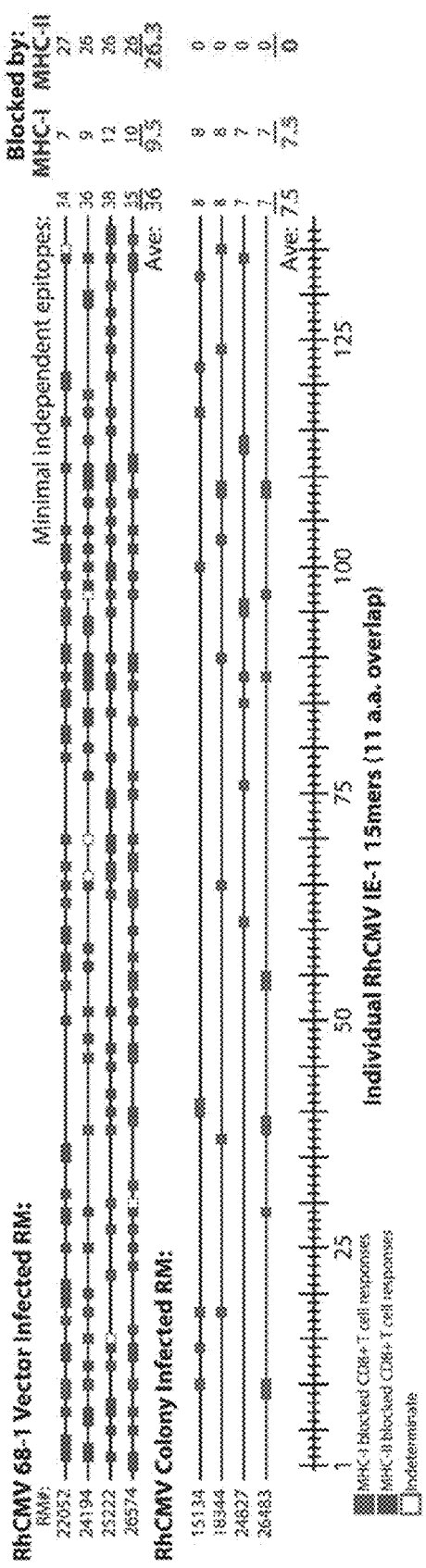

FIG. 5C is an epitope map of CD8+ T cell responses to RhCMV IE1 in naturally RhCMV-infected and strain 68.1 RhCMV/SIV vector-vaccinated RM (n=4 each). Responses were epitope-mapped to determine recognition of 137 consecutive 15mer IE1 peptides and then the MHC association of each response was classified by MHC-I vs. MHC-II blockade.

Figure 5D:
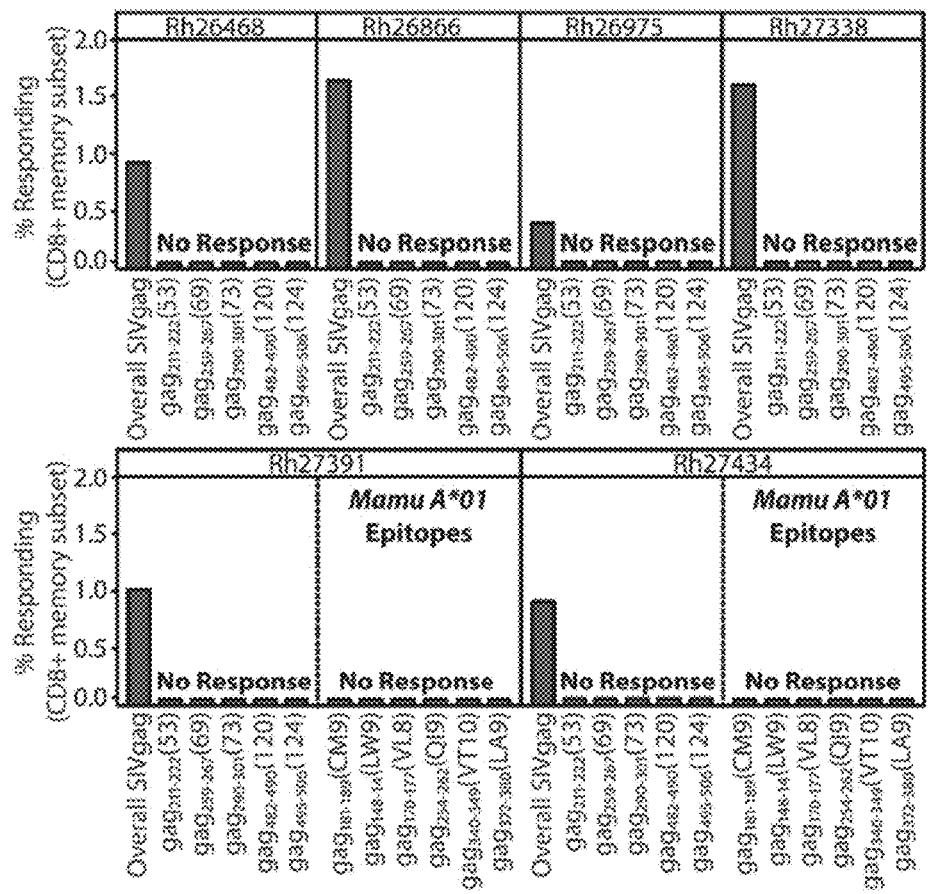

FIG. 5D is a set of bar graphs illustrating the peak acute phase CD8 T cell responses in blood to whole SIVgag 15mer mix, each of the 5 universal RhCMV/gag vector-associated supertopes, and in the 2 Mamu A*01+RM, each of the indicated canonical SIVgag epitopes restricted by this allele. Responses are shown in 6 RM vaccinated with a strain 68.1 RhCMV/gag vector in which expression of RhCMV orthologues of HCMV UL130-128 genes (Rh157.4 and 157.5) has been restored (Repaired RhCMV/gag was derived from RhCMV-68-1.2 as described by Lilja A E and Shenk T, *Proc Natl Acad Sci U S A* 105, 19950-19955 (2008) which is incorporated by reference herein.

Figure 5E:
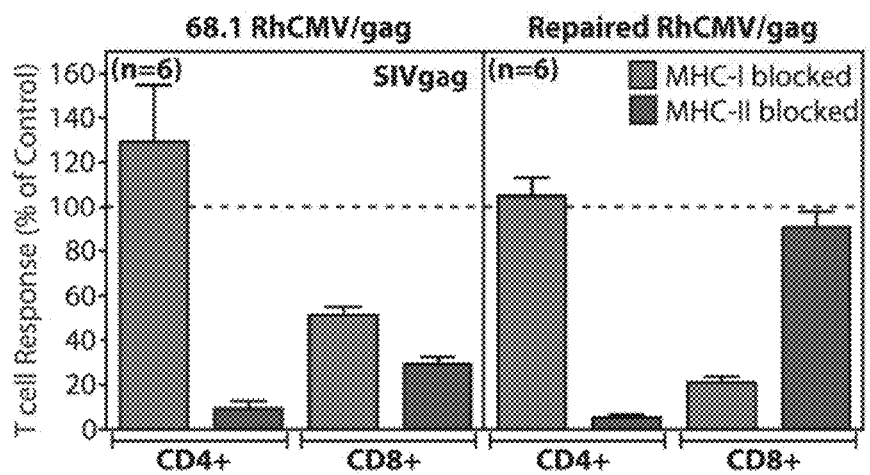

FIG. 5E is a comparison of the sensitivity of SIVgag-specific CD4+ and CD8+ T cells from RM vaccinated with the original strain 68.1 RhCMV/SIV vector vs. the Rh157.4-0.5 (UL128-130)-repaired RhCMV/gag vector (n=6 per group) to blockade with anti-MHC-I vs. anti-MHC-II mAbs.

Figure 5F:
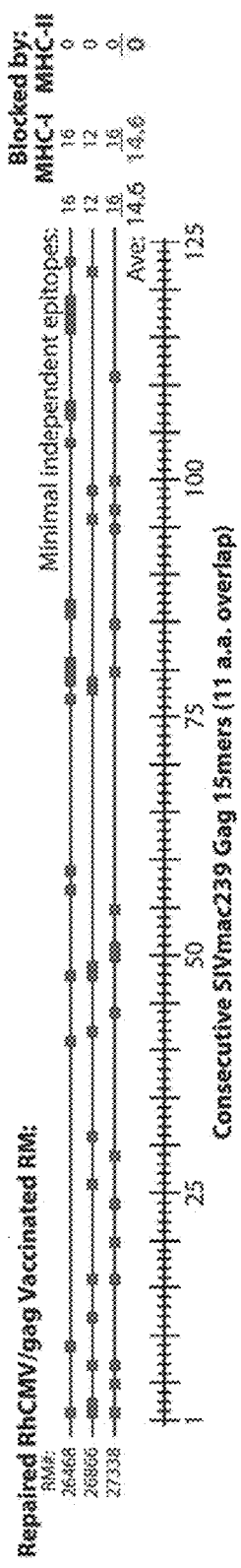

FIG. 5F is a comparison of CD8+ T cell responses to SIVgag in 3 RM vaccinated with the Rh157.4-0.5 (UL130-128)-repaired RhCMV/gag vector. Responses were epitope-mapped and then the MHC association of each response was classified by MHC-I vs. MHC-II blockade. No MHC-II blocked responses were detected.

Figure 6:
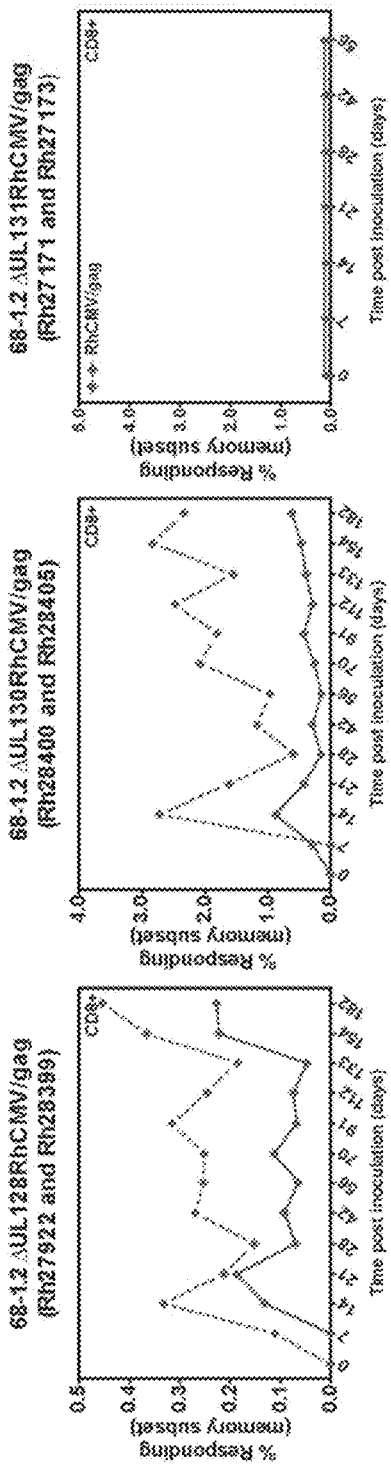

FIG. 6 is a set of three plots showing the percent SIVgag-specific CD8+ T cell responses in the memory T cell subset for two RM vaccinated with a vector lacking UL128, but with an active UL130 and UL131 (left); a vector lacking UL130 but with an active UL128 and UL131 (center); and a vector with an active UL128 and an active UL130 but lacking an active UL131 (right). The vector lacking UL131, but with UL128 and UL130 did not result in any CD8+ immune response (FIG. 6, right).

Figure 1A:
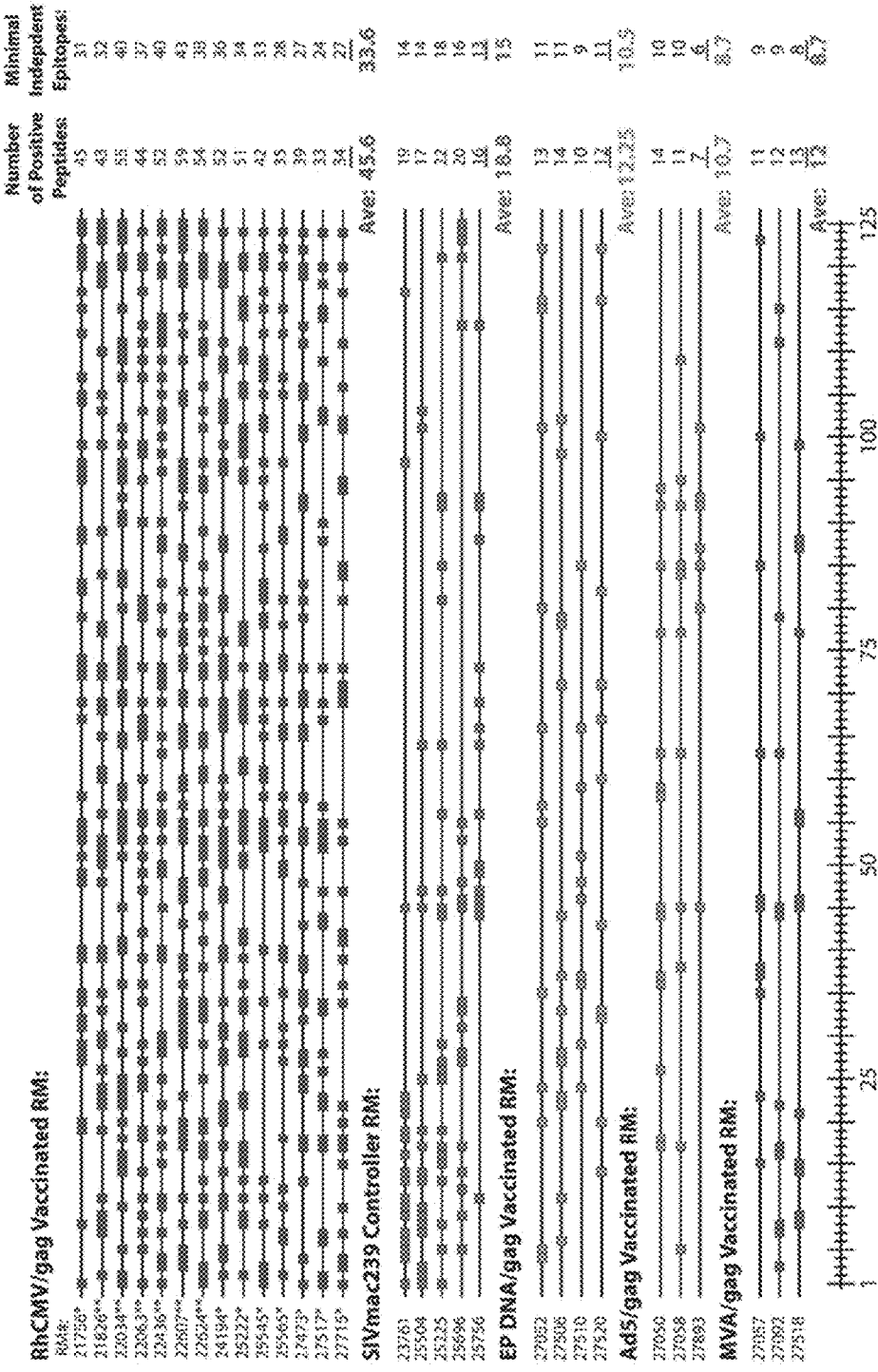
Figure 2A:
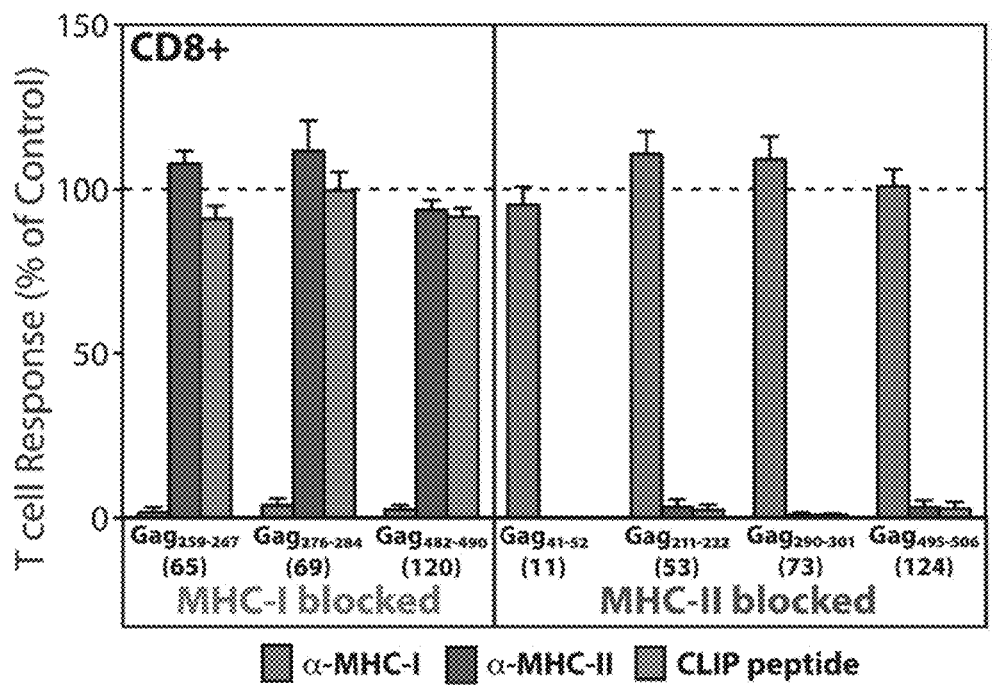
Figure 2B:
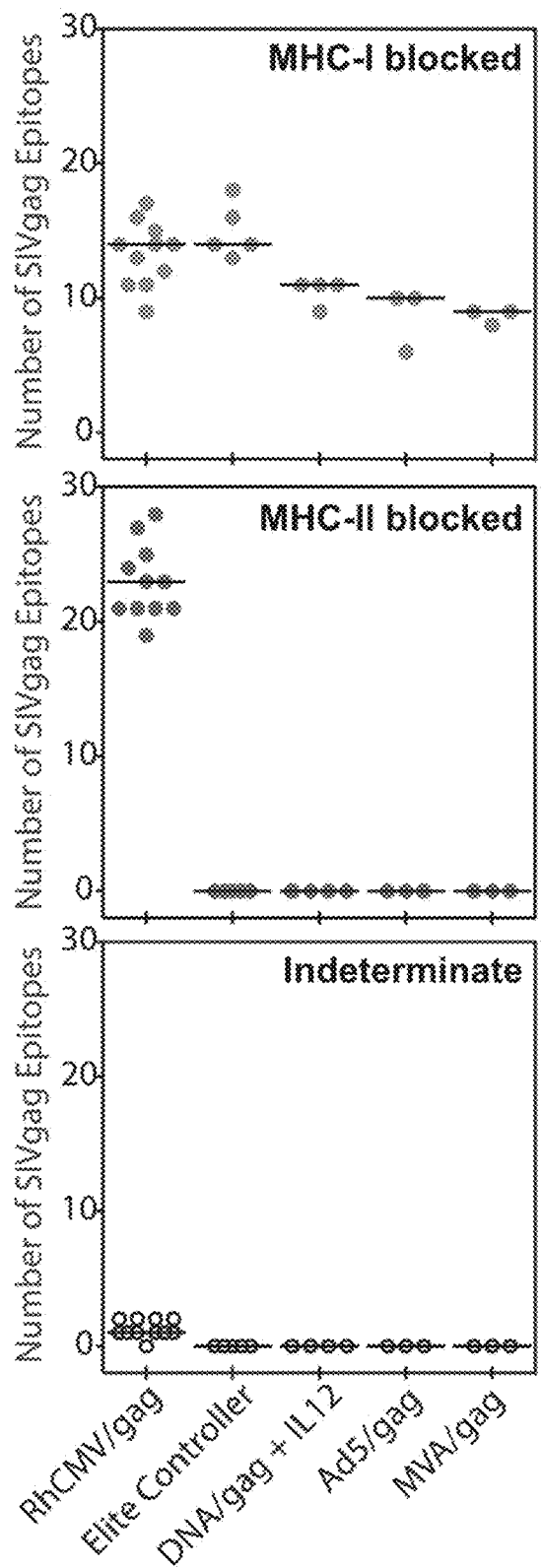
Figure 2C:
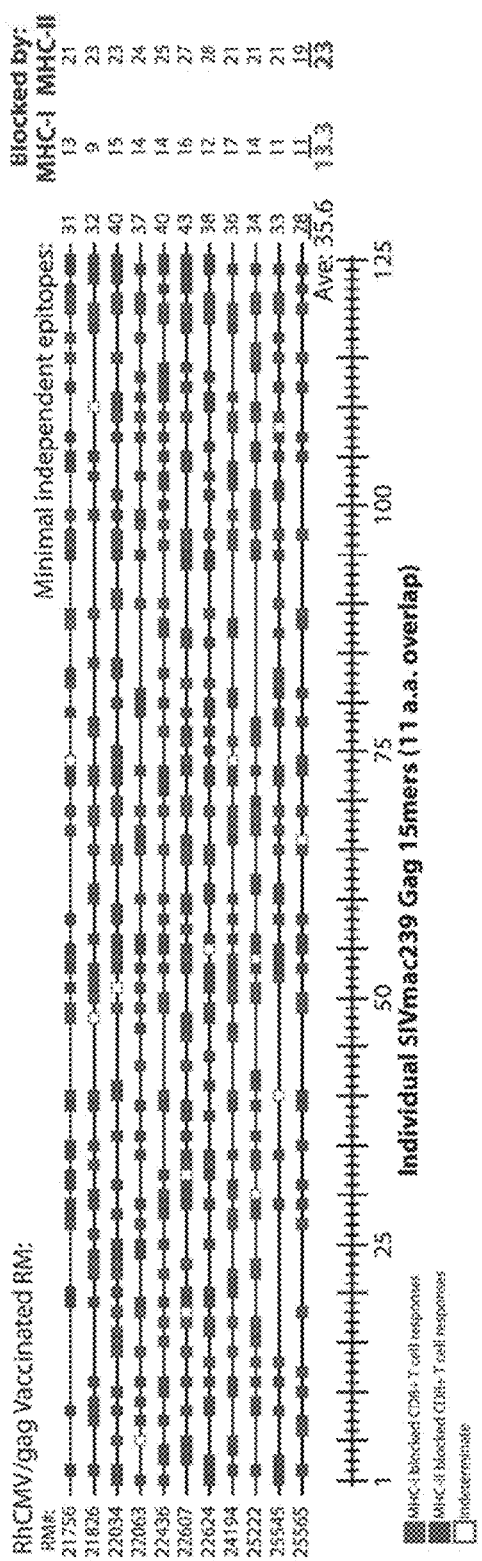
Figure 7:
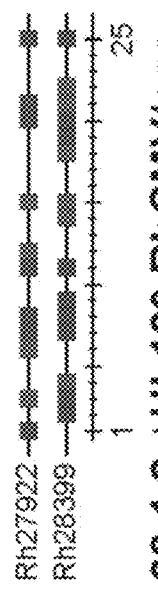
Figure 7:
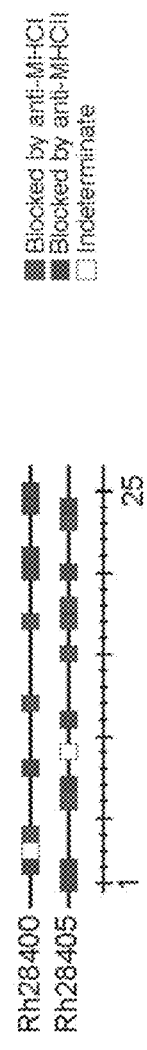

FIG. 7 is a set of two epitope maps similar to FIGS. 1A, 2C, and 5C above showing the CD8+ T cell response to individual peptides within a set of about 25 overlapping 15mer corresponding to the amino-terminal portion of SIVgag in PBMC from two RM vaccinated with an RhCMVgag vector lacking UL128 (but with an active UL130 and UL131) or an RhCMVgag vector lacking UL130 (but with an active UL128 and UL131). To determine whether peptides were presented by MHC class I or MHC class II, T cell stimulation was performed in the presence of MHC-I or MHC-II-specific antibodies. CD8+ T cell responses that were inhibited by MHC-I or MHC-II specific antibodies are shown in red or blue, respectively. These results show that vectors lacking either UL128 or UL130 induce MHC-II restricted CD8+ T cells.

Figure 8:
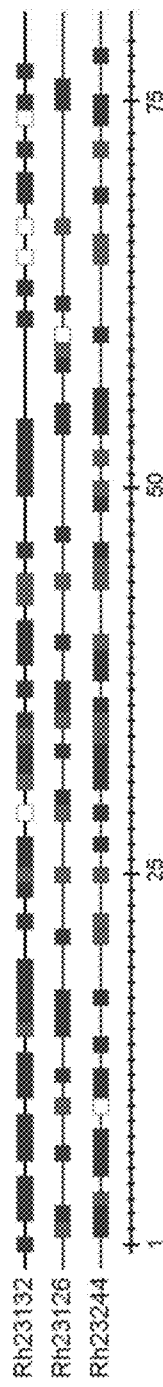
Figure 8:
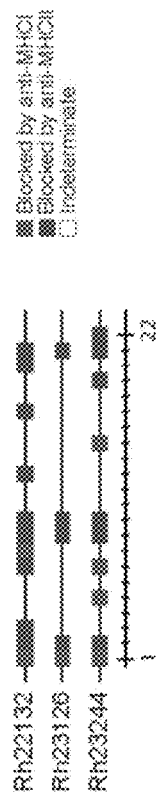

FIG. 8 is a set of two epitope maps showing the CD8+ T cell response in the presence of MHC-I or MHC-II blocking antibodies to individual peptides within a set of 75 overlapping 15mer peptides corresponding to Ag85B and 22 overlapping 15mers corresponding to ESAT-6 in PBMC from three RM immunized with ΔUL128-UL130 (68-1) RhCMV vectors comprising the *Mycobacterium tuberculosis* antigens Ag85B and ESAT-6. The results show that RhCMV vectors are capable of inducing MHC-II-restricted CD8+ T cells to bacterial antigens.

Figure 9:
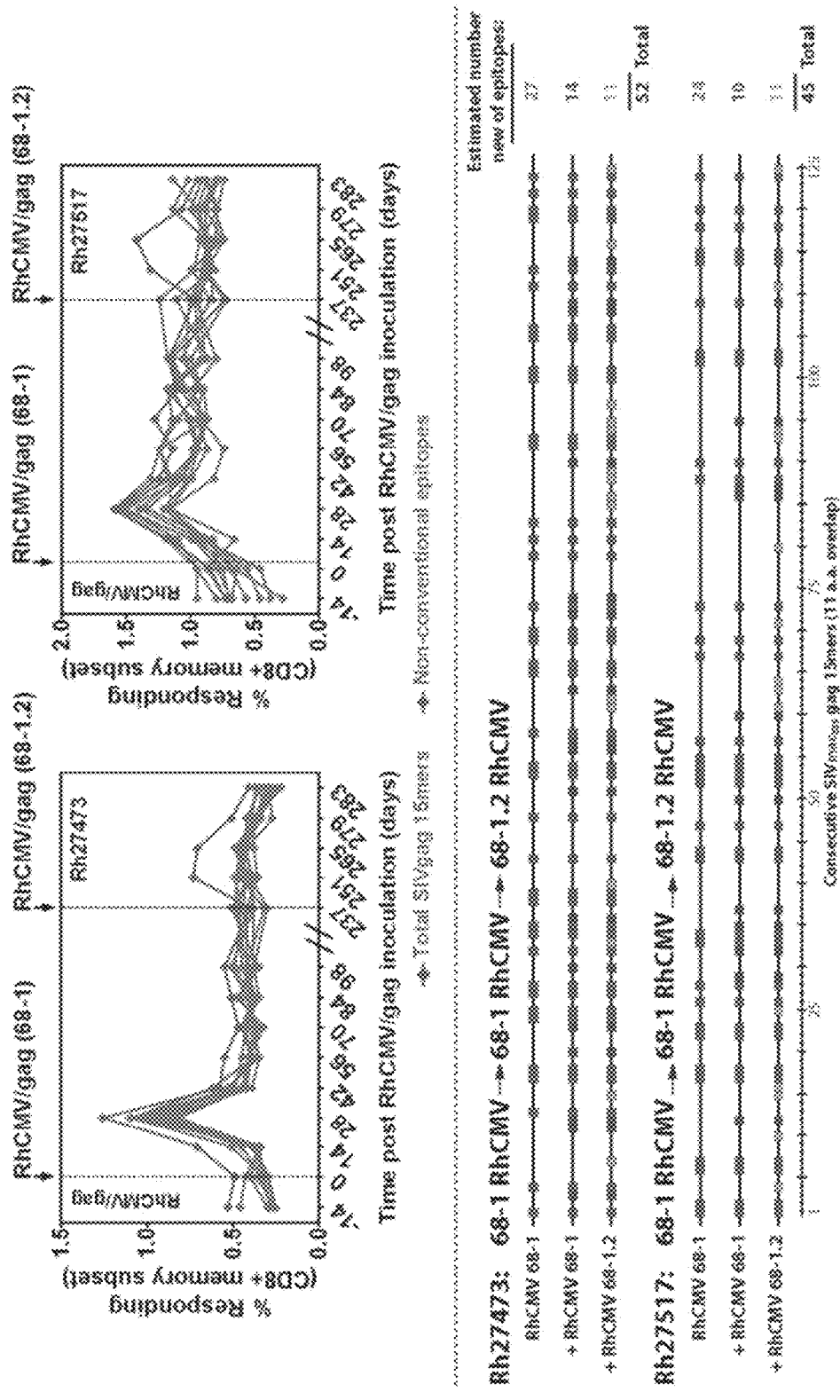

FIG. 9 demonstrates that sequential inoculation with a RhCMV/gag vector lacking UL128 and UL130 (68-1) and a repaired RhCMV/gag vector containing active UL128 and UL130 (68-1.2) increases epitope coverage of a heterologous antigen (SIVgag). The top panel shows the frequency, over time, of SIVgag-specific CD8+ T cells present in the T cell memory pool of two RM previously (<1 year prior) vaccinated RhCMV/SIVgag (68-1) and re-vaccinated with RhCMV/SIVgag (68-1) on day 1 and then vaccinated on day 237 with RhCMV/SIVgag (68-1.2). SIVgag-specific responses were measured by flow cytometry of ICS using a pool of overlapping 15mer peptides (green line) or individual peptides (red lines). Note that the total CD8+ T cell response to SIVgag increased upon re-vaccination with both the 68-1-derived vector and the 68-1.2-derived vector whereas the CD8+ T cell response to individual peptides was not boosted by the 68-1.2-derived vector indicating that the increase in total responses was due to the 68-1.2 vectors eliciting T cells to novel SIVgag peptides. This conclusion is supported by the results shown in the lower panel. Shown is the position of individual 15mer peptides along the SIVgag sequence that are recognized by T cells from each of the two RM inoculated with RhCMV/SIVgag either after the first vaccination with RhCMV/SIVgag(68-1), after re-vaccination with RhCMV/SIVgag(68-1), and after vaccination with RhCMV/SIVgag(68-1.2). Each vaccination elicited additional T cells recognizing new epitopes while previous immune responses were maintained: New epitopes recognized by T cells after re-vaccination with 68-1-derived vectors are shown in blue whereas new epitopes recognized after vaccination with 68-1.2 derived vectors are shown in green. Since these T cell responses are additive, T cell responses to 52 and 45 of the 125 overlapping peptides were measured upon sequential vaccination thus nearly doubling the coverage of SIVgag-derived peptides by T cells compared to single vaccination.

DETAILED DESCRIPTION

Disclosed herein are human or animal cytomegalovirus (CMV) vectors capable of repeatedly infecting an organism. The CMV vectors comprise a nucleic acid sequence that encodes a heterologous protein antigen and a nucleic acid sequence that encodes an active UL131 protein. In one example, the CMV vector comprises a nucleic acid sequence that expresses an active UL128 protein but does not express an active UL130 protein. In another example, the CMV vector encodes an active UL130 protein but does not express an active UL128 protein.

In some examples, the vector does not express an active UL128 or UL130 protein due to the presence of a deleterious mutation in the nucleic acid sequence encoding UL128 or UL130 or their orthologous genes in animal CMVs. The mutation may be any deleterious mutation that results in a lack of expression of active UL128 or UL130 protein. Such mutations can include point mutations, frameshift mutations, deletions of less than all of the sequence that encodes the protein (truncation mutations), or deletions of all of the nucleic acid sequence that encodes the protein, or any other mutations.

In further examples, the vector does not express an active UL128 or UL130 protein due to the presence of a nucleic acid sequence in the vector that comprises an antisense or RNAi sequence (siRNA or miRNA) that inhibits the expression of the UL128 or UL130 protein.

Also disclosed herein are methods of generating CD8+ T cell responses to heterologous antigens in a subject. The methods involve administering an effective amount of a CMV vector to the subject. The CMV vector is characterized by having a nucleic acid sequence that encodes a heterologous antigen and a nucleic acid sequence that encodes an active UL131 protein. The CMV vector is further characterized by not encoding an active UL128 protein or an active UL130 protein or neither an active UL128 or active UL130 protein. The CD8+ T cell response is further characterized by having at least 10% of the CD8+ T cells directed against epitopes presented by MHC class II. In further examples, at least 20%, at least 30%, at least 40%, at least 50%, at least 60%, or more than 60% of the CD8+ T cells are directed against epitopes presented by MHC class II.

In further examples, the methods involve administering an effective amount of a second CMV vector, the second CMV vector comprising a nucleic acid sequence that encodes a heterologous antigen to the subject. This second vector can be any CMV vector, including a CMV vector with an active UL128 and an active UL130 protein. The second CMV vector may comprise additional deletions known in the art to provide different immune responses such as a US11 deletion or any other deletion. The second heterologous antigen can be any heterologous antigen, including a heterologous antigen identical to the heterologous antigen in the first CMV vector. The second CMV vector can be administered at any time relative to the administration of the first CMV vector including before, concurrently with, or after the administration of the first CMV vector. This includes administration of the second vector any number of months, days, hours, minutes or seconds before or after the first vector.

Human or animal CMV vectors, when used as expression vectors are innately non-pathogenic in the selected subjects such as humans or have been modified to render them non-pathogenic in the selected subjects. For example, replication-defective adenoviruses and alphaviruses are well known and can be used as gene delivery vectors.

The heterologous antigen can be any protein or fragment thereof that is not derived from CMV, including cancer antigens, pathogen specific antigens, model antigens (such as lysozyme or ovalbumin), or any other antigen.

Pathogen specific antigens can be derived from any human or animal pathogen. The pathogen may be a viral pathogen and the antigen may be a protein derived from the viral pathogen. Viruses include, but are not limited to Adenovirus, coxsackievirus, hepatitis A virus, poliovirus, rhinovirus, Herpes simplex, type 1, Herpes simplex, type 2, Varicella-zoster virus, Epstein-Barr virus, Kaposi's sarcoma herpesvirus, Human cytomegalovirus, Human herpesvirus, type 8, Hepatitis B virus, Hepatitis C virus, yellow fever virus, dengue virus, West Nile virus, Human immunodeficiency virus (HIV), Influenza virus, Measles virus, Mumps virus, Parainfluenza virus, Respiratory syncytial virus, Human metapneumovirus, Human papillomavirus, Rabies virus, Rubella virus, Human bocavirus and Parvovirus B19.

The pathogen may be a bacterial pathogen and the antigen may be a protein derived from the bacterial pathogen. The pathogenic bacteria include, but are not limited to, *Borde-* tella pertussis, Borrelia burgdorferi, Brucella abortus, Brucella canis, Brucella melitensis, Brucella suis, Campylobacter jejuni, Chlamydia pneumoniae, Chlamydia trachomatis, Chlamydophila psittaci, Clostridium botulinum, Clostridium difficile, Clostridium perfringens, Clostridium tetani, Corynebacterium diphtheriae, Enterococcus faecalis, Enterococcus faecium, Escherichia coli, Francisella tularensis, Haemophilus influenzae, Helicobacter pylori, Legionella pneumophila, Leptospira interrogans, Listeria monocytogenes, Mycobacterium leprae, Mycobacterium tuberculosis, Mycobacterium ulcerans, Mycoplasma pneumoniae, Neisseria gonorrhoeae, Neisseria meningitidis, Pseudomonas aeruginosa, Rickettsia rickettsii, Salmonella typhi, Salmonella typhimurium, Shigella sonnei, Staphylococcus aureus, Staphylococcus epidermidis, Staphylococcus saprophyticus, Streptococcus agalactiae, Streptococcus pneumoniae, Streptococcus pyogenes, Treponema pallidum, Vibrio cholera and Yersinia pestis.

The pathogen may be a parasite and the antigen may be a protein derived from the parasite pathogen. The parasite may be a protozoan organism or a protozoan organism causing a disease such as, but not limited to, Acanthamoeba, Babesiosis, Balantidiasis, Blastocystosis, Coccidia, Dientamoebiasis, Amoebiasis, Giardia, Isosporiasis, Leishmaniasis, Primary amoebic meningoencephalitis (PAM), Malaria, Rhinosporidiosis, Toxoplasmosis-Parasitic pneumonia, Trichomoniasis, Sleeping sickness and Chagas disease. The parasite may be a helminth organism or worm or a disease caused by a helminth organism such as, but not limited to, Ancylostomiasis/Hookworm, Anisakiasis, Roundworm—Parasitic pneumonia, Roundworm—Baylisascariasis, Tapeworm—Tapeworm infection, Clonorchiasis, Dioctophyme renalis infection, Diphyllobothriasis—tapeworm, Guinea worm—Dracunculiasis, Echinococcosis—tapeworm, Pinworm—Enterobiasis, Liver fluke—Fasciolosis, Fasciolopsiasis—intestinal fluke, Gnathostomiasis, Hymenolepiasis, Loa loa filariasis, Calabar swellings, Mansonelliasis, Filariasis, Metagonimiasis—intestinal fluke, River blindness, Chinese Liver Fluke, Paragonimiasis, Lung Fluke, Schistosomiasis—bilharzia, bilharziosis or snail fever (all types), intestinal schistosomiasis, urinary schistosomiasis, Schistosomiasis by Schistosoma japonicum, Asian intestinal schistosomiasis, Sparganosis, Strongyloidiasis—Parasitic pneumonia, Beef tapeworm, Pork tapeworm, Toxocariasis, Trichinosis, Swimmer's itch, Whipworm and Elephantiasis Lymphatic filariasis. The parasite may be an organism or disease caused by an organism such as, but not limited to, parasitic worm, Halzoun Syndrome, Myiasis, Chigoe flea, Human Botfly and Candiru. The parasite may be an ectoparasite or disease caused by an ectoparasite such as, but not limited to, Bedbug, Head louse—Pediculosis, Body louse—Pediculosis, Crab louse—Pediculosis, Demodex—Demodicosis, Scabies, Screwworm and Cochliomyia.

The antigen may be a protein derived from cancer. The cancers, include, but are not limited to, Acute lymphoblastic leukemia; Acute myeloid leukemia; Adrenocortical carcinoma; AIDS-related cancers; AIDS-related lymphoma; Anal cancer; Appendix cancer; Astrocytoma, childhood cerebellar or cerebral; Basal cell carcinoma; Bile duct cancer, extrahepatic; Bladder cancer; Bone cancer, Osteosarcoma/Malignant fibrous histiocytoma; Brainstem glioma; Brain tumor; Brain tumor, cerebellar astrocytoma; Brain tumor, cerebral astrocytoma/malignant glioma; Brain tumor, ependymoma; Brain tumor, medulloblastoma; Brain tumor, supratentorial primitive neuroectodermal tumors; Brain tumor, visual pathway and hypothalamic glioma; Breast cancer; Bronchial adenomas/carcinoids; Burkitt lymphoma; Carcinoid tumor, childhood; Carcinoid tumor, gastrointestinal; Carcinoma of unknown primary; Central nervous system lymphoma, primary; Cerebellar astrocytoma, childhood; Cerebral astrocytoma/Malignant glioma, childhood; Cervical cancer; Childhood cancers; Chronic lymphocytic leukemia; Chronic myelogenous leukemia; Chronic myeloproliferative disorders; Colon Cancer; Cutaneous T-cell lymphoma; Desmoplastic small round cell tumor; Endometrial cancer; Ependymoma; Esophageal cancer; Ewing's sarcoma in the Ewing family of tumors; Extracranial germ cell tumor, Childhood; Extragonadal Germ cell tumor; Extrahepatic bile duct cancer; Eye Cancer, Intraocular melanoma; Eye Cancer, Retinoblastoma; Gallbladder cancer; Gastric (Stomach) cancer; Gastrointestinal Carcinoid Tumor; Gastrointestinal stromal tumor (GIST); Germ cell tumor: extracranial, extragonadal, or ovarian; Gestational trophoblastic tumor; Glioma of the brain stem; Glioma, Childhood Cerebral Astrocytoma; Glioma, Childhood Visual Pathway and Hypothalamic; Gastric carcinoid; Hairy cell leukemia; Head and neck cancer; Heart cancer; Hepatocellular (liver) cancer; Hodgkin lymphoma; Hypopharyngeal cancer; Hypothalamic and visual pathway glioma, childhood; Intraocular Melanoma; Islet Cell Carcinoma (Endocrine Pancreas); Kaposi sarcoma; Kidney cancer (renal cell cancer); Laryngeal Cancer; Leukemias; Leukemia, acute lymphoblastic (also called acute lymphocytic leukemia); Leukemia, acute myeloid (also called acute myelogenous leukemia); Leukemia, chronic lymphocytic (also called chronic lymphocytic leukemia); Leukemia, chronic myelogenous (also called chronic myeloid leukemia); Leukemia, hairy cell; Lip and Oral Cavity Cancer; Liver Cancer (Primary); Lung Cancer, Non-Small Cell; Lung Cancer, Small Cell; Lymphomas; Lymphoma, AIDS-related; Lymphoma, Burkitt; Lymphoma, cutaneous T-Cell; Lymphoma, Hodgkin; Lymphomas, Non-Hodgkin (an old classification of all lymphomas except Hodgkin's); Lymphoma, Primary Central Nervous System; Marcus Whittle, Deadly Disease; Macroglobulinemia, Waldenstrim; Malignant Fibrous Histiocytoma of Bone/Osteosarcoma; Medulloblastoma, Childhood; Melanoma; Melanoma, Intraocular (Eye); Merkel Cell Carcinoma; Mesothelioma, Adult Malignant; Mesothelioma, Childhood; Metastatic Squamous Neck Cancer with Occult Primary; Mouth Cancer; Multiple Endocrine Neoplasia Syndrome, Childhood; Multiple Myeloma/Plasma Cell Neoplasm; Mycosis Fungoides; Myelodysplastic Syndromes; Myelodysplastic/Myeloproliferative Diseases; Myelogenous Leukemia, Chronic; Myeloid Leukemia, Adult Acute; Myeloid Leukemia, Childhood Acute; Myeloma, Multiple (Cancer of the Bone-Marrow); Myeloproliferative Disorders, Chronic; Nasal cavity and paranasal sinus cancer; Nasopharyngeal carcinoma; Neuroblastoma; Non-Hodgkin lymphoma; Non-small cell lung cancer; Oral Cancer; Oropharyngeal cancer; Osteosarcoma/malignant fibrous histiocytoma of bone; Ovarian cancer; Ovarian epithelial cancer (Surface epithelial-stromal tumor); Ovarian germ cell tumor; Ovarian low malignant potential tumor; Pancreatic cancer; Pancreatic cancer, islet cell; Paranasal sinus and nasal cavity cancer; Parathyroid cancer; Penile cancer; Pharyngeal cancer; Pheochromocytoma; Pineal astrocytoma; Pineal germinoma; Pineoblastoma and supratentorial primitive neuroectodermal tumors, childhood; Pituitary adenoma; Plasma cell neoplasia/Multiple myeloma; Pleuropulmonary blastoma; Primary central nervous system lymphoma; Prostate cancer; Rectal cancer; Renal cell carcinoma (kidney cancer); Renal pelvis and ureter, transitional cell cancer; Retinoblastoma; Rhabdomyosarcoma, childhood; Salivary gland cancer; Sarcoma, Ewing family of tumors; Sarcoma, Kaposi; Sarcoma, soft tissue; Sarcoma, uterine; Sezary syndrome; Skin cancer (nonmelanoma); Skin cancer (melanoma); Skin carcinoma, Merkel cell; Small cell lung cancer; Small intestine cancer; Soft tissue sarcoma; Squamous cell carcinoma—see Skin cancer (nonmelanoma); Squamous neck cancer with occult primary, metastatic; Stomach cancer; Supratentorial primitive neuroectodermal tumor, childhood; T-Cell lymphoma, cutaneous (Mycosis Fungoides and Sezary syndrome); Testicular cancer; Throat cancer; Thymoma, childhood; Thymoma and Thymic carcinoma; Thyroid cancer; Thyroid cancer, childhood; Transitional cell cancer of the renal pelvis and ureter; Trophoblastic tumor, gestational; Unknown primary site, carcinoma of, adult; Unknown primary site, cancer of, childhood; Ureter and renal pelvis, transitional cell cancer; Urethral cancer; Uterine cancer, endometrial; Uterine sarcoma; Vaginal cancer; Visual pathway and hypothalamic glioma, childhood; Vulvar cancer; Waldenstrm macroglobulinemia and Wilms tumor (kidney cancer.)

The CMV vectors described herein provide a vector for cloning or expression of heterologous DNA comprising recombinant human or animal CMV. The heterologous DNA may encode an expression product comprising: an epitope of interest, a biological response modulator, a growth factor, a recognition sequence, a therapeutic gene, or a fusion protein.

The CMV vectors disclosed herein can be used as an immunogenic, immunological or vaccine composition containing the recombinant CMV virus or vector, and a pharmaceutically acceptable carrier or diluent. An immunological composition containing the recombinant CMV virus or vector (or an expression product thereof) elicits an immunological response—local or systemic. The response can, but need not be, protective. An immunogenic composition containing the recombinant CMV virus or vector (or an expression product thereof) likewise elicits a local or systemic immunological response which can, but need not be, protective. A vaccine composition elicits a local or systemic protective response. Accordingly, the terms "immunological composition" and "immunogenic composition" include a "vaccine composition" (as the two former terms can be protective compositions).

The CMV vectors disclosed herein provide methods of inducing an immunological response in a subject comprising administering to the subject an immunogenic, immunological or vaccine composition comprising the recombinant CMV virus or vector and a pharmaceutically acceptable carrier or diluent. For purposes of this specification, the term "subject" includes all animals, including non-human primates and humans, while "animal" includes all vertebrate species, except humans; and "vertebrate" includes all vertebrates, including animals (as "animal" is used herein) and humans. And, of course, a subset of "animal" is "mammal", which for purposes of this specification includes all mammals, except humans.

The CMV vectors disclosed herein can be used in therapeutic compositions containing the recombinant CMV virus or vector and a pharmaceutically acceptable carrier or diluent. The therapeutic composition is useful in the gene therapy and immunotherapy embodiments of the invention, e.g., in a method for transferring genetic information to an animal or human in need of such comprising administering to the host the composition; and, the invention accordingly includes methods for transferring genetic information.

The CMV vectors disclosed herein can be used in a method of expressing a protein or gene product or an expression product which comprises infecting or transfecting a cell in vitro with a recombinant CMV virus or vector of the invention and optionally extracting, purifying or isolating the protein, gene product or expression product or DNA from the cell. And, the invention provides a method for cloning or replicating a heterologous DNA sequence comprising infecting or transfecting a cell in vitro or in vivo with a recombinant CMV virus or vector of the invention and optionally extracting, purifying or isolating the DNA from the cell or progeny virus.

The CMV vectors disclosed herein can be prepared by inserting DNA comprising a sequence that encodes the heterologous antigen into a non-essential region of the CMV genome. The method can further comprise deleting one or more regions from the CMV genome. The method can comprise in vivo recombination. Thus, the method can comprise transfecting a cell with CMV DNA in a cell-compatible medium in the presence of donor DNA comprising the heterologous DNA flanked by DNA sequences homologous with portions of the CMV genome, whereby the heterologous DNA is introduced into the genome of the CMV, and optionally then recovering CMV modified by the in vivo recombination. The method can also comprise cleaving CMV DNA to obtain cleaved CMV DNA, ligating the heterologous DNA to the cleaved CMV DNA to obtain hybrid CMV-heterologous DNA, transfecting a cell with the hybrid CMV-heterologous DNA, and optionally then recovering CMV modified by the presence of the heterologous DNA. Since in vivo recombination is comprehended, the method accordingly also provides a plasmid comprising donor DNA not naturally occurring in CMV encoding a polypeptide foreign to CMV, the donor DNA is within a segment of CMV DNA that would otherwise be co-linear with a non-essential region of the CMV genome such that DNA from a non-essential region of CMV is flanking the donor DNA. The heterologous DNA can be inserted into CMV to generate the recombinant CMV in any orientation that yields stable integration of that DNA, and expression thereof, when desired.

The DNA encoding the heterologous antigen in the recombinant CMV vector can also include a promoter. The promoter can be from any source such as a herpes virus, including an endogenous cytomegalovirus (CMV) promoter, such as a human CMV (HCMV), rhesus macaque CMV (RhCMV), murine, or other CMV promoter. The promoter can also be a non-viral promoter such as the EF1α promoter. The promoter can be a truncated transcriptionally active promoter which comprises a region transactivated with a transactivating protein provided by the virus and the minimal promoter region of the full-length promoter from which the truncated transcriptionally active promoter is derived. For purposes of this specification, a promoter is composed of an association of DNA sequences corresponding to the minimal promoter and upstream regulatory sequences. A minimal promoter is composed of the CAP site plus TATA box (minimum sequences for basic level of transcription; unregulated level of transcription); and, "upstream regulatory sequences" are composed of the upstream element(s) and enhancer sequence(s). Further, the term "truncated" indicates that the full-length promoter is not completely present, i.e., that some portion of the full-length promoter has been removed. And, the truncated promoter can be derived from a herpesvirus such as MCMV or HCMV, e.g., HCMV-IE or MCMV-IE.

Like the aforementioned promoter, the inventive promoter can be a herpesvirus, e.g., a MCMV or HCMV such as MCMV-IE or HCMV-IE promoter; and, there can be up to a 40% and even up to a 90% reduction in size, from a full-length promoter, based upon base pairs. The promoter can also be a modified non-viral promoter.

Also disclosed is an expression cassette that can be inserted into a recombinant virus or plasmid comprising the truncated transcriptionally active promoter. The expression cassette can further include a functional truncated polyadenylation signal; for instance an SV40 polyadenylation signal which is truncated, yet functional. Considering that nature provided a larger signal, it is indeed surprising that a truncated polyadenylation signal is functional; and, a truncated polyadenylation signal addresses the insert size limit problems of recombinant viruses such as CMV. The expression cassette can also include heterologous DNA with respect to the virus or system into which it is inserted; and that DNA can be heterologous DNA as described herein.

In a more specific aspect, the present invention encompasses CMV, recombinants comprising viral or non-viral promoters, and a truncated promoter therefrom. The invention further comprehends antibodies elicited by the inventive compositions and/or recombinants and uses for such antibodies. The antibodies, or the product (epitopes of interest) which elicited them, or monoclonal antibodies from the antibodies, can be used in binding assays, tests or kits to determine the presence or absence of an antigen or antibody.

Flanking DNA used in the invention can be from the site of insertion or a portion of the genome adjacent thereto (wherein "adjacent" includes contiguous sequences, e.g., codon or codons, as well as up to as many sequences, e.g., codon or codons, before there is an intervening insertion site).

As to antigens for use in vaccine or immunological compositions, see also Stedman's Medical Dictionary (24th edition, 1982, e.g., definition of vaccine (for a list of antigens used in vaccine formulations; such antigens or epitopes of interest from those antigens can be used in the invention, as either an expression product of the inventive recombinant virus, or in a multivalent composition containing an inventive recombinant virus or an expression product therefrom).

As to heterologous antigens, one skilled in the art can select a heterologous antigen and the coding DNA therefor from the knowledge of the amino acid and corresponding DNA sequences of the peptide or polypeptide, as well as from the nature of particular amino acids (e.g., size, charge, etc.) and the codon dictionary, without undue experimentation.

With respect to the sequence, the DNA sequence preferably encodes at least regions of the antigen that generate an antibody response or a T cell response, particularly a $CD8^+$ T cell response. One method to determine T and B cell epitopes involves epitope mapping. Overlapping peptides of the heterologous antigen are generated by oligo-peptide synthesis. The individual peptides are then tested for their ability to bind to an antibody elicited by the native protein or to induce T cell or B cell activation. This approach has been particularly useful in mapping T-cell epitopes since the T cell recognizes short linear peptides complexed with MHC molecules.

An immune response to a heterologous antigen is generated, in general, as follows: T cells recognize proteins only when the protein has been cleaved into smaller peptides and is presented in a complex called the "major histocompatability complex (MHC)" located on another cell's surface. There are two classes of MHC complexes—class I and class II, and each class is made up of many different alleles. Different species, and individual subjects have different types of MHC complex alleles; they are said to have a different HLA type.

It is noted that the DNA comprising the sequence encoding the heterologous antigen can itself include a promoter for driving expression in the CMV vector or the DNA can be limited to the coding DNA of the heterologous antigen. This construct can be placed in such an orientation relative to an endogenous CMV promoter that it is operably linked to the promoter and is thereby expressed. Further, multiple copies of DNA encoding the heterologous antigen or use of a strong or early promoter or early and late promoter, or any combination thereof, can be done so as to amplify or increase expression. Thus, the DNA encoding the heterologous antigen can be suitably positioned with respect to a CMV-endogenous promoter, or those promoters can be translocated to be inserted at another location together with the DNA encoding the heterologous antigen. Nucleic acids encoding more than one heterologous antigen can be packaged in the CMV vector.

Further disclosed are pharmaceutical and other compositions containing the disclosed CMV vectors. Such pharmaceutical and other compositions can be formulated so as to be used in any administration procedure known in the art. Such pharmaceutical compositions can be via a parenteral route (intradermal, intramuscular, subcutaneous, intravenous, or others). The administration can also be via a mucosal route, e.g., oral, nasal, genital, etc.

The disclosed pharmaceutical compositions can be prepared in accordance with standard techniques well known to those skilled in the pharmaceutical arts. Such compositions can be administered in dosages and by techniques well known to those skilled in the medical arts taking into consideration such factors as the breed or species, age, sex, weight, and condition of the particular patient, and the route of administration. The compositions can be administered alone, or can be co-administered or sequentially administered with other CMV vectors or with other immunological, antigenic or vaccine or therapeutic compositions. Such other compositions can include purified native antigens or epitopes or antigens or epitopes from the expression by a recombinant CMV or another vector system; and are administered taking into account the aforementioned factors.

Examples of compositions of the invention include liquid preparations for orifice, e.g., oral, nasal, anal, genital, e.g., vaginal, etc., administration such as suspensions, syrups or elixirs; and, preparations for parenteral, subcutaneous, intradermal, intramuscular or intravenous administration (e.g., injectable administration) such as sterile suspensions or emulsions. In such compositions the recombinant may be in admixture with a suitable carrier, diluent, or excipient such as sterile water, physiological saline, glucose or the like.

Antigenic, immunological or vaccine compositions typically can contain an adjuvant and an amount of the CMV vector or expression product to elicit the desired response. In human applications, alum (aluminum phosphate or aluminum hydroxide) is a typical adjuvant. Saponin and its purified component Quil A, Freund's complete adjuvant and other adjuvants used in research and veterinary applications have toxicities which limit their potential use in human vaccines. Chemically defined preparations such as muramyl dipeptide, monophosphoryl lipid A, phospholipid conjugates such as those described by Goodman-Snitkoff et al. J. Immunol. 147:410-415 (1991), encapsulation of the protein within a proteoliposome as described by Miller et al., J. Exp. Med. 176:1739-1744 (1992), and encapsulation of the protein in lipid vesicles such as Novasome lipid vesicles (Micro Vescular Systems, Inc., Nashua, N.H.) can also be used.

The composition may be packaged in a single dosage form for immunization by parenteral (i.e., intramuscular, intradermal or subcutaneous) administration or orifice administration, e.g., perlingual (e.g., oral), intragastric, mucosal including intraoral, intraanal, intravaginal, and the like administration. And again, the effective dosage and route of administration are determined by the nature of the composition, by the nature of the expression product, by expression level if recombinant CMV is directly used, and by known factors, such as breed or species, age, sex, weight, condition and nature of host, as well as $LD_{50}$ and other screening procedures which are known and do not require undue experimentation. Dosages of expressed product can range from a few to a few hundred micrograms, e.g., 5 to 500 µg. The CMV vector can be administered in any suitable amount to achieve expression at these dosage levels. In nonlimiting examples: CMV vectors can be administered in an amount of at least $10^2$ pfu; thus, CMV vectors can be administered in at least this amount; or in a range from about $10^2$ pfu to about 10' pfu. Other suitable carriers or diluents can be water or a buffered saline, with or without a preservative. The CMV vector can be lyophilized for resuspension at the time of administration or can be in solution.

The carrier may also be a polymeric delayed release system. Synthetic polymers are particularly useful in the formulation of a composition having controlled release. An early example of this was the polymerization of methyl methacrylate into spheres having diameters less than one micron to form so-called nanoparticles, reported by Kreuter, J., Microcapsules and Nanoparticles in Medicine and Pharmacology, M. Donbrow (Ed). CRC Press, p. 125-148.

Microencapsulation has been applied to the injection of microencapsulated pharmaceuticals to give a controlled release. A number of factors contribute to the selection of a particular polymer for microencapsulation. The reproducibility of polymer synthesis and the microencapsulation process, the cost of the microencapsulation materials and process, the toxicological profile, the requirements for variable release kinetics and the physicochemical compatibility of the polymer and the antigens are all factors that must be considered. Examples of useful polymers are polycarbonates, polyesters, polyurethanes, polyorthoesters and polyamides, particularly those that are biodegradable.

A frequent choice of a carrier for pharmaceuticals and more recently for antigens is poly (d,1-lactide-co-glycolide) (PLGA). This is a biodegradable polyester that has a long history of medical use in erodible sutures, bone plates and other temporary prostheses where it has not exhibited any toxicity. A wide variety of pharmaceuticals including peptides and antigens have been formulated into PLGA microcapsules. A body of data has accumulated on the adaption of PLGA for the controlled release of antigen, for example, as reviewed by Eldridge, J. H., et al. Current Topics in Microbiology and Immunology. 1989, 146:59-66. The entrapment of antigens in PLGA microspheres of 1 to 10 microns in diameter has been shown to have a remarkable adjuvant effect when administered orally. The PLGA microencapsulation process uses a phase separation of a water-in-oil emulsion. The compound of interest is prepared as an aqueous solution and the PLGA is dissolved in a suitable organic solvents such as methylene chloride and ethyl acetate. These two immiscible solutions are co-emulsified by high-speed stirring. A non-solvent for the polymer is then added, causing precipitation of the polymer around the aqueous droplets to form embryonic microcapsules. The microcapsules are collected, and stabilized with one of an assortment of agents (polyvinyl alcohol (PVA), gelatin, alginates, polyvinylpyrrolidone (PVP), methyl cellulose) and the solvent removed by either drying in vacuo or solvent extraction.

As to HCMV promoters, reference is made to U.S. Pat. Nos. 5,168,062 and 5,385,839. As to transfecting cells with plasmid DNA for expression therefrom, reference is made to Feigner et al. (1994), J. Biol. Chem. 269, 2550-2561. And, as to direct injection of plasmid DNA as a simple and effective method of vaccination against a variety of infectious diseases reference is made to Science, 259:1745-49, 1993. It is therefore within the scope of this invention that the vector can be used by the direct injection of vector DNA.

The terms "protein", "peptide", "polypeptide", and "amino acid sequence" are used interchangeably herein to refer to polymers of amino acid residues of any length. The polymer may be linear or branched, it may comprise modified amino acids or amino acid analogs, and it may be interrupted by chemical moieties other than amino acids. The terms also encompass an amino acid polymer that has been modified naturally or by intervention; for example disulfide bond formation, glycosylation, lipidation, acetylation, phosphorylation, or any other manipulation or modification, such as conjugation with a labeling or bioactive component.

As used herein, the terms "antigen" or "immunogen" are used interchangeably to refer to a substance, typically a protein, which is capable of inducing an immune response in a subject. The term also refers to proteins that are immunologically active in the sense that once administered to a subject (either directly or by administering to the subject a nucleotide sequence or vector that encodes the protein) is able to evoke an immune response of the humoral and/or cellular type directed against that protein.

It should be understood that the proteins and the nucleic acids encoding them may differ from the exact sequences illustrated and described herein. Thus, the invention contemplates deletions, additions, truncations, and substitutions to the sequences shown, so long as the sequences function in accordance with the methods of the invention. In this regard, substitutions will generally be conservative in nature, i.e., those substitutions that take place within a family of amino acids. For example, amino acids are generally divided into four families: (1) acidic—aspartate and glutamate; (2) basic—lysine, arginine, histidine; (3) non-polar—alanine, valine, leucine, isoleucine, proline, phenylalanine, methionine, tryptophan; and (4) uncharged polar—glycine, asparagine, glutamine, cysteine, serine threonine, and tyrosine. Phenylalanine, tryptophan, and tyrosine are sometimes classified as aromatic amino acids. It is reasonably predictable that an isolated replacement of leucine with isoleucine or valine, or vice versa; an aspartate with a glutamate or vice versa; a threonine with a serine or vice versa; or a similar conservative replacement of an amino acid with a structurally related amino acid, will not have a major effect on the biological activity. Proteins having substantially the same amino acid sequence as the sequences illustrated and described but possessing minor amino acid substitutions that do not substantially affect the immunogenicity of the protein are, therefore, within the scope of the invention.

As used herein the terms "nucleotide sequences" and "nucleic acid sequences" refer to deoxyribonucleic acid (DNA) or ribonucleic acid (RNA) sequences, including, without limitation, messenger RNA (mRNA), DNA/RNA hybrids, or synthetic nucleic acids. The nucleic acid can be single-stranded, or partially or completely double-stranded (duplex). Duplex nucleic acids can be homoduplex or heteroduplex.

As used herein the term "transgene" can be used to refer to "recombinant" nucleotide sequences that may be derived from any of the nucleotide sequences encoding the proteins of the present invention. The term "recombinant" means a nucleotide sequence that has been manipulated "by man" and which does not occur in nature, or is linked to another nucleotide sequence or found in a different arrangement in nature. It is understood that manipulated "by man" means manipulated by some artificial means, including by use of machines, codon optimization, restriction enzymes, etc. A CMV vector that encodes a heterologous antigen is by definition a recombinant CMV vector.

The nucleotide sequences can be codon optimized, for example the codons may be optimized for use in human cells. For example, any viral or bacterial sequence can be so altered. Many viruses, including HIV and other lentiviruses, use a large number of rare codons and, by altering these codons to correspond to codons commonly used in the desired subject, enhanced expression of the heterologous antigen can be achieved as described in Andre et al., J. Virol. 72:1497-1503, 1998.

Nucleotide sequences encoding functionally and/or antigenically equivalent variants and derivatives of the CMV vectors and the glycoproteins included therein are contemplated. These functionally equivalent variants, derivatives, and fragments display the ability to retain antigenic activity. For instance, changes in a DNA sequence that do not change the encoded amino acid sequence, as well as those that result in conservative substitutions of amino acid residues, one or a few amino acid deletions or additions, and substitution of amino acid residues by amino acid analogs are those which will not significantly affect properties of the encoded polypeptide. Conservative amino acid substitutions are glycine/alanine; valine/isoleucine/leucine; asparagine/glutamine; aspartic acid/glutamic acid; serine/threonine/methionine; lysine/arginine; and phenylalanine/tyrosine/tryptophan. In one embodiment, the variants have at least 50%, at least 55%, at least 60%, at least 65%, at least 70%, at least 75%, at least 80%, at least 85%, at least 86%, at least 87%, at least 88%, at least 89%, at least 90%, at least 91%, at least 92%, at least 93%, at least 94%, at least 95%, at least 96%, at least 97%, at least 98% or at least 99% homology or identity to the antigen, epitope, immunogen, peptide or polypeptide of interest.

Sequence identity or homology is determined by comparing the sequences when aligned so as to maximize overlap and identity while minimizing sequence gaps. In particular, sequence identity may be determined using any of a number of mathematical algorithms. A nonlimiting example of a mathematical algorithm used for comparison of two sequences is the algorithm of Karlin & Altschul, Proc. Natl. Acad. Sci. USA 1990; 87: 2264-2268, modified as in Karlin & Altschul, Proc. Natl. Acad. Sci. USA 1993; 90: 5873-5877.

Another example of a mathematical algorithm used for comparison of sequences is the algorithm of Myers & Miller, CABIOS 1988; 4: 11-17. Such an algorithm is incorporated into the ALIGN program (version 2.0) which is part of the GCG sequence alignment software package. When utilizing the ALIGN program for comparing amino acid sequences, a PAM120 weight residue table, a gap length penalty of 12, and a gap penalty of 4 can be used. Yet another useful algorithm for identifying regions of local sequence similarity and alignment is the FASTA algorithm as described in Pearson & Lipman, Proc. Natl. Acad. Sci. USA 1988; 85: 2444-2448.

Advantageous for use according to the present invention is the WU-BLAST (Washington University BLAST) version 2.0 software. WU-BLAST version 2.0 executable programs for several UNIX platforms can be downloaded. This program is based on WU-BLAST version 1.4, which in turn is based on the public domain NCBI-BLAST version 1.4 (Altschul & Gish, 1996, Local alignment statistics, Doolittle ed., Methods in Enzymology 266: 460-480; Altschul et al., Journal of Molecular Biology 1990; 215: 403-410; Gish & States, 1993; Nature Genetics 3: 266-272; Karlin & Altschul, 1993; Proc. Natl. Acad. Sci. USA 90: 5873-5877; all of which are incorporated by reference herein).

The various recombinant nucleotide sequences and antibodies and/or antigens of the invention are made using standard recombinant DNA and cloning techniques. Such techniques are well known to those of skill in the art. See for example, "Molecular Cloning: A Laboratory Manual", second edition (Sambrook et al. 1989).

The nucleotide sequences of the present invention may be inserted into "vectors." The term "vector" is widely used and understood by those of skill in the art, and as used herein the term "vector" is used consistent with its meaning to those of skill in the art. For example, the term "vector" is commonly used by those skilled in the art to refer to a vehicle that allows or facilitates the transfer of nucleic acid molecules from one environment to another or that allows or facilitates the manipulation of a nucleic acid molecule.

Any vector that allows expression of the viruses of the present invention may be used in accordance with the present invention. In certain embodiments, the viruses of the present invention may be used in vitro (such as using cell-free expression systems) and/or in cultured cells grown in vitro in order to produce the encoded HIV-antigens and/or antibodies which may then be used for various applications such as in the production of proteinaceous vaccines. For such applications, any vector that allows expression of the virus in vitro and/or in cultured cells may be used.

For the heterologous antigens of the present invention to be expressed, the protein coding sequence of the heterologous antigen should be "operably linked" to regulatory or nucleic acid control sequences that direct transcription and translation of the protein. As used herein, a coding sequence and a nucleic acid control sequence or promoter are said to be "operably linked" when they are covalently linked in such a way as to place the expression or transcription and/or translation of the coding sequence under the influence or control of the nucleic acid control sequence. The "nucleic acid control sequence" can be any nucleic acid element, such as, but not limited to promoters, enhancers, IRES, introns, and other elements described herein that direct the expression of a nucleic acid sequence or coding sequence that is operably linked thereto. The term "promoter" will be used herein to refer to a group of transcriptional control modules that are clustered around the initiation site for RNA polymerase II and that when operationally linked to the protein coding sequences of the invention lead to the expression of the encoded protein. The expression of the transgenes of the present invention can be under the control of a constitutive promoter or of an inducible promoter, which initiates transcription only when exposed to some particular external stimulus, such as, without limitation, antibiotics such as tetracycline, hormones such as ecdysone, or heavy metals. The promoter can also be specific to a particular cell-type, tissue or organ. Many suitable promoters and enhancers are known in the art, and any such suitable promoter or enhancer may be used for expression of the transgenes of the invention. For example, suitable promoters and/or enhancers can be selected from the Eukaryotic Promoter Database (EPDB).

The present invention relates to a recombinant viral vector expressing a foreign epitope. Advantageously, the epitope is an HIV epitope. In an advantageous embodiment, the HIV epitope is a protein fragment of the present invention, however, the present invention may encompass additional HIV antigens, epitopes or immunogens. Advantageously, the HIV epitope is an HIV antigen including but not limited to, the HIV antigens of U.S. Pat. Nos. 7,341,731; 7,335,364; 7,329,807; 7,323,553; 7,320,859; 7,311,920; 7,306,798; 7,285,646; 7,285,289; 7,285,271; 7,282,364; 7,273,695; 7,270,997; 7,262,270; 7,244,819; 7,244,575; 7,232,567; 7,232,566; 7,223,844; 7,223,739; 7,223,534; 7,223,368; 7,220,554; 7,214,530; 7,211,659; 7,211,432; 7,205,159; 7,198,934; 7,195,768; 7,192,555; 7,189,826; 7,189,522; 7,186,507; 7,179,645; 7,175,843; 7,172,761; 7,169,550; 7,157,083; 7,153,509; 7,147,862; 7,141,550; 7,129,219; 7,122,188; 7,118,859; 7,118,855; 7,118,751; 7,118,742; 7,105,655; 7,101,552; 7,097,971 7,097,842; 7,094,405; 7,091,049; 7,090,648; 7,087,377; 7,083,787; 7,070,787; 7,070,781; 7,060,273; 7,056,521; 7,056,519; 7,049,136; 7,048,929; 7,033,593; 7,030,094; 7,022,326; 7,009,037; 7,008,622; 7,001,759; 6,997,863; 6,995,008; 6,979,535; 6,974,574; 6,972,126; 6,969,609; 6,964,769; 6,964,762; 6,958,158; 6,956,059; 6,953,689; 6,951,648; 6,946,075; 6,927,031; 6,919,319; 6,919,318; 6,919,077; 6,913,752; 6,911,315; 6,908,617; 6,908,612; 6,902,743; 6,900,010; 6,893,869; 6,884,785; 6,884,435; 6,875,435; 6,867,005; 6,861,234; 6,855,539; 6,841,381 6,841,345; 6,838,477; 6,821,955; 6,818,392; 6,818,222; 6,815,217; 6,815,201; 6,812,026; 6,812,025; 6,812,024; 6,808,923; 6,806,055; 6,803,231; 6,800,613; 6,800,288; 6,797,811; 6,780,967; 6,780,598; 6,773,920; 6,764,682; 6,761,893; 6,753,015; 6,750,005; 6,737,239; 6,737,067; 6,730,304; 6,720,310; 6,716,823; 6,713,301; 6,713,070; 6,706,859; 6,699,722; 6,699,656; 6,696,291; 6,692,745; 6,670,181; 6,670,115; 6,664,406; 6,657,055; 6,657,050; 6,656,471; 6,653,066; 6,649,409; 6,649,372; 6,645,732; 6,641,816; 6,635,469; 6,613,530; 6,605,427; 6,602,709 6,602,705; 6,600,023; 6,596,477; 6,596,172; 6,593,103; 6,593,079; 6,579,673; 6,576,758; 6,573,245; 6,573,040; 6,569,418; 6,569,340; 6,562,800; 6,558,961; 6,551,828; 6,551,824; 6,548,275; 6,544,780; 6,544,752; 6,544,728; 6,534,482; 6,534,312; 6,534,064; 6,531,572; 6,531,313; 6,525,179; 6,525,028; 6,524,582; 6,521,449; 6,518,030; 6,518,015; 6,514,691; 6,514,503; 6,511,845; 6,511,812; 6,511,801; 6,509,313; 6,506,384; 6,503,882; 6,495,676; 6,495,526; 6,495,347; 6,492,123; 6,489,131; 6,489,129; 6,482,614; 6,479,286; 6,479,284; 6,465,634; 6,461,615 6,458,560; 6,458,527; 6,458,370; 6,451,601; 6,451,592; 6,451,323; 6,436,407; 6,432,633; 6,428,970; 6,428,952; 6,428,790; 6,420,139; 6,416,997; 6,410,318; 6,410,028; 6,410,014; 6,407,221; 6,406,710; 6,403,092; 6,399,295; 6,392,013; 6,391,657; 6,384,198; 6,380,170; 6,376,170; 6,372,426; 6,365,187; 6,358,739; 6,355,248; 6,355,247; 6,348,450; 6,342,372; 6,342,228; 6,338,952; 6,337,179; 6,335,183; 6,335,017; 6,331,404; 6,329,202; 6,329,173; 6,328,976; 6,322,964; 6,319,666; 6,319,665; 6,319,500; 6,319,494; 6,316,205; 6,316,003; 6,309,633; 6,306,625 6,296,807; 6,294,322; 6,291,239; 6,291,157; 6,287,568; 6,284,456; 6,284,194; 6,274,337; 6,270,956; 6,270,769; 6,268,484; 6,265,562; 6,265,149; 6,262,029; 6,261,762; 6,261,571; 6,261,569; 6,258,599; 6,258,358; 6,248,332; 6,245,331; 6,242,461; 6,241,986; 6,235,526; 6,235,466; 6,232,120; 6,228,361; 6,221,579; 6,214,862; 6,214,804; 6,210,963; 6,210,873; 6,207,185; 6,203,974; 6,197,755; 6,197,531; 6,197,496; 6,194,142; 6,190,871; 6,190,666; 6,168,923; 6,156,302; 6,153,408; 6,153,393; 6,153,392; 6,153,378; 6,153,377; 6,146,635; 6,146,614; 6,143,876 6,140,059; 6,140,043; 6,139,746; 6,132,992; 6,124,306; 6,124,132; 6,121,006; 6,120,990; 6,114,507; 6,114,143; 6,110,466; 6,107,020; 6,103,521; 6,100,234; 6,099,848; 6,099,847; 6,096,291; 6,093,405; 6,090,392; 6,087,476; 6,083,903; 6,080,846; 6,080,725; 6,074,650; 6,074,646; 6,070,126; 6,063,905; 6,063,564; 6,060,256; 6,060,064; 6,048,530; 6,045,788; 6,043,347; 6,043,248; 6,042,831; 6,037,165; 6,033,672; 6,030,772; 6,030,770; 6,030,618; 6,025,141; 6,025,125; 6,020,468; 6,019,979; 6,017,543; 6,017,537; 6,015,694; 6,015,661; 6,013,484; 6,013,432 6,007,838; 6,004,811; 6,004,807; 6,004,763; 5,998,132; 5,993,819; 5,989,806; 5,985,926; 5,985,641; 5,985,545; 5,981,537; 5,981,505; 5,981,170; 5,976,551; 5,972,339; 5,965,371; 5,962,428; 5,962,318; 5,961,979; 5,961,970; 5,958,765; 5,958,422; 5,955,647; 5,955,342; 5,951,986; 5,951,975; 5,942,237; 5,939,277; 5,939,074; 5,935,580; 5,928,930; 5,928,913; 5,928,644; 5,928,642; 5,925,513; 5,922,550; 5,922,325; 5,919,458; 5,916,806; 5,916,563; 5,914,395; 5,914,109; 5,912,383; 5,912,176; 5,912,170; 5,906,936; 5,895,650; 5,891,623; 5,888,726; 5,885,580 5,885,578; 5,879,685; 5,876,731; 5,876,716; 5,874,226; 5,872,012; 5,871,747; 5,869,058; 5,866,694; 5,866,341; 5,866,320; 5,866,319; 5,866,137; 5,861,290; 5,858,740; 5,858,647; 5,858,646; 5,858,369; 5,858,368; 5,858,366; 5,856,185; 5,854,400; 5,853,736; 5,853,725; 5,853,724; 5,852,186; 5,851,829; 5,851,529; 5,849,475; 5,849,288; 5,843,728; 5,843,723; 5,843,640; 5,843,635; 5,840,480; 5,837,510; 5,837,250; 5,837,242; 5,834,599; 5,834,441; 5,834,429; 5,834,256; 5,830,876; 5,830,641; 5,830,475; 5,830,458; 5,830,457; 5,827,749; 5,827,723; 5,824,497 5,824,304; 5,821,047; 5,817,767; 5,817,754; 5,817,637; 5,817,470; 5,817,318; 5,814,482; 5,807,707; 5,804,604; 5,804,371; 5,800,822; 5,795,955; 5,795,743; 5,795,572; 5,789,388; 5,780,279; 5,780,038; 5,776,703; 5,773,260; 5,770,572; 5,766,844; 5,766,842; 5,766,625; 5,763,574; 5,763,190; 5,762,965; 5,759,769; 5,756,666; 5,753,258; 5,750,373; 5,747,641; 5,747,526; 5,747,028; 5,736,320; 5,736,146; 5,733,760; 5,731,189; 5,728,385; 5,721,095; 5,716,826; 5,716,637; 5,716,613; 5,714,374; 5,709,879; 5,709,860; 5,709,843; 5,705,331; 5,703,057; 5,702,707 5,698,178; 5,688,914; 5,686,078; 5,681,831; 5,679,784; 5,674,984; 5,672,472; 5,667,964; 5,667,783; 5,665,536; 5,665,355; 5,660,990; 5,658,745; 5,658,569; 5,643,756; 5,641,624; 5,639,854; 5,639,598; 5,637,677; 5,637,455; 5,633,234; 5,629,153; 5,627,025; 5,622,705; 5,614,413; 5,610,035; 5,607,831; 5,606,026; 5,601,819; 5,597,688; 5,593,972; 5,591,829; 5,591,823; 5,589,466; 5,587,285; 5,585,254; 5,585,250; 5,580,773; 5,580,739; 5,580,563; 5,573,916; 5,571,667; 5,569,468; 5,558,865; 5,556,745; 5,550,052; 5,543,328; 5,541,100; 5,541,057; 5,534,406 5,529,765; 5,523,232; 5,516,895; 5,514,541; 5,510,264; 5,500,161; 5,480,967; 5,480,966; 5,470,701; 5,468,606; 5,462,852; 5,459,127; 5,449,601; 5,447,838; 5,447,837; 5,439,809; 5,439,792; 5,418,136; 5,399,501; 5,397,695; 5,391,479; 5,384,240; 5,374,519; 5,374,518; 5,374,516; 5,364,933; 5,359,046; 5,356,772; 5,354,654; 5,344,755; 5,335,673; 5,332,567; 5,320,940; 5,317,009; 5,312,902; 5,304,466; 5,296,347; 5,286,852; 5,268,265; 5,264,356; 5,264,342; 5,260,308; 5,256,767; 5,256,561; 5,252,556; 5,230,998; 5,230,887; 5,227,159; 5,225,347; 5,221,610 5,217,861; 5,208,321; 5,206,136; 5,198,346; 5,185,147; 5,178,865; 5,173,400; 5,173,399; 5,166,050; 5,156,951; 5,135,864; 5,122,446;

5,120,662; 5,103,836; 5,100,777; 5,100,662; 5,093,230; 5,077,284; 5,070,010; 5,068,174; 5,066,782; 5,055,391; 5,043,262; 5,039,604; 5,039,522; 5,030,718; 5,030,555; 5,030,449; 5,019,387; 5,013,556; 5,008,183; 5,004,697; 4,997,772; 4,983,529; 4,983,387; 4,965,069; 4,945,082; 4,921,787; 4,918,166; 4,900,548; 4,888,290; 4,886,742; 4,885,235; 4,870,003; 4,869,903; 4,861,707; 4,853,326; 4,839,288; 4,833,072 and 4,795,739.

In another embodiment, HIV, or immunogenic fragments thereof, may be utilized as the HIV epitope. For example, the HIV nucleotides of U.S. Pat. Nos. 7,393,949, 7,374,877, 7,306,901, 7,303,754, 7,173,014, 7,122,180, 7,078,516, 7,022,814, 6,974,866, 6,958,211, 6,949,337, 6,946,254, 6,896,900, 6,887,977, 6,870,045, 6,803,187, 6,794,129, 6,773,915, 6,768,004, 6,706,268, 6,696,291, 6,692,955, 6,656,706, 6,649,409, 6,627,442, 6,610,476, 6,602,705, 6,582,920, 6,557,296, 6,531,587, 6,531,137, 6,500,623, 6,448,078, 6,429,306, 6,420,545, 6,410,013, 6,407,077, 6,395,891, 6,355,789, 6,335,158, 6,323,185, 6,316,183, 6,303,293, 6,300,056, 6,277,561, 6,270,975, 6,261,564, 6,225,045, 6,222,024, 6,194,391, 6,194,142, 6,162,631, 6,114,167, 6,114,109, 6,090,392, 6,060,587, 6,057,102, 6,054,565, 6,043,081, 6,037,165, 6,034,233, 6,033,902, 6,030,769, 6,020,123, 6,015,661, 6,010,895, 6,001,555, 5,985,661, 5,980,900, 5,972,596, 5,939,538, 5,912,338, 5,869,339, 5,866,701, 5,866,694, 5,866,320, 5,866,137, 5,864,027, 5,861,242, 5,858,785, 5,858,651, 5,849,475, 5,843,638, 5,840,480, 5,821,046, 5,801,056, 5,786,177, 5,786,145, 5,773,247, 5,770,703, 5,756,674, 5,741,706, 5,705,612, 5,693,752, 5,688,637, 5,688,511, 5,684,147, 5,665,577, 5,585,263, 5,578,715, 5,571,712, 5,567,603, 5,554,528, 5,545,726, 5,527,895, 5,527,894, 5,223,423, 5,204,259, 5,144,019, 5,051,496 and 4,942,122 are useful for the present invention.

Any epitope recognized by an HIV antibody may be used in the present invention. For example, the anti-HIV antibodies of U.S. Pat. Nos. 6,949,337, 6,900,010, 6,821,744, 6,768,004, 6,613,743, 6,534,312, 6,511,830, 6,489,131, 6,242,197, 6,114,143, 6,074,646, 6,063,564, 6,060,254, 5,919,457, 5,916,806, 5,871,732, 5,824,304, 5,773,247, 5,736,320, 5,637,455, 5,587,285, 5,514,541, 5,317,009, 4,983,529, 4,886,742, 4,870,003 and 4,795,739 are useful for the present invention. Furthermore, monoclonal anti-HIV antibodies of U.S. Pat. Nos. 7,074,556, 7,074,554, 7,070,787, 7,060,273, 7,045,130, 7,033,593, RE39,057, 7,008,622, 6,984,721, 6,972,126, 6,949,337, 6,946,465, 6,919,077, 6,916,475, 6,911,315, 6,905,680, 6,900,010, 6,825,217, 6,824,975, 6,818,392, 6,815,201, 6,812,026, 6,812,024, 6,797,811, 6,768,004, 6,703,019, 6,689,118, 6,657,050, 6,608,179, 6,600,023, 6,596,497, 6,589,748, 6,569,143, 6,548,275, 6,525,179, 6,524,582, 6,506,384, 6,498,006, 6,489,131, 6,465,173, 6,461,612, 6,458,933, 6,432,633, 6,410,318, 6,406,701, 6,395,275, 6,391,657, 6,391,635, 6,384,198, 6,376,170, 6,372,217, 6,344,545, 6,337,181, 6,329,202, 6,319,665, 6,319,500, 6,316,003, 6,312,931, 6,309,880, 6,296,807, 6,291,239, 6,261,558, 6,248,514, 6,245,331, 6,242,197, 6,241,986, 6,228,361, 6,221,580, 6,190,871, 6,177,253, 6,146,635, 6,146,627, 6,146,614, 6,143,876, 6,132,992, 6,124,132, RE36,866, 6,114,143, 6,103,238, 6,060,254, 6,039,684, 6,030,772, 6,020,468, 6,013,484, 6,008,044, 5,998,132, 5,994,515, 5,993,812, 5,985,545, 5,981,278, 5,958,765, 5,939,277, 5,928,930, 5,922,325, 5,919,457, 5,916,806, 5,914,109, 5,911,989, 5,906,936, 5,889,158, 5,876,716, 5,874,226, 5,872,012, 5,871,732, 5,866,694, 5,854,400, 5,849,583, 5,849,288, 5,840,480, 5,840,305, 5,834,599, 5,831,034, 5,827,723, 5,821,047, 5,817,767, 5,817,458, 5,804,440, 5,795,572, 5,783,670, 5,776,703, 5,773,225, 5,766,944, 5,753,503, 5,750,373, 5,747,641, 5,736,341, 5,731,189, 5,707,814, 5,702,707, 5,698,178, 5,695,927, 5,665,536, 5,658,745, 5,652,138, 5,645,836, 5,635,345, 5,618,922, 5,610,035, 5,607,847, 5,604,092, 5,601,819, 5,597,896, 5,597,688, 5,591,829, 5,558,865, 5,514,541, 5,510,264, 5,478,753, 5,374,518, 5,374,516, 5,344,755, 5,332,567, 5,300,433, 5,296,347, 5,286,852, 5,264,221, 5,260,308, 5,256,561, 5,254,457, 5,230,998, 5,227,159, 5,223,408, 5,217,895, 5,180,660, 5,173,399, 5,169,752, 5,166,050, 5,156,951, 5,140,105, 5,135,864, 5,120,640, 5,108,904, 5,104,790, 5,049,389, 5,030,718, 5,030,555, 5,004,697, 4,983,529, 4,888,290, 4,886,742 and 4,853,326, are also useful for the present invention.

In one example, the epitope is an SIV epitope. It is understood by one of skill in the art that anything referring to HIV in the specification also applies to SIV. In an advantageous embodiment, the SIV epitope is a protein fragment of the present invention, however, the present invention may encompass additional SIV antigens, epitopes or immunogens. Advantageously, the SIV epitope is an SIV antigen, including but not limited to, the SIV antigens of U.S. Pat. Nos. 7,892,729; 7,886,962; 7,879,914; 7,829,287; 7,794,998; 7,767,455; 7,759,477; 7,758,869; 7,754,420; 7,749,973; 7,748,618; 7,732,124; 7,709,606; 7,700,342; 7,700,273; 7,625,917; 7,622,124; 7,611,721; 7,608,422; 7,601,518; 7,585,675; 7,534,603; 7,511,117; 7,508,781; 7,507,417; 7,479,497; 7,464,352; 7,457,973; 7,442,551; 7,439,052; 7,419,829; 7,407,663; 7,378,515; 7,364,760; 7,312,065; 7,261,876; 7,220,554; 7,211,240; 7,198,935; 7,169,394; 7,098,201; 7,078,516; 7,070,993; 7,048,929; 7,034,010; RE39,057; 7,022,814; 7,018,638 6,955,919; 6,933,377; 6,908,617; 6,902,929; 6,846,477; 6,818,442; 6,803,231; 6,800,281; 6,797,811; 6,790,657; 6,712,612; 6,706,729; 6,703,394; 6,682,907; 6,656,706; 6,645,956; 6,635,472; 6,596,539; 6,589,763; 6,562,571; 6,555,523; 6,555,342; 6,541,009; 6,531,574; 6,531,123; 6,503,713; 6,479,281; 6,475,718; 6,469,083; 6,468,539; 6,455,265; 6,448,390; 6,440,730; 6,423,544; 6,365,150; 6,362,000; 6,326,007; 6,322,969; 6,291,664; 6,277,601; 6,261,571; 6,255,312; 6,207,455; 6,194,142; 6,117,656; 6,111,087; 6,107,020; 6,080,846; 6,060,064; 6,046,228; 6,043,081; 6,027,731; 6,020,123; 6,017,536; 6,004,781; 5,994,515; 5,981,259; 5,961,976; 5,950,176; 5,929,222; 5,928,913; 5,912,176; 5,888,726; 5,861,243; 5,861,161; 5,858,366; 5,830,475; 5,817,316; 5,804,196; 5,786,177; 5,759,768; 5,747,324; 5,705,522; 5,705,331; 5,698,446; 5,688,914; 5,688,637; 5,654,195; 5,650,269; 5,631,154; 5,582,967; 5,552,269; 5,512,281; 5,508,166; 5,470,572; 5,312,902; 5,310,651; 5,268,265; 5,254,457; 5,212,084; 5,087,631 and 4,978,687.

The vectors used in accordance with the present invention should typically be chosen such that they contain a suitable gene regulatory region, such as a promoter or enhancer, such that the antigens of the invention can be expressed.

When the aim is to express antigens of the invention in vivo in a subject, for example in order to generate an immune response against an HIV-1 antigen and/or protective immunity against HIV-1, expression vectors that are suitable for expression on that subject, and that are safe for use in vivo, should be chosen. For example, in some embodiments it may be desired to express the antibodies and/or antigens of the invention in a laboratory animal, such as for preclinical testing of the HIV-1 immunogenic compositions and vaccines of the invention. In other embodiments, it will be desirable to express the antigens of the invention in human subjects, such as in clinical trials and for actual clinical use of the immunogenic compositions and vaccine of the invention. Any vectors that are suitable for such uses can be employed, and it is well within the capabilities of the skilled artisan to select a suitable vector. In some embodiments it may be preferred that the vectors used for these in vivo applications are attenuated to vector from amplifying in the subject. For example, if plasmid vectors are used, preferably they will lack an origin of replication that functions in the subject so as to enhance safety for in vivo use in the subject. If viral vectors are used, preferably they are attenuated or replication-defective in the subject, again, so as to enhance safety for in vivo use in the subject.

In preferred embodiments of the present invention viral vectors are used. Advantageously, the vector is a CMV vector, lacking at least the glycoprotein UL128 or a CMV vector lacking at least the glycoprotein UL130. Each CMV vector also expresses the glycoprotein UL131.

The disclosed CMV vectors can be administered in vivo, for example where the aim is to produce an immunogenic response, including a CD8+ immune response, including an immune response characterized by a high percentage of the CD8+ T cell response to the heterologous antigen directed against epitopes presented by MHC Class II in a subject. For example, in some embodiments it may be desired to use the disclosed CMV vectors in a laboratory animal, such as rhesus macaques for pre-clinical testing of immunogenic compositions and vaccines using RhCMV. In other embodiments, it will be desirable to use the disclosed CMV vectors in human subjects, such as in clinical trials and for actual clinical use of the immunogenic compositions using HCMV.

For such in vivo applications the disclosed CMV vectors are administered as a component of an immunogenic composition further comprising a pharmaceutically acceptable carrier. The immunogenic compositions of the invention are useful to stimulate an immune response against the heterologous antigen, including a pathogen specific antigen and may be used as one or more components of a prophylactic or therapeutic vaccine against HIV-1 for the prevention, amelioration or treatment of AIDS. The nucleic acids and vectors of the invention are particularly useful for providing genetic vaccines, i.e. vaccines for delivering the nucleic acids encoding the antigens of the invention to a subject, such as a human, such that the antigens are then expressed in the subject to elicit an immune response.

The compositions of the invention may be injectable suspensions, solutions, sprays, lyophilized powders, syrups, elixirs and the like. Any suitable form of composition may be used. To prepare such a composition, a nucleic acid or vector of the invention, having the desired degree of purity, is mixed with one or more pharmaceutically acceptable carriers and/or excipients. The carriers and excipients must be "acceptable" in the sense of being compatible with the other ingredients of the composition. Acceptable carriers, excipients, or stabilizers are nontoxic to recipients at the dosages and concentrations employed, and include, but are not limited to, water, saline, phosphate buffered saline, dextrose, glycerol, ethanol, or combinations thereof, buffers such as phosphate, citrate, and other organic acids; antioxidants including ascorbic acid and methionine; preservatives (such as octadecyldimethylbenzyl ammonium chloride; hexamethonium chloride; benzalkonium chloride, benzethonium chloride; phenol, butyl or benzyl alcohol; alkyl parabens such as methyl or propyl paraben; catechol; resorcinol; cyclohexanol; 3-pentanol; and m-cresol); low molecular weight (less than about 10 residues) polypeptide; proteins, such as serum albumin, gelatin, or immunoglobulins; hydrophilic polymers such as polyvinylpyrrolidone; amino acids such as glycine, glutamine, asparagine, histidine, arginine, or lysine; monosaccharides, disaccharides, and other carbohydrates including glucose, mannose, or dextrins; chelating agents such as EDTA; sugars such as sucrose, mannitol, trehalose or sorbitol; salt-forming counter-ions such as sodium; metal complexes (e.g., Zn-protein complexes); and/or non-ionic surfactants such as TWEEN® PLURONICS® or polyethylene glycol (PEG).

An immunogenic or immunological composition can also be formulated in the form of an oil-in-water emulsion. The oil-in-water emulsion can be based, for example, on light liquid paraffin oil (European Pharmacopea type); isoprenoid oil such as squalane, squalene, EICOSANE™ or tetratetracontane; oil resulting from the oligomerization of alkene(s), e.g., isobutene or decene; esters of acids or of alcohols containing a linear alkyl group, such as plant oils, ethyl oleate, propylene glycol di(caprylate/caprate), glyceryl tri (caprylate/caprate) or propylene glycol dioleate; esters of branched fatty acids or alcohols, e.g., isostearic acid esters. The oil advantageously is used in combination with emulsifiers to form the emulsion. The emulsifiers can be nonionic surfactants, such as esters of sorbitan, mannide (e.g., anhydromannitol oleate), glycerol, polyglycerol, propylene glycol, and oleic, isostearic, ricinoleic, or hydroxystearic acid, which are optionally ethoxylated, and polyoxypropylene-polyoxyethylene copolymer blocks, such as the Pluronic® products, e.g., L121. The adjuvant can be a mixture of emulsifier(s), micelle-forming agent, and oil such as that which is commercially available under the name Provax® (IDEC Pharmaceuticals, San Diego, Calif.).

The immunogenic compositions of the invention can contain additional substances, such as wetting or emulsifying agents, buffering agents, or adjuvants to enhance the effectiveness of the vaccines (Remington's Pharmaceutical Sciences, 18th edition, Mack Publishing Company, (ed.) 1980).

Adjuvants may also be included. Adjuvants include, but are not limited to, mineral salts (e.g., $AlK(SO_4)_2$, $AlNa(SO_4)_2$, $AlNH(SO_4)_2$, silica, alum, $Al(OH)_3$, $Ca_3(PO_4)_2$, kaolin, or carbon), polynucleotides with or without immune stimulating complexes (ISCOMs) (e.g., CpG oligonucleotides, such as those described in Chuang, T. H. et al, (2002) J. Leuk. Biol. 71(3): 538-44; Ahmad-Nejad, P. et al (2002) Eur. J. Immunol. 32(7): 1958-68; poly IC or poly AU acids, polyarginine with or without CpG (also known in the art as IC31; see Schellack, C. et al (2003) Proceedings of the 34th Annual Meeting of the German Society of Immunology; Lingnau, K. et al (2002) Vaccine 20(29-30): 3498-508), JuvaVax® (U.S. Pat. No. 6,693,086), certain natural substances (e.g., wax D from *Mycobacterium tuberculosis*, substances found in *Cornyebacterium parvum, Bordetella pertussis*, or members of the genus *Brucella*), flagellin (Toll-like receptor 5 ligand; see McSorley, S. J. et al (2002) J. Immunol. 169(7): 3914-9), saponins such as QS21, QS17, and QS7 (U.S. Pat. Nos. 5,057,540; 5,650,398; 6,524,584; 6,645,495), monophosphoryl lipid A, in particular, 3-de-O-acylated monophosphoryl lipid A (3D-MPL), imiquimod (also known in the art as IQM and commercially available as Aldara®; U.S. Pat. Nos. 4,689,338; 5,238,944; Zuber, A. K. et al (2004) 22(13-14): 1791-8), and the CCR5 inhibitor CMPD167 (see Veazey, R. S. et al (2003) J. Exp. Med. 198: 1551-1562). Aluminum hydroxide or phosphates(alum) are commonly used at 0.05 to 0.1% solution in phosphate buffered saline. Other adjuvants that can be used, especially with DNA vaccines, are cholera toxin, especially CTA1-DD/ISCOMs (see Mowat, A. M. et al (2001) J. Immunol. 167(6): 3398-405), polyphosphazenes (Allcock, H. R.

(1998) App. Organometallic Chem. 12(10-11): 659-666; Payne, L. G. et al (1995) Pharm. Biotechnol. 6: 473-93), cytokines such as, but not limited to, IL-2, IL-4, GM-CSF, IL-12, IL-15 IGF-1, IFN-α, IFN-β, and IFN-γ (Boyer et al., (2002) J. Liposome Res. 121:137-142; WO01/095919), immunoregulatory proteins such as CD40L (ADX40; see, for example, WO03/063899), and the CD1a ligand of natural killer cells (also known as CRONY or α-galactosyl ceramide; see Green, T. D. et al, (2003) J. Virol. 77(3): 2046-2055), immunostimulatory fusion proteins such as IL-2 fused to the Fc fragment of immunoglobulins (Barouch et al., Science 290:486-492, 2000) and co-stimulatory molecules B7.1 and B7.2 (Boyer), all of which can be administered either as proteins or in the form of DNA, in the same viral vectors as those encoding the antigens of the invention or on separate expression vectors. Alternatively, vaccines of the invention may be provided and administered without any adjuvants.

The immunogenic compositions can be designed to introduce the CMV vectors to a desired site of action and release it at an appropriate and controllable rate. Methods of preparing controlled-release formulations are known in the art. For example, controlled release preparations can be produced by the use of polymers to complex or absorb the immunogen and/or immunogenic composition. A controlled-release formulation can be prepared using appropriate macromolecules (for example, polyesters, polyamino acids, polyvinyl, pyrrolidone, ethylenevinylacetate, methylcellulose, carboxymethylcellulose, or protamine sulfate) known to provide the desired controlled release characteristics or release profile. Another possible method to control the duration of action by a controlled-release preparation is to incorporate the active ingredients into particles of a polymeric material such as, for example, polyesters, polyamino acids, hydrogels, polylactic acid, polyglycolic acid, copolymers of these acids, or ethylene vinylacetate copolymers. Alternatively, instead of incorporating these active ingredients into polymeric particles, it is possible to entrap these materials into microcapsules prepared, for example, by coacervation techniques or by interfacial polymerization, for example, hydroxymethylcellulose or gelatin-microcapsule and poly-(methylmethacrylate) microcapsule, respectively, in colloidal drug delivery systems (for example, liposomes, albumin microspheres, microemulsions, nano-particles and nanocapsules) or in macroemulsions. Such techniques are disclosed in New Trends and Developments in Vaccines, Voller et al. (eds.), University Park Press, Baltimore, Md., 1978 and Remington's Pharmaceutical Sciences, 16th edition.

Suitable dosages of the CMV vectors in the immunogenic compositions can be readily determined by those of skill in the art. For example, the dosage of the CMV vectors can vary depending on the route of administration and the size of the subject. Suitable doses can be determined by those of skill in the art, for example by measuring the immune response of a subject, such as a laboratory animal, using conventional immunological techniques, and adjusting the dosages as appropriate. Such techniques for measuring the immune response of the subject include but are not limited to, chromium release assays, tetramer binding assays, IFN-γ ELISPOT assays, IL-2 ELISPOT assays, intracellular cytokine assays, and other immunological detection assays, e.g., as detailed in the text "Antibodies: A Laboratory Manual" by Ed Harlow and David Lane.

The immunogenic compositions can be administered using any suitable delivery method including, but not limited to, intramuscular, intravenous, intradermal, mucosal, and topical delivery. Such techniques are well known to those of skill in the art. More specific examples of delivery methods are intramuscular injection, intradermal injection, and subcutaneous injection. However, delivery need not be limited to injection methods.

Immunization schedules (or regimens) are well known for animals (including humans) and can be readily determined for the particular subject and immunogenic composition. Hence, the immunogens can be administered one or more times to the subject. Preferably, there is a set time interval between separate administrations of the immunogenic composition. While this interval varies for every subject, typically it ranges from 10 days to several weeks, and is often 2, 4, 6 or 8 weeks. For humans, the interval is typically from 2 to 6 weeks. In a particularly advantageous embodiment of the present invention, the interval is longer, advantageously about 10 weeks, 12 weeks, 14 weeks, 16 weeks, 18 weeks, 20 weeks, 22 weeks, 24 weeks, 26 weeks, 28 weeks, 30 weeks, 32 weeks, 34 weeks, 36 weeks, 38 weeks, 40 weeks, 42 weeks, 44 weeks, 46 weeks, 48 weeks, 50 weeks, 52 weeks, 54 weeks, 56 weeks, 58 weeks, 60 weeks, 62 weeks, 64 weeks, 66 weeks, 68 weeks or 70 weeks.

The immunization regimes typically have from 1 to 6 administrations of the immunogenic composition, but may have as few as one or two or four. The methods of inducing an immune response can also include administration of an adjuvant with the immunogens. In some instances, annual, biannual or other long interval (5-10 years) booster immunization can supplement the initial immunization protocol.

The present methods also include a variety of prime-boost regimens, for example DNA prime-Adenovirus boost regimens. In these methods, one or more priming immunizations are followed by one or more boosting immunizations. The actual immunogenic composition can be the same or different for each immunization and the type of immunogenic composition (e.g., containing protein or expression vector), the route, and formulation of the immunogens can also be varied. For example, if an expression vector is used for the priming and boosting steps, it can either be of the same or different type (e.g., DNA or bacterial or viral expression vector). One useful prime-boost regimen provides for two priming immunizations, four weeks apart, followed by two boosting immunizations at 4 and 8 weeks after the last priming immunization. It should also be readily apparent to one of skill in the art that there are several permutations and combinations that are encompassed using the DNA, bacterial and viral expression vectors of the invention to provide priming and boosting regimens. In the event that the viral vectors express US2-11 or some of the genes encoded in the US2-11 region they can be used repeatedly while expressing different antigens derived from different pathogens.

A specific embodiment provides methods of inducing an immune response against a pathogen in a subject by administering an immunogenic composition one or more times to a subject wherein the epitopes are expressed at a level sufficient to induce a specific immune response in the subject. Such immunizations can be repeated multiple times at time intervals of at least 2, 4 or 6 weeks (or more) in accordance with a desired immunization regime.

The immunogenic compositions of the invention can be administered alone, or can be co-administered, or sequentially administered, with other antigens, e.g., with "other" immunological, antigenic or vaccine or therapeutic compositions thereby providing multivalent or "cocktail" or combination compositions of the invention and methods of employing them. Again, the ingredients and manner (sequential or co-administration) of administration, as well as dosages can be determined taking into consideration such factors as the age, sex, weight, species and condition of the particular subject, and the route of administration.

When used in combination, the other antigens can be administered at the same time or at different times as part of an overall immunization regime, e.g., as part of a prime-boost regimen or other immunization protocol.

Although the present invention and its advantages have been described in detail, it should be understood that various changes, substitutions and alterations can be made herein without departing from the spirit and scope of the invention as defined in the appended claims.

EXAMPLES

The following examples are illustrative of disclosed methods. In light of this disclosure, those of skill in the art will recognize that variations of these examples and other examples of the disclosed method would be possible without undue experimentation.

Example 1—Immunization with RhCMV Vectors with a Deletion of UL128 and UL130 Result in an Immune Response Characterized by a Wide Variety of CD8+ T-Cell Epitopes Against an SIV Antigen Epitope targeting profiles of SIVgag-specific CD8$^+$ T cell responses elicited by RhCMV/gag vectors derived from RhCMV 68-1 strain, lacking active UL128 and UL130 ($\Delta$UL128-130), but comprising an active UL131 (Hansen, S G et al, *J Virol* 77, 6620 (2003); incorporated by reference herein) were compared to those elicited by more conventional vectors as well as by SIV itself. Flow cytometric intracellular cytokine staining was used to individually quantify CD8+ T cell responses to each of 125 consecutive 15mer peptides (with 11 amino acid overlap) covering the entire SIVgag protein. A total of twenty-nine rhesus macaques (RM) were used: fourteen were vaccinated with $\Delta$UL128-130 RhCMV/gag vector. Four were vaccinated with electroporated DNA/gag+ interleukin (IL)-12. Three were vaccinated with adenovirus (Ad)5/gag and another three with vaccinia virus (MVA)/gag. Another five animals were previously SIV-infected (SIVmac239) with spontaneous viral control.

Peripheral blood CD8$^+$ T cells from $\Delta$UL128-130 RhCMV/gag vector-vaccinated RM responded to an average of 46 of the 125 15mer SIVgag peptides tested. This corresponded to an average of about 35 distinct epitopes (FIG. 1A). In contrast, SIV-infected controllers and RM vaccinated with electroporated DNA/gag+IL-12, Ad5/gag and MVA/gag responded to an average of 10-19 peptides, corresponding to an average of 9-15 distinct epitopes. The breadth of the responses in the $\Delta$UL128-130 RhCMV/gag vector-vaccinated RM was so great that many of the SIVgag 15mer peptides were targeted by CD8+ T cells in most or even all of 14 outbred animals studied (FIG. 1A).

Figure 1B:
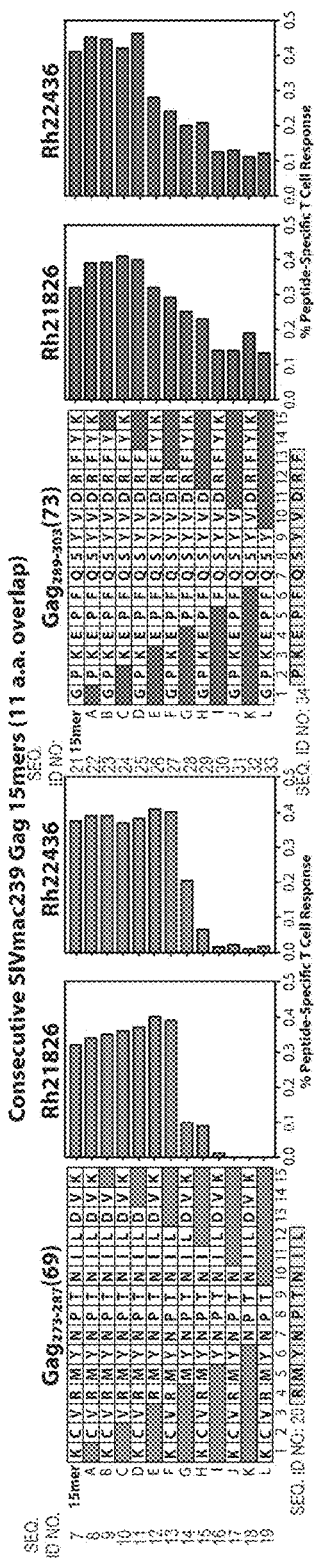

To determine whether this finding reflects promiscuous recognition of a single common epitope ("supertope") or simply T cell recognition "hotspots" (multiple overlapping, but different, epitopes), the response to a series of truncated peptides was analyzed. These truncated peptides corresponded to 7 of the 15mers recognized in 3 RM per response. They were then used to identify core epitopes in each RM (FIG. 1B).

Figure 1C:
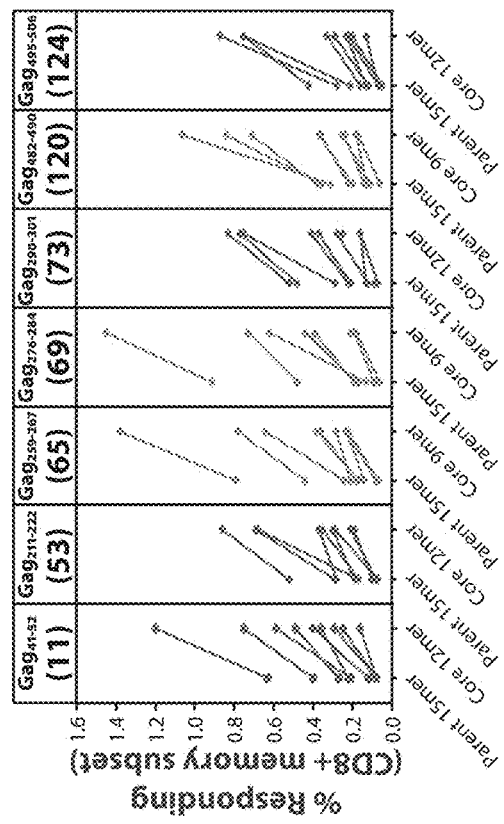

Two distinct response patterns were observed using the truncated peptides: A first type of response pattern, called Type 1 herein, is defined as a pattern in which response frequencies dropped abruptly with loss of a critical amino residue. These truncations typically resulted in a 9mer core epitope (e.g. $Gag_{259-267}$, $Gag_{276-284}$, and $Gag_{482-490}$). A second type of response, called Type 2 herein is defined as a pattern in which response frequencies gradually decline as the optimal sequence was truncated. These truncations typically resulted in a 12mer core epitope ($Gag_{41-52}$, $Gag_{211-222}$, $Gag_{290-301}$, $Gag_{495-506}$). These truncation response patterns and core peptides were the same in all RM studied for each response, and in all cases, the core peptides manifested superior stimulation (higher response frequencies) than the parent 15mer (FIG. 1C).

Figure 1D:
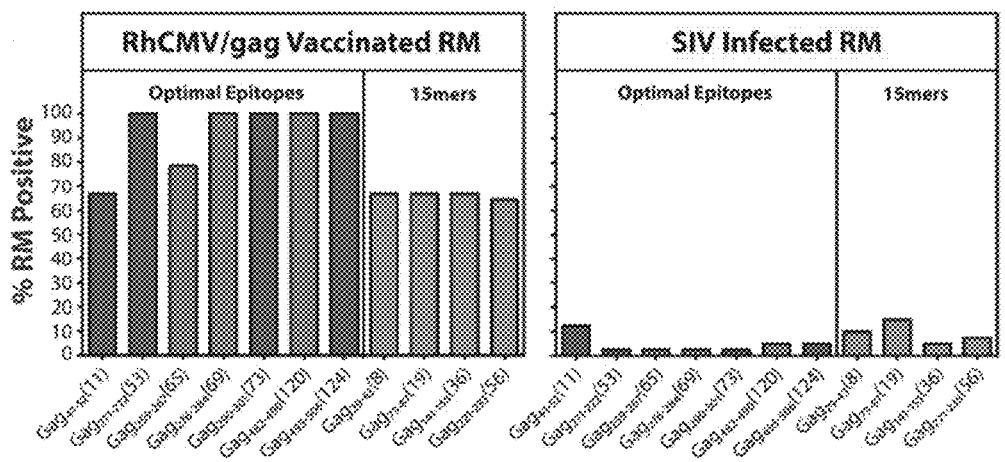

Taken together, these data strongly suggest that many of the SIVgag epitopes targeted by CD8$^+$ T cells in $\Delta$UL128-130 RhCMV/gag vector-vaccinated RM are specific determinants that are commonly or even universally recognized across disparate MHC haplotypes. Indeed, a detectable CD8$^+$ T cell response to the core (optimal) peptide for 5 of these truncated 15mers (including both Type 1 and 2 truncation patterns) was found in 100% of 42 RhCMV/gag-vaccinated outbred RM and responses to 6 other peptides (two optimal peptides and four 15mers) were found in >60% of RM, respectively (FIG. 1D). Notably, these epitopes were rarely recognized by CD8+ T cells in conventionally SIV-infected RM. Thus, $\Delta$UL128-130 RhCMV/gag vector-elicited CD8+ T cell responses to SIVgag are ~3-fold as broad as conventionally infected SIVgag-specific CD8+ T cell responses and are uniquely characterized by frequent targeting of broadly recognized "supertopes".

Example 2—Type 1 CD8+ Responses are MHC-I Restricted, Type 2 CD8+ Responses are MHC-II Restricted MHC-I-restricted epitopes are typically 8-10 amino acids in length and have position-specific amino acids that engage binding pockets (anchor residues) so as to fit in a "closed end" MHC-1 binding groove (Rammensee H G et al, Ann Rev Immunol 11, 213 (1993); incorporated by reference herein) characteristics consistent with the Type 1 truncation pattern described above. In contrast, the Type 2 truncation pattern is more typical of MHC II-restricted epitopes (which are typically longer, usually a >12mer core, lack specific anchor residues, and are more tolerant of length heterogeneity (Southwood S et al, *J Immunol* 160, 3363 (1998) and Chelvanayagam G, *Hum Immunol* 58, 61 (1997); both of which are incorporated by reference herein). This suggested that the CD8$^+$ T cells recognizing Type 2 SIVgag epitopes in the RhCMV/gag vector-vaccinated RM might be MHC-II-restricted. In this regard, while class II-restricted CD8 T cell responses are clearly unusual, such responses have been previously reported in both mice (Mizuochi T et al, *J Exp Med* 168, 437 (1988); Suzuki H et al, *J Immunol* 153, 4496 (1994); Matechak E O et al, *Immunity* 4, 337 (1996); Shimizu T and Takeda S, *Eur J Immunol* 27, 500 (1997); Tyznik A J et al, *J Exp Med* 199, 559 (2004); Pearce E L et al, *J Immunol* 173, 2494 (2004); all of which are incorporated by reference herein) and in humans (Heemskerk M H et al, *Proc Nat/Acad Sci USA* 98, 6806 (2001); Rist M et al, *Blood* 114, 2244 (2009); Hirosawa T et al, *Cancer Sci* 102, 1281 (2011); all of which are incorporated by reference herein) and it has been established that productive TCR signaling does not require specific CD4 or CD8 co-receptor engagement with MHC-II or MHC-I, respectively (Viola A et al, *J Exp Med* 186, 1775 (1997) and Lustgarten J et al, *Eur J Immunol* 21, 2507 (1991); both of which are incorporated by reference herein).

To investigate the possibility that ΔUL128-130 RhCMV-gag was eliciting an MHC-II-restricted CD8+ T cell response to gag, the ability of "blocking" monoclonal antibodies (mAbs) specific for MHC-I and MHC-II as well as the invariant chain-derived, MHC-II-specific binding peptide CLIP (Sette A, *J Exp Med* 181, 677 (1995); incorporated by reference herein) to block the Type 1 and Type 2 epitope-specific CD8+ T cell responses in RM immunized with ΔUL128-130 RhCMVgag was assessed (FIG. 2A). Inhibition of the 5 universal supertope-specific CD8+ T cell responses by these reagents corresponded precisely to the Type 1 vs. 2 truncation pattern, with T cell recognition of the three Type 2 epitopes ($Gag_{211-222}$, $Gag_{290-301}$, $Gag_{495-506}$) blocked by anti-MHC-II and CLIP, but not anti-MHC-I, and the reverse for T cell recognition of the 2 Type 1 epitopes ($Gag_{276-284}$, $Gag_{482-490}$).

The epitope specific responses mapped in FIG. 2A with respect to MHC-I vs. MHC-II blockade (FIG. 2B, FIG. 2C). As expected, all CD8+ T cell responses in the SIV-infected RM and the RM vaccinated with the conventional vaccines were only blocked with reagents targeting MHC-I, whereas in the ΔUL128-130 RhCMV/SIV-vaccinated RM, the CD8+ T cell response to the majority of the targeted 15mers (61%) were specifically blocked by the MHC-II inhibitors, leaving a minority (36%) blocked only by MHC-I mAbs (with ~3% of responses indeterminate).

Figure 3A:
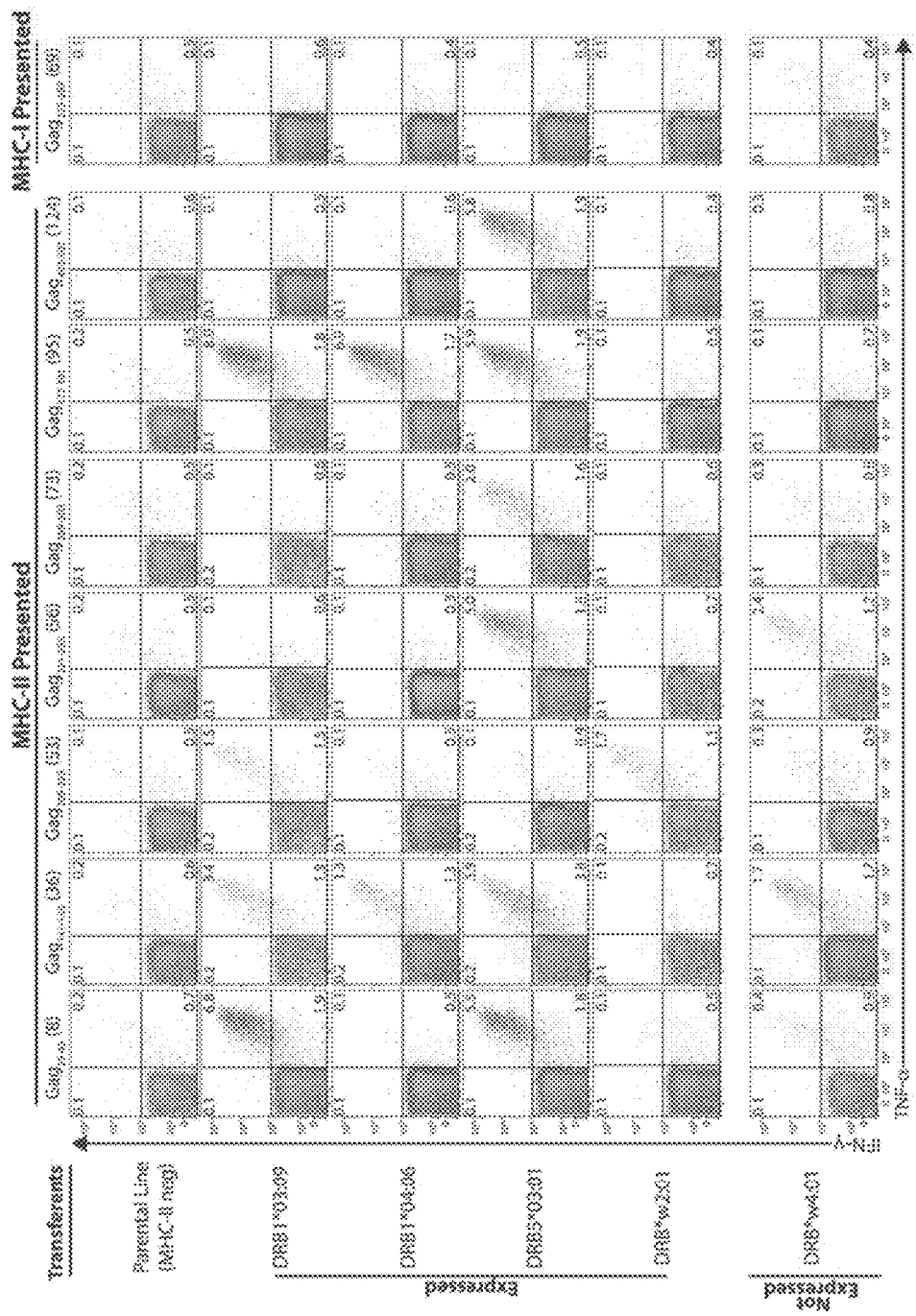

To confirm that the MHC-II-blocked CD8+ T cell responses were MHC-II-restricted—defined as the epitope in question being recognized in the context of MHC-II—and to investigate the basis of the promiscuity of these responses across MHC-disparate RM, cell lines expressing single rhesus MHC-II allomorphs were constructed. The MHC-II alleles selected were expressed by 4 RhCMV/gag-vaccinated RM with characterized SIVgag epitope recognition profiles. Flow cytometric ICS assays showed that pulsing of the MHC-II allomorph transfectants, but not the parental MHC-II negative cell line, with individual peptides resulted in robust CD8+ T cell stimulation of only those responses classified as MHC-II-associated by blocking experiments (FIG. 3A), and these responses could be blocked with anti-MHC-II mAbs and CLIP peptide, but not anti-MHC-I mAbs. Importantly, individual MHC-II allomorphs presented multiple peptides, and individual peptides were frequently presented by multiple MHC-II allomorphs (FIG. 3A). The ability of individual allomorphs to present multiple gag peptides helps explain the breadth of these MHC-II-restricted responses. The ability of multiple MHC-II allomorphs to present many of the individual peptides suggests that the common recognition of these peptides by RhCMV/gag vector-elicited CD8+ T cells across MHC-disparate RM (e.g., their supertope character) is likely explained by all RM expressing at least one effective MHC-II allomorph for each response.

Figure 3B:
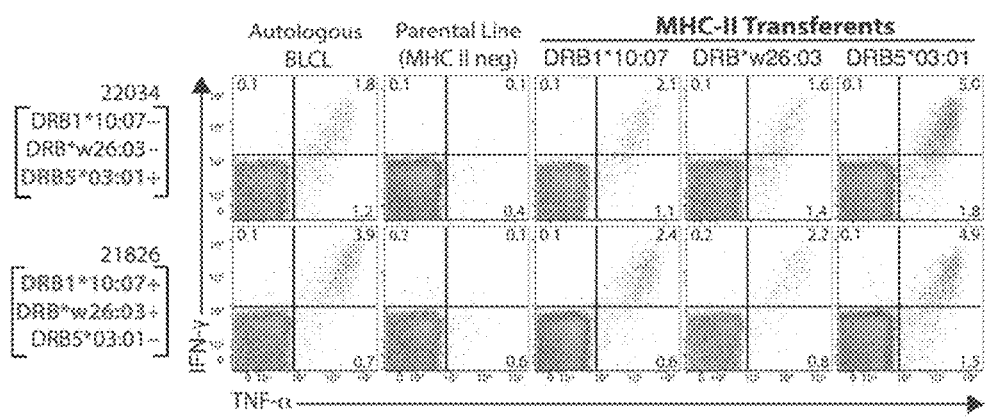

As has been previously reported for MHC-II-restricted CD4+ T cell responses (Corradin C and Lanzaveccia A, *Int Rev Immunol* 7, 139 (1991); incorporated by reference herein) MHC-II-restricted, SIVgag-specific CD8+ T cells elicited by RhCMV/gag vectors can respond to their specific peptide epitope in the context of peptide-binding MHC-II allomorphs that are not expressed by the T cell donor (FIGS. 3A and 3B), indicating that the TCR of these T cells recognize the bound peptide alone or in combination with non-polymorphic structures on the MHC-II molecule.

Example 3—Phenotype and Function of ΔUL128-130 RhCMV/SIV Vector-Elicited CD8+ T Cell Responses The unusual epitope specificity of the SIV-specific CD8 T cells generated and maintained by RhCMV/SIV vector vaccination raises the question of their functional potential, especially the unconventional MHC-II-restricted population that dominates these responses. First, in this regard, these supertope-specific CD8 T cell responses are not an artifact of the high peptide concentrations used in standard ICS assays, as responses to the optimal peptides, both Type 1 and Type 2, can be demonstrated at peptide dilutions of $1:10^5$ and greater (FIG. 4A). Second, Type 1 and Type 2 supertope-specific responses arise immediately after vaccination (FIG. 4B) and are coordinately distributed throughout the body in the pattern previously reported for RhCMV/SIV vector-vaccinated RM (Hansen S G et al, *Nature* 473, 523 (2011); incorporated by reference herein (FIGS. 4C and 4D). Third, as previously reported for RhCMV-specific CD8+ T cells and RhCMV/SIV vector-elicited SIV-specific T cells (Hansen S G et al, *Nat Med* 15, 293 (2009); incorporated by reference herein); both Type 1 and Type 2 supertope-specific T cells manifest an identical phenotype indicative of effector memory T cell differentiation ($CCR7^-$, $CD28^-$) and an identical polyfunctional profile consistent with this effector-memory phenotype—high TNF, IFN-γ, and MIP-1α production, high CD107 externalization (degranulation) and low IL-2 production (FIGS. 4E and 4F). Since effector memory differentiation is thought to be Ag-driven, these data suggest that in vaccinated RM, these CD8+ T cells receive equivalent in vivo exposure to Type 1 and Type 2 epitopes.

Example 4—UL128 and UL130 Control Targeting of CMV-Elicited CD8+ T Cell Responses To identify candidate CMV genes associated with, and potentially responsible for, this unusual CD8+ immune response, it was first asked whether CD8+ T cell responses to an endogenous CMV immediate early (IE) protein also target unconventional epitopes (in particular, supertopes restricted by MHC-II). This was determined by assessing RM naturally infected with wildtype RhCMV (colony circulating strains) and RM vaccinated with the exemplary ΔUL128-130 deficient strain 68.1 RhCMV/SIV vector. Not surprisingly, RM vaccinated with the ΔUL128-130 vector demonstrated IE-specific CD8+ T cell responses with identical targeting characteristics as the SIVgag-specific CD8+ T cell responses in the same RM: >30 distinct IE epitopes/RM, including a majority of epitope-specific responses that were blocked with anti-MHC-II, and a minority blocked with anti-MHC-I.

However, in striking contrast, the IE-specific CD8+ T cell responses in naturally RhCMV-infected RM were much more narrowly targeted (~8 epitopes/RM), and showed no evidence of MHC-II restriction or epitope promiscuity (FIGS. 5A, 5B, and 5C), consistent with conventional immunodominance hierarchies. These findings likely account for why unconventionally targeted CMV-specific CD8+ T cell responses have not been reported in naturally exposed CMV+ RM and humans (despite considerable analysis of these responses) and more importantly, implicate genetic differences between the ΔUL128-130 deficient strain 68.1-based RhCMV vectors and ΔUL128-130 containing wildtype RhCMV in the mechanism(s) responsible for generating the unconventionally targeted CD8+ T cell responses.

To assess the role of these genes in the targeting of CD8+ T cells during priming, a RhCMV/gag vector was generated in which expression of the UL128 and UL130 orthologs was re-established (Lilja A E et al, *Proc Natl Acad Sci USA* 105, 19950 (2008). It was then asked whether this "repair" of the UL128 and UL130 ortholog expression changed the epitope targeting profiles of vector-elicited gag-specific CD8+ T cell responses. Indeed, the UL128 and UL130-repaired RhCMV/gag vector-elicited SIVgag-specific CD8+ T cell responses that did not include recognition of any of the previously defined MHC-I or MHC-II supertopes, were much more narrowly targeted than the response elicited by the unrepaired 68.1 strain vector (lacking UL128-UL130 orthologue expression), and were entirely MHC-I-associated (FIGS. 5D, 5E, and 5F).

Example 5—CMV Vectors with Single Deletions of UL128 or UL130 Display CD8 Responses Characterized by Class II Restriction, CMV Vectors with a Single Deletion of UL131 is Incapable of Superinfection The RhCMV strain 68.1 was multiply passaged in fibroblast culture prior to its use in RhCMV/SIV vector construction and differs from the original field isolate by lacking part of the UL130 gene and the entire UL128 gene (Gill et al, *Virology* 447, 208 (2013); incorporated by reference herein). The genes for UL128 and UL130 are encoded on a single mRNA together with UL131 in the order 5'-UL131-UL130-UL128-3' (Lilja A E et al, 2008 supra. Since all three genes are encoded by this single "poly-cistronic" mRNA and since the entire 3' end of this mRNA is missing in 68-1 it was previously thought in Hansen S G et al, *Science* 340, 1237874 doi, 24 May 2013 (incorporated by reference herein) that 68.1 lacks might expression of all three active RhCMV orthologues of HCMV UL128, 130 and 131 genes (Rh157.6, 157.4 and 157.5). To determine the individual function of UL128, UL130 and UL131 in modulating the priming of MHC-II-restricted CD8+ T cells we generated RhCMV/SIVgag vectors lacking each of these genes individually. Using the UL128-130 "repaired" RhCMV-68-1.2 virus (Lilja et al 2008 supra) as our starting point we generated ΔUL128RhCMV/gag, ΔUL130/RhCMVgag and ΔUL131/RhCMVgag and inoculated each of these constructs into two RM that were already naturally infected with RhCMV. As shown in FIG. 6, RhCMV lacking UL128 but containing UL130 and UL131 induced a T cell response to SIVgag in both animals. Similarly, RhCMV lacking UL130 but containing UL131 and UL128 induced a T cell response to SIVgag in both animals. In contrast, RhCMV lacking UL131 but containing intact genes for UL130 and UL128 was unable to induce an immune response in CMV-positive animals. These data suggest that a functional UL131 gene is required for super-infection of CMV-positive animals. Since RhCMV 68-1 is capable of super-infection this result also demonstrates that RhCMV 68-1 contains a functional UL131 despite the deletion of part of the polycistronic mRNA consistent with RhCMV 68-1 being a ΔUL128-130 vector. To further determine whether vectors carrying single deletions of UL130 or UL128 would elicit MHC-II restricted CD8+ T cells we monitored the CD8+ T cell response to 25 overlapping 15mer peptides corresponding to the amino-terminal part of SIVgag in the presence of MHC-I or MHC-II-blocking antibodies. As shown in FIG. 7, both MHC-I and MHC-II restricted CD8+ T cell responses were observed to individual peptides. These results demonstrate that single deletion vectors lacking either UL128 or UL130 but containing UL131 are capable of inducing unconventional T cell responses.

Example 6—CMV Vectors with a ΔUL128-130 Deletion Comprising *Mycobacterium tuberculosis* Antigens Display CD8 Responses Characterized by Class II Restriction In above examples we demonstrated that vectors lacking UL128 and/or UL130 induce unconventional CD8+ T cells restricted by MHC-II rather than the more commonly observed MHC-I against viral antigens such as the CMV-IE protein or the SIVgag protein. To determine whether ΔUL128-130 vectors are also capable of inducing MHC-II restricted CD8+ T cells to bacterial antigens we inserted a fusion protein of two *Mycobacterium tuberculosis* antigens into ΔUL128-130 vectors. The resulting vector RhCMV/TB encodes a 50 kDa fusion protein of *Mycobacterium tuberculosis* ESAT6 and antigen 85B (Derrick S C et al, *Vaccine* 23, 780-788 (2004); incorporated by reference herein). ESAT6 is an early secretory protein whereas Antigen 85B binds and is the most abundant protein expressed by *Mycobacterium tuberculosis* (Brandt, *J Immunol* 157, 3527 (1996) incorporated by reference herein). Three RM were inoculated with RhCMV68-1-derived vector RhCMV/TB and the CD8+ T cell response to individual peptides was monitored in the presence of antibodies blocking MHC-I or MHC-II. As shown in FIG. 8 each of the vaccinated animals developed CD8+ T cell responses to both antigens with some of the CD8+ T cells being restricted by MHC-I whereas others were restricted by MHC-II. These data thus demonstrate that the ability to induce MHC-II restricted CD8+ T cells by CMV vectors lacking UL128 and UL130 is not confined to viral antigens but can be expanded to other heterologous antigens, including bacterial antigens.

Example 7 Sequential Inoculation of UL128-130-Deleted and UL128-130-Containing Vectors Increases Epitope Coverage of Heterologous Antigens In the examples above we demonstrated that vectors lacking UL128-130 induce both MHC-I and MHC-II-restricted CD8+ T cells whereas vectors with UL128-130 intact only induce MHC-I restricted CD8+ T cells. To determine whether sequential inoculation by vectors carrying the same antigen but differing with respect to the presence of UL128 and UL130 we sequentially inoculated two RM previously vaccinated with ΔUL128-130 (68-1) with another round of ΔUL128-130 (68-1) followed by UL128-130 "repaired" (68-1.2) RhCMV vectors. All vectors expressed SIVgag. While the overall CD8+ T cell response to SIVgag was boosted by both re-vaccination with the ΔUL128-130 (68-1 derived) and the UL128-130 repaired (68-1.2 derived) vectors, responses to individual peptides present in each animal due to previous vaccination with 68-1/SIVgag vectors were boosted by 68-1/SIVgag vectors, but not by 68-1.2/SIVgag vectors (FIG. 9, upper panel). Since the individual peptides were recognized by CD8+ T cells restricted by either MHC-I and MHC-II these data demonstrate that the epitope spectrum induced by vectors lacking UL128 and UL130 does not overlap with that of vectors containing intact UL128 and UL130 even for MHC-I restricted T cells. This result further suggested that sequential vaccination of the same individual with UL128/130-deleted and UL128-130-intact vectors carrying the same antigen will induce a much broader T cell response compared to inoculation with single vectors. This conclusion was supported when CD8+ T cell responses against individual SIVgag epitopes were monitored in these two RM after single vaccination with 68-1/gag, re-vaccination with 68-1/gag and vaccination with 68-1.2/gag. As shown in the lower panel of FIG. 9, both revaccination with the same type of vector and vaccination with a vector that differs in its UL128-130 composition induced new T cells recognizing additional SIVgag epitopes while maintaining the T cell responses from previous vaccinations. By taking into consideration that each of the core epitopes is 9-12 amino-acids in length and that SIVgag encodes 510 amino-acids, the 45-52 epitopes induced by the sequential vaccination strategy in these animals represent coverage of about 90% of the entire SIVgag polypeptide sequence. To our knowledge, this level of epitope coverage has not been observed previously with any other vector system.

Example 8—Materials and Methods

Animals:

A total of 165 purpose-bred male or female juvenile rhesus macaques (*Macaca mulatta*) of Indian genetic background were used in this study, including 110 macaques vaccinated with strain 68-1 RhCMV/SIV vectors (wild-type or genetically modified, alone or subsequent to heterologous priming with conventional vaccines or virally suppressed SIV infection), 47 macaques with SIV infection alone (SIV-mac239 or SIVmac251), and 8 unvaccinated macaques that were naturally infected with colony-circulating strains of RhCMV. All macaques were used with the approval of the Oregon National Primate Research Center Institutional Animal Care and Use Committee, under the standards of the NIH Guide for the Care and Use of Laboratory Animals. Macaques used in these experiments were free of cercopithicine herpesvirus 1, D-type simian retrovirus, and simian T-lymphotrophic virus type 1. MHC-I genotyping for the Mamu-A*01, Mamu-A*02, Mamu-B*08, and Mamu-B*17 alleles was performed by sequence-specific priming polymerase chain reaction (PCR), as described in Loffredo J T et al, *J Virol* 81, 8827 (2007); incorporated by reference herein. Selected macaques were DRB-genotyped by deep sequencing. Briefly, amplicons of the Mamu-DRB region were created via amplification of cDNA by PCR with high-fidelity Phusion® polymerase (NEBiolabs) and a pair of universal MHC-DRB-specific primers (5'-CGTATCGCCTC-CCTCGCGCCATCAG (SEQ ID NO: 1)-MID-CTGGTC-CTGTCCTGTTCTCC (SEQ ID NO: 2); 5'-CTATGCGC-CTTGCCAGCCCGCTCAG (SEQ ID NO: 3)-MID-TGGAAGGTCCAGTCTCCATT (SEQ ID NO:4)) using the following thermocycling conditions: 98° C. for 3 min, (98° C. for 5 s, 60° C. for 10 s, 72° C. for 20 s) for 25 cycles, and 72° C. for 5 min. The primary cDNA-PCR products were purified using AMpure XP magnetic beads (Beckman Coulter Genomics). Emulsion PCR using a Lib-A kit (Roche/454 Life Sciences), bead purification, and pyrosequencing procedures with the Roche/454 GS Junior instrument were carried out as per the manufacturer's instructions. Data analysis was performed using a Labkey database in conjunction with Geneious-Pro® bioinformatics software (Biomatters Ltd.) for sequence assembly. Mononuclear cell preparations for immunologic assays were obtained from blood, bone marrow, bronchoalveolar lavage (BAL), lymph nodes, spleen, liver, bone marrow, and intestinal mucosa, as described (Pitcher C J et al, *J Immunol* 168, 29 (2002) and Veazey R S et al, *Science* 280, 427 (1998); both of which are incorporated by reference herein). Purified CD8+ T cells (>90% pure) were obtained from PBMCs using CD8 microbeads and LS columns (Miltenyi Biotec). Plasma viral loads of SIV+ macaques were determined by quantitative real-time reverse transcription PCR (RT-PCR) (60). SIV+ macaques were considered SIV controllers if the plasma viral loads were <2.0×10$^4$ copies/ml, and elite controllers if the plasma viral loads were <3.0×10$^3$ copies/ml.

RhCMV/SIV Vectors:

The construction, characterization, and administration of strain 68-1-derived RhCMV/SIV have been described in detail in Hansen S G et al, *Nature* 473, 523 (2011); Hansen S G et al, *Nat Med* 15, 293 (2009) and Hansen S G et al, *Science* 328, 102 (2010); all of which are incorporated by reference herein. All recombinant viruses used in this study were derived from strain RhCMV 68-1 BAC except for RhCMV(gagL), which was generated by replacing green fluorescent protein (GFP) in RhCMV-EGFP with the SIV-gag expression cassette by in vivo recombination in tissue culture. Unlike BAC-derived constructs, RhCMV gagL contains an intact open reading frame (ORF), Rh61/Rh60 (UL36), as described for RhCMV68-1 (Malouli D et al, *J Virol* 86, 8959 (2012) and Hansen S G et al, *J Virol* 77, 6620 (2003); both of which are incorporated by reference herein). As a result of tissue culture adaptation, both BAC and non-BAC RhCMV 68-1 constructs contain a deletion of ORF 157.5 and most of ORF Rh157.4 encoding homologs of HCMV UL128 and UL130, respectively (Oxford K L et al, *Virology* 373, 181 (2008); incorporated by reference herein). In low-passage RhCMV, these two ORFs are translated from the same polycistronic mRNA encompassing Rh157.6 (UL131) (Lilja A E et al, *Proc Natl Acad Sci USA* 105, 19950 (2008); incorporated by reference herein).

To generate a vector with repaired UL128-UL130 expression, the SIVgag expression cassette was inserted into Rh211 of RhCMV68-1.2, a recombinant virus in which Rh61/Rh60 (UL36), Rh157.4 (UL130), and Rh157.5 (UL128) had been repaired. ΔRh182-189 RhCMV/gag has been described in Hansen et al 2010 supra. Similarly ΔRh182-189 RhCMV/rtn and/env by replacing the genomic region encoding Rh182-189 [base pairs 193,161 to 199,823, using the BAC genome annotation in Malouli et al 2012 supra] with the EF1α SIVrev/tat/nef or gH SIV/env expression cassettes. The partial deletion mutants ΔRh182-185 RhCMV/gag and/rtn were generated by replacing base pairs 193,161 and 196,305 with an expression cassette for SIVgag or SIVrev/tat/nef. The partial deletion mutants ΔRh186-189 RhCMV/gag and rtn were constructed by replacing base pairs 196,593 to 199,823 with SIVgag or SIVrev/tat/nef expression cassette. To generate recombinant RhCMV that only lacks Rh189 (US11), we replaced the Rh189 coding region with that of SIVgag in RhCMVrtn. This vector thus expresses SIVgag under control of the Rh189 promoter and SIVrtn (inserted into Rh211) under control of the EF1α promoter (FIG. S10). All of the recombinant viruses were characterized and confirmed by restriction digestion, and the antigen inserts including their flanking regions were sequence-verified. Expression of SIV antigens was verified by immunoblot. Additionally, adjacent gene expression was verified by RT-PCR.

Other Vaccines:

The construction, characterization, and administration of the Ad5/gag vectors used in this study have been described (Hansen et al 2011 supra). MVA/gag was constructed by insertion of codon-optimized, full-length SIVmac239 gag gene into the MVA shuttle vector, pLW44, under the control of MH5, an early/late vaccinia promoter, to generate the recombinant plasmid, pJV7. Flanking sequences within pLW44 directed insertion of the recombinant construct into the thymidine kinase locus by homologous recombination. Chicken embryonic fibroblast cells were transfected with pJV7 followed by infection with MVA strain 1974 to generate recombinant virus expressing SIVmac239 gag (SIV-gag expression confirmed by Western blot). Recombinant virus was plaque-purified and amplified in large-scale culture. Viral stocks were purified over a 24 to 40% sucrose gradient followed by pelleting through a 36% sucrose cushion with the pellet then suspended in 1 mM Tris-Cl, pH 9.0.

For MVA/gag vaccination, macaques were administered 10$^8$ plaque-forming units of this vector via intramuscular injection. The DNA/gag+IL-12 vaccines were provided by Inovio Pharmaceuticals. Briefly, codon-optimized, 5' and 3' halves of the full-length SIVmac239gag were cloned into the pVAX® backbone (Invitrogen) such that the SIVgag insert expression was controlled by the human CMV (HCMV) promoter/enhancer and the bovine growth hormone polyadenylation signal. The optimized rhesus macaque IL-12 adjuvant was constructed via modification of a previously used unoptimized version of macaque IL-12 (63). Modification included codon and RNA optimization of the p35 and p40 insert sequences only, which was carried out by GeneArt® (Invitrogen). Macaques were administered 1 mg of the two SIVgag constructs and 0.5 mg of IL-12 construct with the DNA being delivered into the quadriceps muscle followed by in vivo electroporation using a Cellectra® constant-current device (Inovio Pharmaceuticals Inc.) as described (Laddy D L et al, *J Virol* 83, 4264 (2009); incorporated by reference herein).

Antigens and Antigen Presenting Cells:

The synthesis of sequential 15mer peptides (overlapping by 11 amino acids) comprising the SIVgag, rev, nef, tat, env, and pol proteins and RhCMV IE-1 protein as well as specific 9- to 14mer peptides within these proteins, was performed by Intavis AG®, using the SIVmac239 sequence (GenBank accession number M33262) (Kestler H et al, *Science* 248, 1109 (1990); incorporated by reference herein) or the strain 68-1 RhCMV IE-1 sequence (GenBank accession number AY186194) (Hansen S G et al, *J Virol* 77, 6620 (2003); incorporated by reference herein. All peptides are identified by the position of their inclusive amino acids from the N terminus (e.g., Gag$_{xx-yy}$). Consecutive 15mers are also designated by their 15mer position starting from the N-terminal 15mer (e.g., Gag$_{1-15}$ is 15mer #1; Gag$_{4-19}$ is 15mer #2, etc.). Unless otherwise specified, these peptides were used in T cell assays at 2 µg/ml (whether alone or in pan-protein mixes). Aldrithiol-2-inactivated SIV (AT-2-SIV; lot P4146, AIDS and Cancer Virus Program, Frederick National Laboratory, Frederick, Md.) was produced as described (Buseyne F et al, *Nat Med* 7, 344 (2001); incorporated by reference herein. Autologous B-lymphoblastoid cell lines (BLCL) were generated by infecting rhesus PBMCs with Herpesvirus papio (Voss G et all Virol Methods 39, 185 (1992); incorporated by reference herein. Autologous SIV-infected target cells were produced by spinoculation of activated CD4$^+$ T cells with sucrose-purified SIVmac239, followed by 4 days of culture and then purification with CD4 microbeads and LS columns (Miltenyi Biotec), as described (Sacha J B et al, *J Immunol* 178, 2746 (2007); incorporated by reference herein). Infected cell preparations were >95% CD4+ T cells and >50% SIV-infected after enrichment and were used at an effector:target ratio of 80:1. Construction of single Mamu-DR allomorph transfectants was performed as described (Giraldo-Vela J P et al, *J Virol* 82, 859 (2008); incorporated by reference herein), except that Mamu-DR alleles were inserted into plasmid pCEP4 (Invitrogen) rather than pcDNC3.1. Mamu-DRA*01:05 was paired with DRB1*10:07, DRB1*04:06, DRB1*03:09, DRB5*03:01, DRB*w2:01, and DRB*w26:03; Mamu-DRA*01:021 was paired with DRB*w4:01. Prior to MHC-II restriction assays, mRNA from these transfectants was extracted using the AllPrep® DNA/RNA Mini Kit (Qiagen), amplified by RT-PCR using a universal primer pair (5'-GACACTGATGGTGCTGAGC-3'-SEQ ID NO: 5 and 5'-GCTGCACTGTGAAGCTCTC-3'-SEQ ID NO: 6) that spanned the highly polymorphic β1 region of Mamu-DRB, and its sequence was confirmed. MHC-II transfectants and BLCLs were pulsed with the Gag peptide of interest at a final concentration of 5 µg/ml for 90 min (37° C.), then washed twice with warm PBS and once with warm R10 to remove unbound peptide before being used to stimulate freshly isolated PBMCs at an effector: target ratio of 10:1.

T Cell Assays:

SIV- and RhCMV-specific CD4+ and CD8+ T cell responses were measured in mononuclear cell preparations from blood and tissues by flow cytometric ICS, as described in detail (in Hansen S G et al 2011 supra; Hansen S G et al 2009 supra, and Hansen S G et al, 2010 supra). Briefly, mononuclear cells or isolated CD8+ T cells were incubated with antigen (peptide, AT-2 SIV, peptide-pulsed BLCLs or MHC-II transfectants, or SIV-infected CD4+ T cells) and the costimulatory molecules CD28 and CD49d (BD Biosciences) for 1 hour, followed by addition of brefeldin A (Sigma-Aldrich) for an additional 8 hours. Costimulation without antigen served as a background control. The MHC association (MHC-I versus MHC-II) of a response was determined by preincubating isolated mononuclear cells or APCs for 1 hour at room temperature in the presence of MHC-I mAb (10 µg/ml; clone W6-32) versus MHC-II mAb (HLA-DR; clone G46-6) or CLIP peptide (MHC-II-associated invariant chain, amino acids 89 to 100; 2 µg/ml) before adding peptides or combining effector and target cells and incubating per the standard ICS assay. Stimulated cells were fixed, permeabilized, and stained as described in Hansen S G et al 2011 supra; Hansen S G et al 2009 supra, and Hansen S G et al, 2010 supra, and flow cytometric analysis was performed on an LSR-II instrument (BD Biosciences). Analysis was done using FlowJo® software (Tree Star). In all analyses, gating on the light scatter signature of small lymphocytes was followed by progressive gating on the CD3+ population and then the CD4+/CD8− versus CD4−/CD8+ T cell subsets. Antigen-specific response frequencies for CD4+ or CD8+ T cell populations were routinely determined from intracellular expression of CD69 and either or both IFN-γ and TNF-α [in select experiments, responses were also characterized by intracellular CD69 and either IL-2 or MIP-1β production or CD107 externalization (11)]. In other select experiments, Boolean gates of (CD69+/TNF-α+ and/or CD69+/IFN-γ+) were generated and expression of CD28 and CCR7 was determined on the gated (responding) CD8+ T cell population. Response frequencies were reported after background subtraction and memory correction, as described (Pitcher C J et al, *J Immunol* 168, 29 (2002); incorporated by reference herein). For epitope deconvolution experiments, stricter response criteria were used to prevent false positives. In these studies, a response to a given 15mer peptide was considered positive if the frequency of events clustered as CD69$^+$, TNF-α$^+$, and IFN-γ$^+$ was >0.05%, with background<0.01% in at least two independent assays. The classification of individual peptide responses as MHC-I- versus MHC-II-associated was based on >90% inhibition of the response by either MHC-I or MHC-II blockade relative to the isotype control. Responses that did not meet these criteria were considered indeterminate. Minimal independent epitope numbers were estimated from the positive responses identified by testing of consecutive 15mer peptides by the following criteria: single positive peptide=1 independent epitope; 2 adjacent positive peptides=1 independent epitope; 3 adjacent positive peptides=2 independent epitopes; 4 adjacent positive peptides=2 independent epitopes; and 5 adjacent positive peptides=3 independent epitopes. These estimations of the minimal number of independent epitopes were initially conducted without the benefit of the MHC association data, but were then revised using the same criteria, applied independently for MHC-I- versus MHC-II-blocked responses.

Statistics: For comparisons of independent samples, we applied bivariate Mann-Whitney U tests, also known as Wilcoxon rank sum tests. For one-sample comparisons to a fixed null-hypothesized value (such as percentages compared to 100%), we applied one-sample Wilcoxon signed rank tests (Wolfe D A and Hollander M Nonparametric Statistical Methods (Wiley, New York, 1973); incorporated by reference herein). All tests were conducted as two-tailed tests with a type I error rate of 5%. We used the R statistical computing language (Rproject (2011); incorporated by reference herein) for all statistical analyses.

The invention claimed is:

1. A human or animal cytomegalovirus (CMV) vector comprising:

a first nucleic acid sequence that encodes a heterologous protein antigen; a second nucleic acid sequence that encodes UL128 or an ortholog thereof; and a third nucleic acid sequence that encodes UL131 or an ortholog thereof; wherein the vector does not express an active UL130 protein; or (ii) a first nucleic acid sequence that encodes a heterologous protein antigen; a second nucleic acid sequence that encodes UL130 or an ortholog thereof; and a third nucleic acid sequence that encodes UL131 or an ortholog thereof; wherein the vector does not express an active UL128 protein.

2. The vector of claim 1, wherein the vector comprises a mutation in UL128 or UL130 selected from a point mutation, a frameshift mutation, or a deletion of all or less than all of UL128 or UL130.

3. The vector of claim 1, further comprising a fourth nucleic acid sequence which comprises an antisense sequence or an RNAi sequence that inhibits the expression of UL128 or UL130.

4. The vector of claim 1, wherein the heterologous antigen comprises a pathogen specific antigen.

5. The vector of claim 4, wherein the pathogen specific antigen is derived from human immunodeficiency virus, simian immunodeficiency virus, herpes simplex virus type 1(HSV1), herpes simplex virus type 2 (HSV2), hepatitis B virus, human papillomavirus, or *Mycobacterium tuberculosis*.

6. A method of generating a CD8$^+$ T cell response to a heterologous antigen in a subject, the method comprising administering to the subject an effective amount of a CMV vector according to claim 1; wherein at least 10% of the CD8+ T cells to the heterologous antigen are directed against epitopes presented by Major Histocompatibility Complexes (MHO Class II.

7. The method of claim 6, wherein at least 50% of the CD8$^+$ T cells to the heterologous antigen are directed against epitopes presented by MHC Class II.

8. The method of claim 7, wherein the heterologous antigen comprises a pathogen specific antigen.

9. The method of claim 8, wherein the pathogen specific antigen is derived from human immunodeficiency virus, simian immunodeficiency virus, herpes simplex virus type 1 (HSV1), herpes simplex virus type 2 (HSV2), hepatitis B virus, human papillomavirus, or *Mycobacterium tuberculosis*.

10. The method of claim 6, wherein the subject is a rhesus macaque that has been previously exposed to RhCMV, and wherein the CMV vector is an RhCMV vector.

11. The method of claim 6, wherein the subject is a human that has been previously exposed to HCMV, and wherein the CMV vector is an attenuated HCMV vector.

12. The method of claim 6, wherein the administering comprises intravenous, intramuscular, intraperitoneal, or oral administration.

13. The vector of claim 1, wherein the heterologous antigen comprises a cancer antigen.

14. The vector of claim 13, wherein the cancer antigen is a prostate cancer antigen.

15. The vector of claim 1, wherein the CMV vector is an attenuated HCMV vector.

16. The vector of claim 1, wherein the CMV vector is an RhCMV vector.

17. The method of claim 7, wherein the heterologous antigen comprises a cancer antigen.

18. The method of claim 17, wherein the cancer antigen is a prostate cancer antigen.

19. A method of generating a $CD8^+$ T cell response to a pathogen specific antigen in a human subject that has been previously exposed to HCMV, the method comprising administering to the subject an effective amount of a HCMV vector comprising;

(i) a first nucleic acid sequence that encodes a pathogen specific antigen; a second nucleic acid sequence that encodes UL128 or an ortholog thereof and a third nucleic acid sequence that encodes UL131 or an ortholog thereof; wherein the vector does not express an active UL130 protein; or (ii) a first nucleic acid sequence that encodes a pathogen specific antigen; a second nucleic acid sequence that encodes UL130 or an ortholog thereof and a third nucleic acid sequence that encodes UL131 or an ortholog thereof; wherein the vector does not express an active UL128 protein;

wherein at least 10% of the CD8+ T cells to the pathogen specific antigen are directed against epitopes presented by MHC Class II; and wherein the pathogen specific antigen is derived from herpes simplex virus type 1 (HSV1), herpes simplex virus type 2 (HSV2), hepatitis B virus, *Mycobacterium tuberculosis*, or human papillomavirus.

20. The method of claim 19, wherein at least 50% of the $CD8^+$ T cells to the pathogen specific antigen are directed against epitopes presented by MEW Class II.

21. The method of claim 19, wherein the administering comprises intravenous, intramuscular, intraperitoneal, or oral administration.

22. The vector of claim 1, wherein the heterologous antigen comprises an antigen derived from *Mycobacterium tuberculosis*.

23. The method of claim 6, wherein the heterologous antigen comprises an antigen derived from *Mycobacterium tuberculosis*.

* * * * *

```
                            SEQUENCE LISTING

<160> NUMBER OF SEQ ID NOS: 34

<210> SEQ ID NO 1
<211> LENGTH: 20
<212> TYPE: DNA
<213> ORGANISM: Artificial Sequence
<220> FEATURE:
<223> OTHER INFORMATION: MHC-DRB specific primer

<400> SEQUENCE: 1
ctggtcctgt cctgttctcc                                              20

<210> SEQ ID NO 2
<211> LENGTH: 20
<212> TYPE: DNA
<213> ORGANISM: Artificial Sequence
<220> FEATURE:
<223> OTHER INFORMATION: MHC-DRB specific primer

<400> SEQUENCE: 2
tggaaggtcc agtctccatt                                              20

<210> SEQ ID NO 3
<211> LENGTH: 19
<212> TYPE: DNA
<213> ORGANISM: Artificial Sequence
<220> FEATURE:
<223> OTHER INFORMATION: Mamu-DRB Universal primer

<400> SEQUENCE: 3
gacactgatg gtgctgagc                                               19

<210> SEQ ID NO 4
<211> LENGTH: 19
<212> TYPE: DNA
<213> ORGANISM: Artificial Sequence
<220> FEATURE:
<223> OTHER INFORMATION: Mamu-DRB Universal primer

<400> SEQUENCE: 4
gctgcactgt gaagctctc                                               19

<210> SEQ ID NO 5
<211> LENGTH: 25
<212> TYPE: DNA
<213> ORGANISM: Artificial Sequence
<220> FEATURE:
<223> OTHER INFORMATION: Universal primer

<400> SEQUENCE: 5
cgtatcgcct ccctcgcgcc atcag                                        25

<210> SEQ ID NO 6
<211> LENGTH: 25
<212> TYPE: DNA
<213> ORGANISM: Artificial Sequence
<220> FEATURE:
<223> OTHER INFORMATION: Universal Primer
```

-continued

<400> SEQUENCE: 6
ctatgcgcct tgccagcccg ctcag                                        25

<210> SEQ ID NO 7
<211> LENGTH: 15
<212> TYPE: PRT
<213> ORGANISM: Artificial Sequence
<220> FEATURE:
<223> OTHER INFORMATION: CD8+ Gag epitope

<400> SEQUENCE: 7

Lys Cys Val Arg Met Tyr Asn Pro Thr Asn Ile Leu Asp Val Lys
1               5                   10                  15

<210> SEQ ID NO 8
<211> LENGTH: 14
<212> TYPE: PRT
<213> ORGANISM: Artificial Sequence
<220> FEATURE:
<223> OTHER INFORMATION: CD8+ Gag epitope

<400> SEQUENCE: 8

Cys Val Arg Met Tyr Asn Pro Thr Asn Ile Leu Asp Val Lys
1               5                   10

<210> SEQ ID NO 9
<211> LENGTH: 14
<212> TYPE: PRT
<213> ORGANISM: Artificial Sequence
<220> FEATURE:
<223> OTHER INFORMATION: CD8+ Gag epitope

<400> SEQUENCE: 9

Lys Cys Val Arg Met Tyr Asn Pro Thr Asn Ile Leu Asp Val
1               5                   10

<210> SEQ ID NO 10
<211> LENGTH: 13
<212> TYPE: PRT
<213> ORGANISM: Artificial Sequence
<220> FEATURE:
<223> OTHER INFORMATION: CD8+ Gag epitope

<400> SEQUENCE: 10

Val Arg Met Tyr Asn Pro Thr Asn Ile Leu Asp Val Lys
1               5                   10

<210> SEQ ID NO 11
<211> LENGTH: 13
<212> TYPE: PRT
<213> ORGANISM: Artificial Sequence
<220> FEATURE:
<223> OTHER INFORMATION: CD8+ Gag epitope

<400> SEQUENCE: 11

Lys Cys Val Arg Met Tyr Asn Pro Thr Asn Ile Leu Asp
1               5                   10

<210> SEQ ID NO 12
<211> LENGTH: 12
<212> TYPE: PRT
<213> ORGANISM: Artificial Sequence
<220> FEATURE:
<223> OTHER INFORMATION: CD8+ Gag epitope

<400> SEQUENCE: 12

```
Arg Met Tyr Asn Pro Thr Asn Ile Leu Asp Val Lys
1               5                   10
```

<210> SEQ ID NO 13
<211> LENGTH: 12
<212> TYPE: PRT
<213> ORGANISM: Artificial Sequence
<220> FEATURE:
<223> OTHER INFORMATION: CD8+ Gag epitope

<400> SEQUENCE: 13

```
Lys Cys Val Arg Met Tyr Asn Pro Thr Asn Ile Leu
1               5                   10
```

<210> SEQ ID NO 14
<211> LENGTH: 11
<212> TYPE: PRT
<213> ORGANISM: Artificial Sequence
<220> FEATURE:
<223> OTHER INFORMATION: CD8+ Gag epitope

<400> SEQUENCE: 14

```
Met Tyr Asn Pro Thr Asn Ile Leu Asp Val Lys
1               5                   10
```

<210> SEQ ID NO 15
<211> LENGTH: 11
<212> TYPE: PRT
<213> ORGANISM: Artificial Sequence
<220> FEATURE:
<223> OTHER INFORMATION: CD8+ Gag epitope

<400> SEQUENCE: 15

```
Lys Cys Val Arg Met Tyr Asn Pro Thr Asn Ile
1               5                   10
```

<210> SEQ ID NO 16
<211> LENGTH: 10
<212> TYPE: PRT
<213> ORGANISM: Artificial Sequence
<220> FEATURE:
<223> OTHER INFORMATION: CD8+ Gag epitope

<400> SEQUENCE: 16

```
Tyr Asn Pro Thr Asn Ile Leu Asp Val Lys
1               5                   10
```

<210> SEQ ID NO 17
<211> LENGTH: 10
<212> TYPE: PRT
<213> ORGANISM: Artificial Sequence
<220> FEATURE:
<223> OTHER INFORMATION: CD8+ Gag epitope

<400> SEQUENCE: 17

```
Lys Cys Val Arg Met Tyr Asn Pro Thr Asn
1               5                   10
```

<210> SEQ ID NO 18
<211> LENGTH: 9
<212> TYPE: PRT
<213> ORGANISM: Artificial Sequence
<220> FEATURE:
<223> OTHER INFORMATION: CD8+ Gag epitope

<400> SEQUENCE: 18

```
Asn Pro Thr Asn Ile Leu Asp Val Lys
1               5

<210> SEQ ID NO 19
<211> LENGTH: 9
<212> TYPE: PRT
<213> ORGANISM: Artificial Sequence
<220> FEATURE:
<223> OTHER INFORMATION: CD8+ Gag epitope

<400> SEQUENCE: 19

Lys Cys Val Arg Met Tyr Asn Pro Thr
1               5

<210> SEQ ID NO 20
<211> LENGTH: 9
<212> TYPE: PRT
<213> ORGANISM: Artificial Sequence
<220> FEATURE:
<223> OTHER INFORMATION: CD8+ Gag epitope

<400> SEQUENCE: 20

Arg Met Tyr Asn Pro Thr Asn Ile Leu
1               5

<210> SEQ ID NO 21
<211> LENGTH: 15
<212> TYPE: PRT
<213> ORGANISM: Artificial Sequence
<220> FEATURE:
<223> OTHER INFORMATION: CD8+ Gag epitope

<400> SEQUENCE: 21

Gly Pro Lys Glu Pro Phe Gln Ser Tyr Val Asp Arg Phe Tyr Lys
1               5                   10                  15

<210> SEQ ID NO 22
<211> LENGTH: 14
<212> TYPE: PRT
<213> ORGANISM: Artificial Sequence
<220> FEATURE:
<223> OTHER INFORMATION: CD8+ Gag epitope

<400> SEQUENCE: 22

Pro Lys Glu Pro Phe Gln Ser Tyr Val Asp Arg Phe Tyr Lys
1               5                   10

<210> SEQ ID NO 23
<211> LENGTH: 14
<212> TYPE: PRT
<213> ORGANISM: Artificial Sequence
<220> FEATURE:
<223> OTHER INFORMATION: CD8+ Gag epitope

<400> SEQUENCE: 23

Gly Pro Lys Glu Pro Phe Gln Ser Tyr Val Asp Arg Phe Tyr
1               5                   10

<210> SEQ ID NO 24
<211> LENGTH: 13
<212> TYPE: PRT
<213> ORGANISM: Artificial Sequence
<220> FEATURE:
<223> OTHER INFORMATION: CD8+ Gag epitope

<400> SEQUENCE: 24

Lys Glu Pro Phe Gln Ser Tyr Val Asp Arg Phe Tyr Lys
```

```
1               5                  10
```

<210> SEQ ID NO 25
<211> LENGTH: 13
<212> TYPE: PRT
<213> ORGANISM: Artificial Sequence
<220> FEATURE:
<223> OTHER INFORMATION: CD8+ Gag epitope

<400> SEQUENCE: 25

```
Gly Pro Lys Glu Pro Phe Gln Ser Tyr Val Asp Arg Phe
1               5                  10
```

<210> SEQ ID NO 26
<211> LENGTH: 12
<212> TYPE: PRT
<213> ORGANISM: Artificial Sequence
<220> FEATURE:
<223> OTHER INFORMATION: CD8+ Gag epitope

<400> SEQUENCE: 26

```
Glu Pro Phe Gln Ser Tyr Val Asp Arg Phe Tyr Lys
1               5                  10
```

<210> SEQ ID NO 27
<211> LENGTH: 12
<212> TYPE: PRT
<213> ORGANISM: Artificial Sequence
<220> FEATURE:
<223> OTHER INFORMATION: CD8+ Gag epitope

<400> SEQUENCE: 27

```
Gly Pro Lys Glu Pro Phe Gln Ser Tyr Val Asp Arg
1               5                  10
```

<210> SEQ ID NO 28
<211> LENGTH: 11
<212> TYPE: PRT
<213> ORGANISM: Artificial Sequence
<220> FEATURE:
<223> OTHER INFORMATION: CD8+ Gag epitope

<400> SEQUENCE: 28

```
Pro Phe Gln Ser Tyr Val Asp Arg Phe Tyr Lys
1               5                  10
```

<210> SEQ ID NO 29
<211> LENGTH: 11
<212> TYPE: PRT
<213> ORGANISM: Artificial Sequence
<220> FEATURE:
<223> OTHER INFORMATION: CD8+ Gag epitope

<400> SEQUENCE: 29

```
Gly Pro Lys Glu Pro Phe Gln Ser Tyr Val Asp
1               5                  10
```

<210> SEQ ID NO 30
<211> LENGTH: 10
<212> TYPE: PRT
<213> ORGANISM: Artificial Sequence
<220> FEATURE:
<223> OTHER INFORMATION: CD8+ Gag epitope

<400> SEQUENCE: 30

```
Phe Gln Ser Tyr Val Asp Arg Phe Tyr Lys
1               5                  10
```

```
<210> SEQ ID NO 31
<211> LENGTH: 10
<212> TYPE: PRT
<213> ORGANISM: Artificial Sequence
<220> FEATURE:
<223> OTHER INFORMATION: CD8+ Gag epitope

<400> SEQUENCE: 31

Gly Pro Lys Glu Pro Phe Gln Ser Tyr Val
1               5                   10

<210> SEQ ID NO 32
<211> LENGTH: 9
<212> TYPE: PRT
<213> ORGANISM: Artificial Sequence
<220> FEATURE:
<223> OTHER INFORMATION: CD8+ Gag epitope

<400> SEQUENCE: 32

Gln Ser Tyr Val Asp Arg Phe Tyr Lys
1               5

<210> SEQ ID NO 33
<211> LENGTH: 9
<212> TYPE: PRT
<213> ORGANISM: Artificial Sequence
<220> FEATURE:
<223> OTHER INFORMATION: CD8+ Gag epitope

<400> SEQUENCE: 33

Gly Pro Lys Glu Pro Phe Gln Ser Tyr
1               5

<210> SEQ ID NO 34
<211> LENGTH: 12
<212> TYPE: PRT
<213> ORGANISM: Artificial Sequence
<220> FEATURE:
<223> OTHER INFORMATION: CD8+ Gag epitope

<400> SEQUENCE: 34

Pro Lys Glu Pro Phe Gln Ser Tyr Val Asp Arg Phe
1               5                   10
```

UNITED STATES PATENT AND TRADEMARK OFFICE
CERTIFICATE OF CORRECTION

PATENT NO. : 10,316,334 B2
APPLICATION NO. : 15/693558
DATED : June 11, 2019
INVENTOR(S) : Picker et al.

Page 1 of 1

It is certified that error appears in the above-identified patent and that said Letters Patent is hereby corrected as shown below:

In the Claims

Claim 6, Column 48, Line 64, "(MHO" should read --MHC--.

Claim 8, Column 49, Line 1, "7" should read --6--.

Claim 17, Column 49, Line 26, "7" should read --6--.

Claim 19 (i), Column 50, Line 3, after "thereof" insert --;--.

Claim 19 (ii), Column 50, Line 9, after "thereof" insert --;--.

Claim 20, Column 50, Line 21, "MEW" should read --MHC--.

Signed and Sealed this
Tenth Day of September, 2019

Andrei Iancu
*Director of the United States Patent and Trademark Office*